US006355019B1

(12) United States Patent
Kriesel et al.

(10) Patent No.: US 6,355,019 B1
(45) Date of Patent: Mar. 12, 2002

(54) VARIABLE RATE INFUSION APPARATUS WITH INDICATOR AND ADJUSTABLE RATE CONTROL

(75) Inventors: Marshall S. Kriesel, St. Paul; Thomas N. Thompson, Richfield; William F. Kuester, Blaine; Rolf Hogan, Brooklyn Center, all of MN (US)

(73) Assignee: Science Incorporated, Bloomington, MN (US)

(*) Notice: Subject to any disclaimer, the term of this patent is extended or adjusted under 35 U.S.C. 154(b) by 0 days.

(21) Appl. No.: 09/312,588

(22) Filed: May 14, 1999

Related U.S. Application Data

(63) Continuation-in-part of application No. 09/165,713, filed on Oct. 2, 1998, now Pat. No. 6,231,545, which is a continuation-in-part of application No. 08/768,663, filed on Dec. 18, 1996, now Pat. No. 5,840,071.

(51) Int. Cl.$^7$ ............................................. A61M 37/00
(52) U.S. Cl. ................... 604/132; 604/151; 604/890.1; 604/248
(58) Field of Search ................................. 604/132, 153, 604/246, 82, 890.1, 122, 123, 131, 151, 118, 248, 207, 186, 191, 203; 128/DIG. 12

(56) References Cited

U.S. PATENT DOCUMENTS

| | | | | | |
|---|---|---|---|---|---|
| 5,336,180 A | * | 8/1994 | Kriesel et al. | ................. | 604/82 |
| 5,484,415 A | * | 1/1996 | Kriesel | ........................ | 604/132 |
| 5,830,187 A | * | 11/1998 | Kriesel et al. | ............... | 604/132 |
| 5,962,794 A | * | 10/1999 | Kriesel et al. | ........... | 73/861.47 |

* cited by examiner

*Primary Examiner*—Anhtuan T. Nguyen
*Assistant Examiner*—Cris L. Rodriguez
(74) *Attorney, Agent, or Firm*—J. E. Brunton, Esq.

(57) ABSTRACT

An apparatus for accurately infusing medicinal agents into an ambulatory patient at specific rates over extended periods of time. The apparatus is of a compact, low profile, laminate construction and includes an elastic distendable membrane, chamber having a fluid outlet. Disposed within the fluid chamber is a thin fluid permeable member which precisely controls the rate of fluid flow through the fluid outlet. The apparatus also includes a highly novel medicament dose dialing feature that allows the user to dial in the appropriate dose to be delivered to the patient. Additionally, the apparatus includes a fill assembly comprising a field fill vial that can be readily filled in the field.

10 Claims, 48 Drawing Sheets

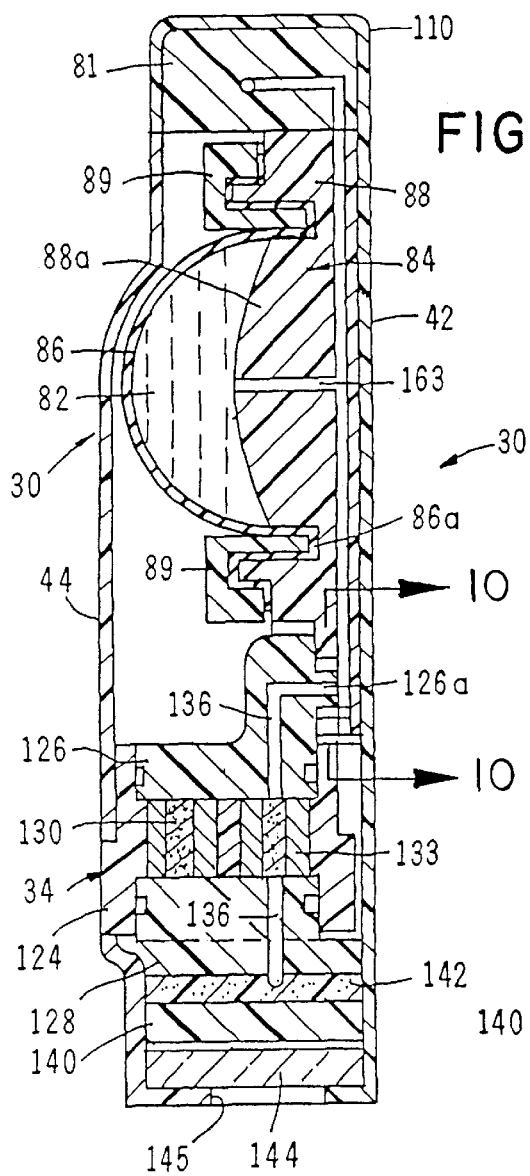
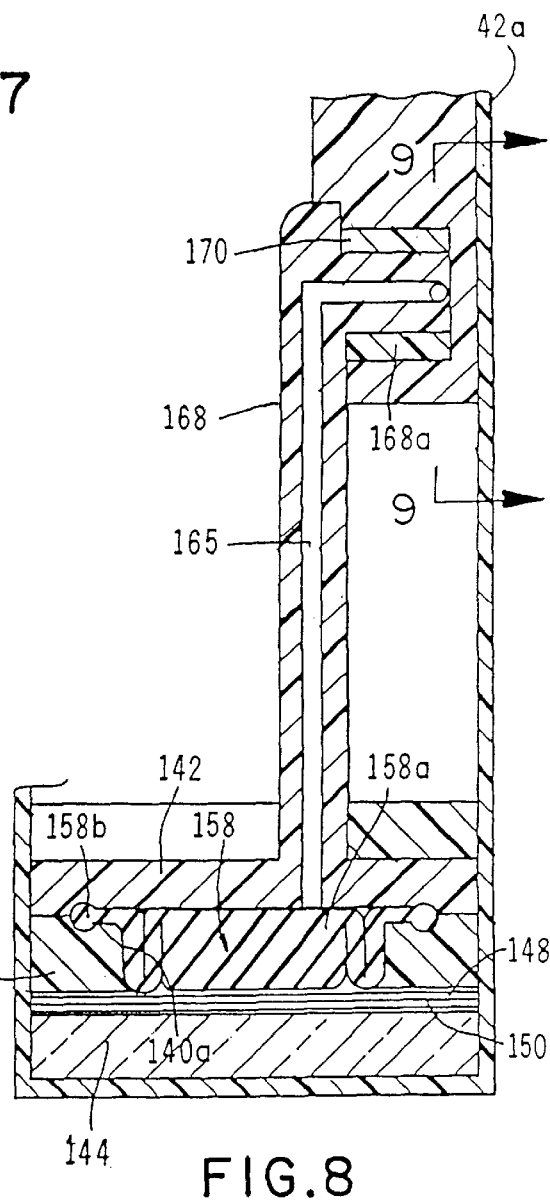
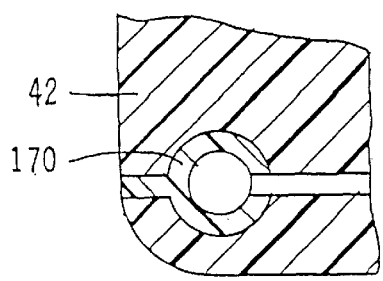

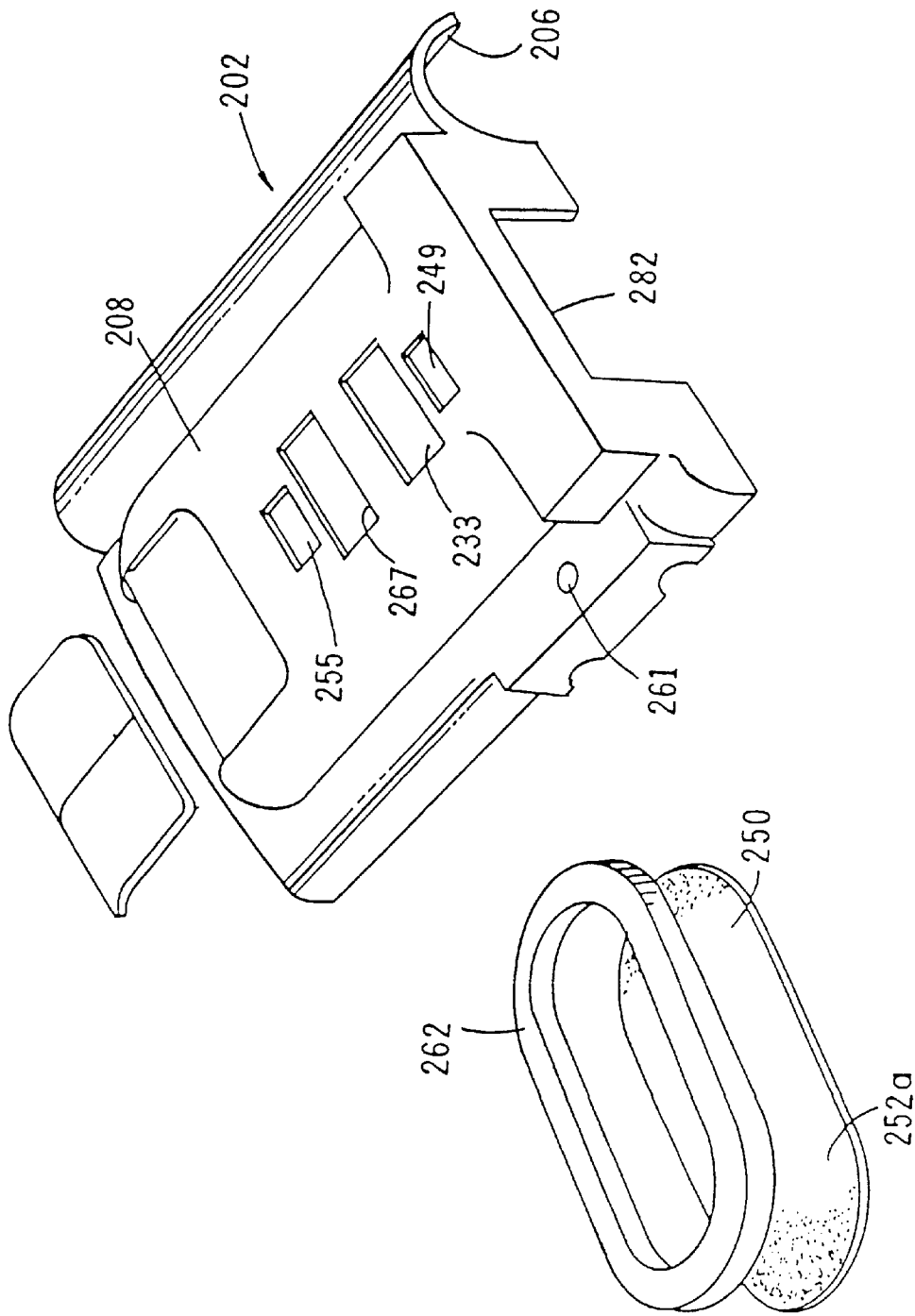

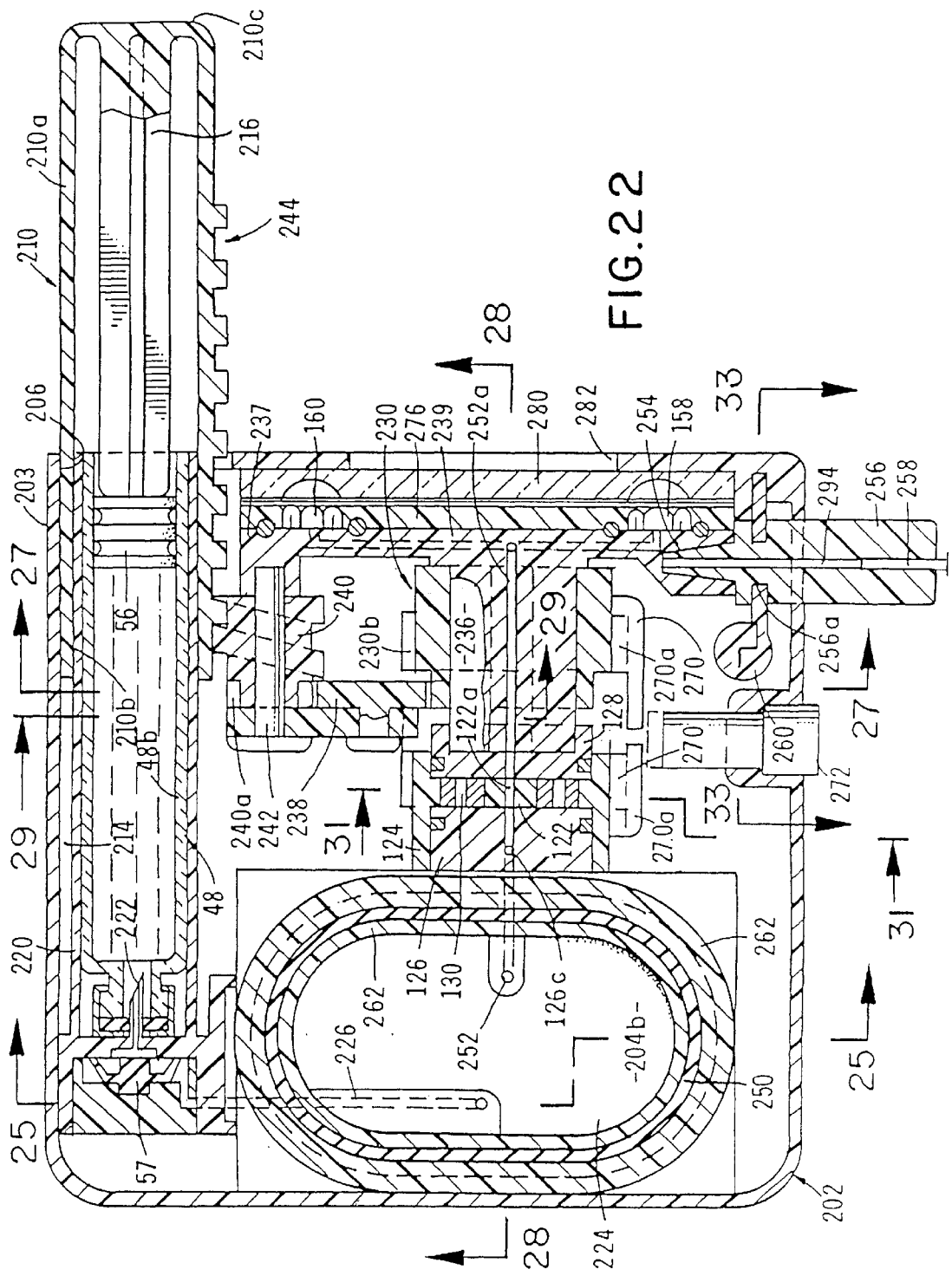

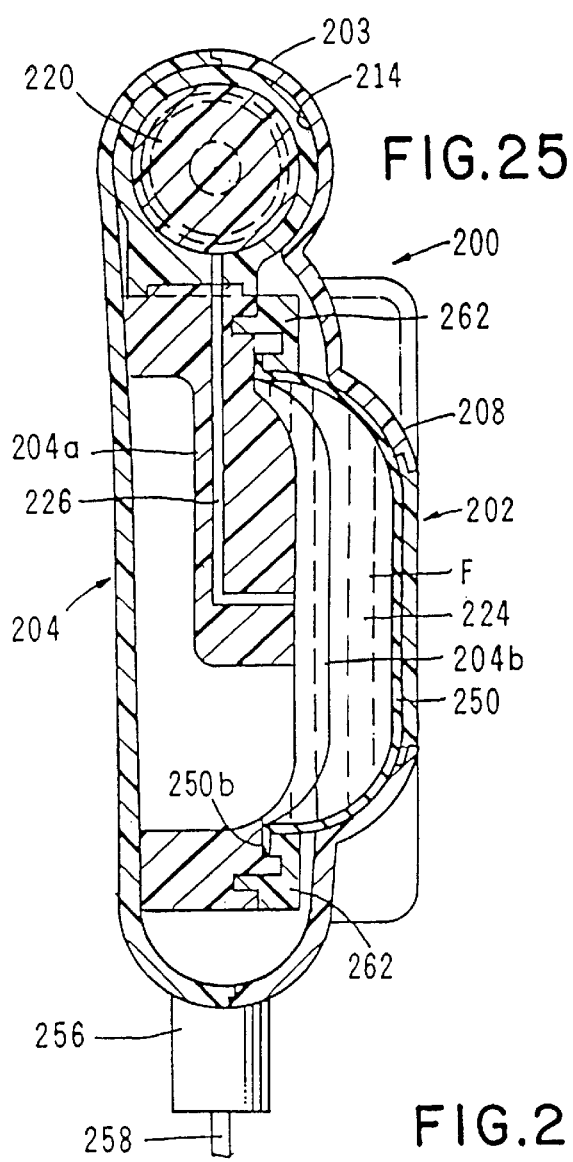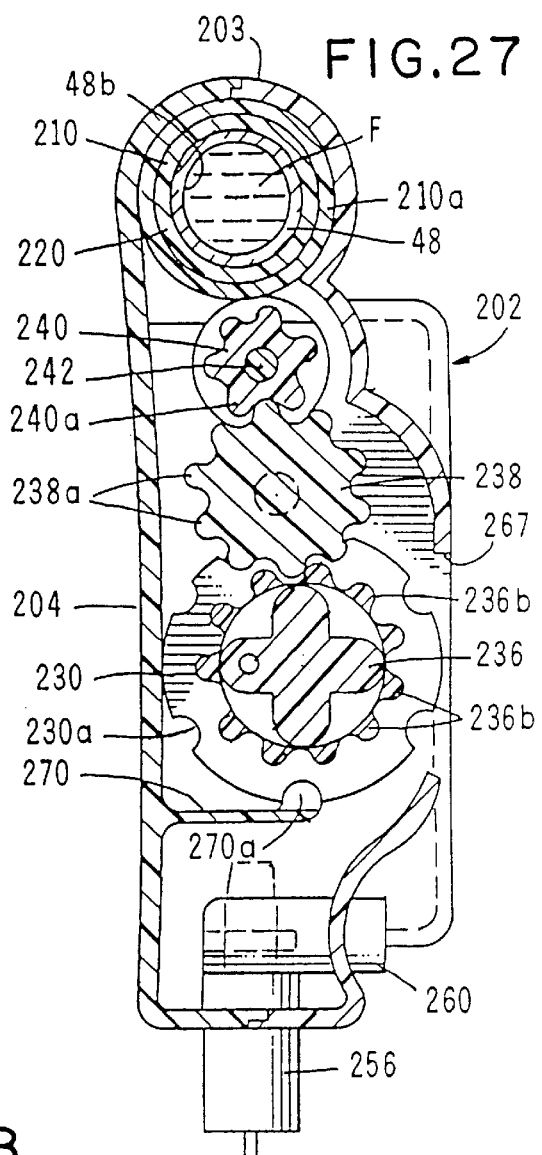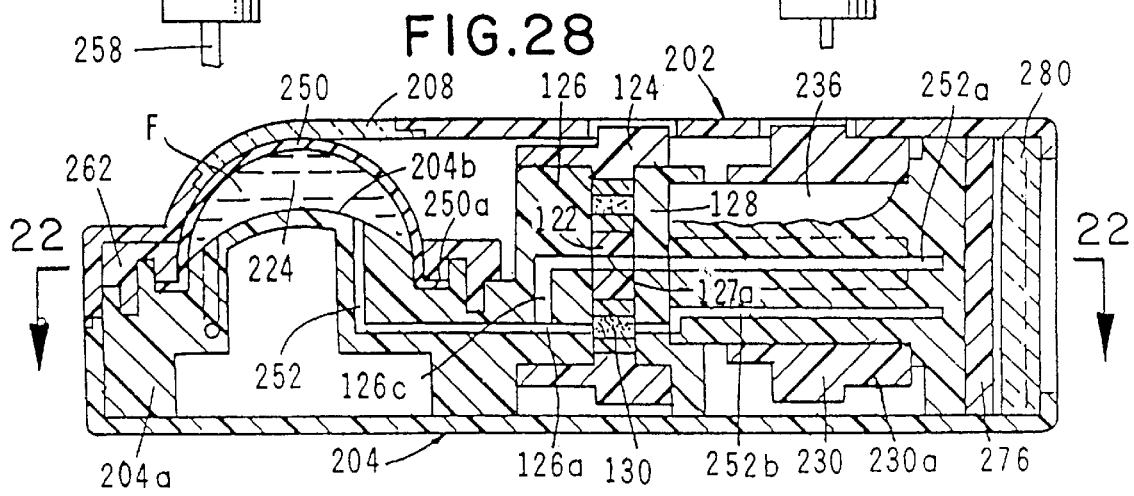

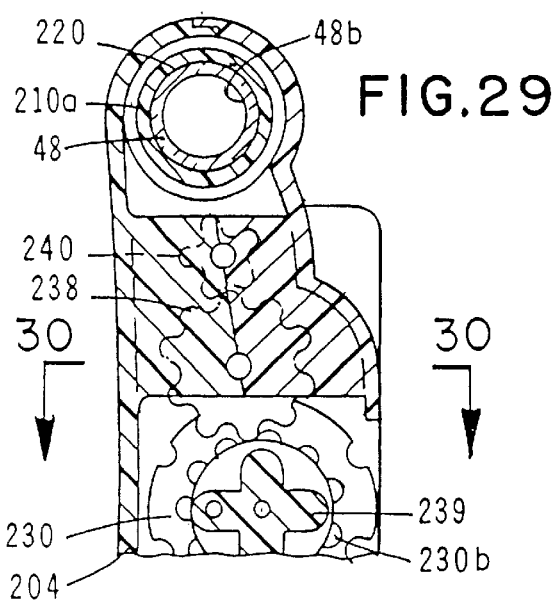
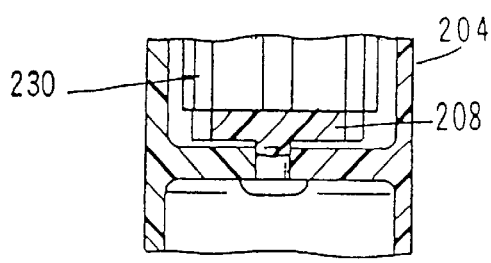
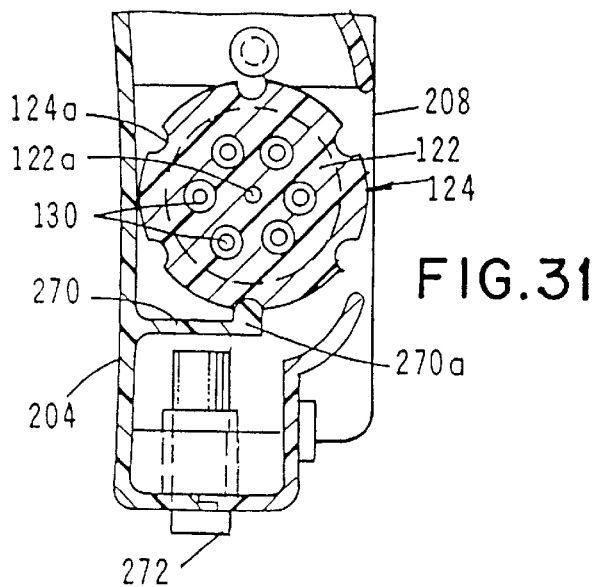
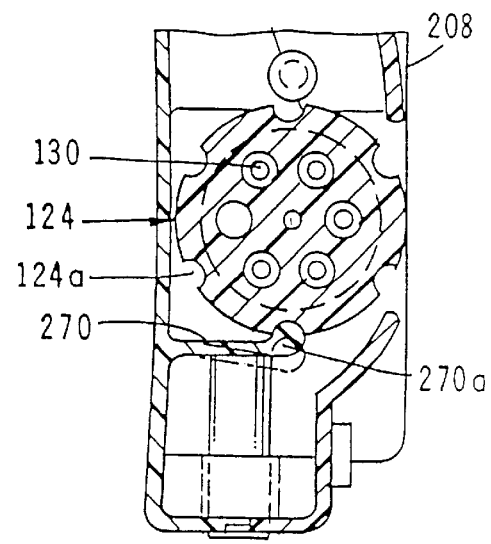
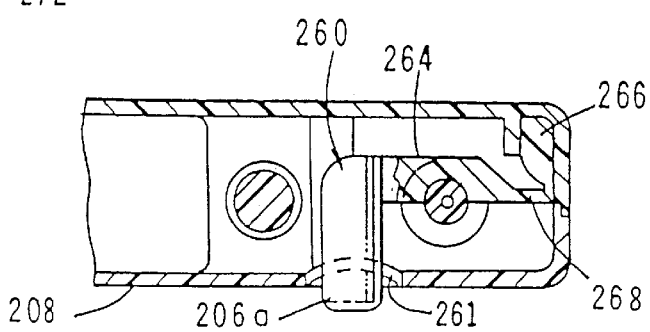

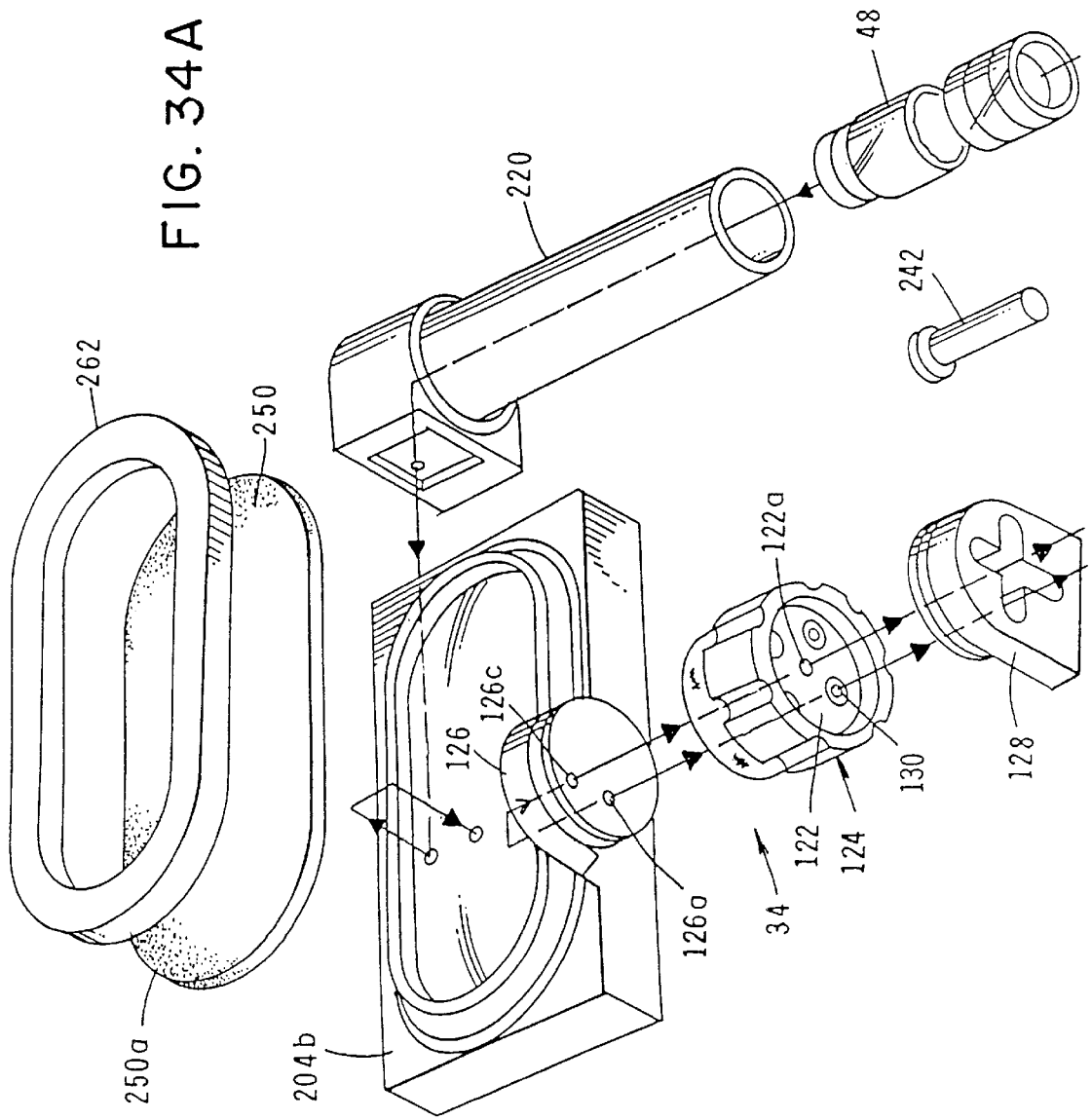

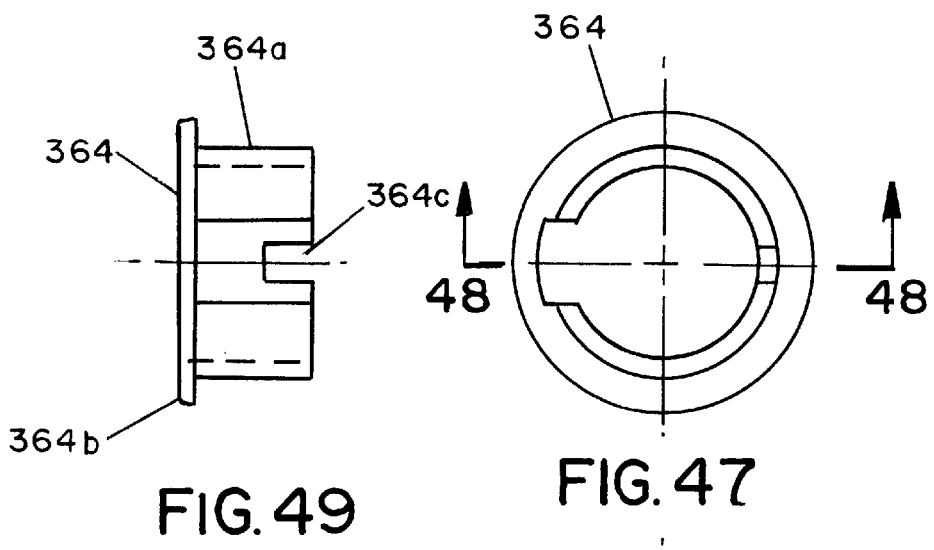
FIG. 49 FIG. 47
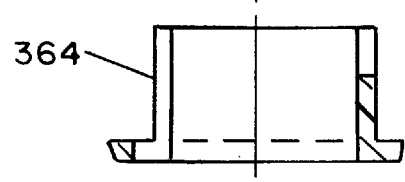
FIG. 48
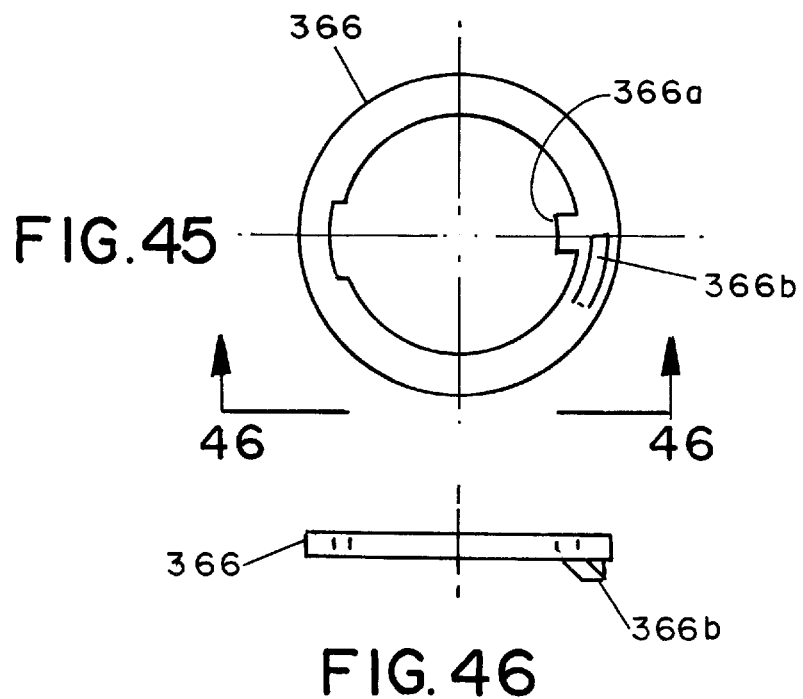
FIG. 45
FIG. 46

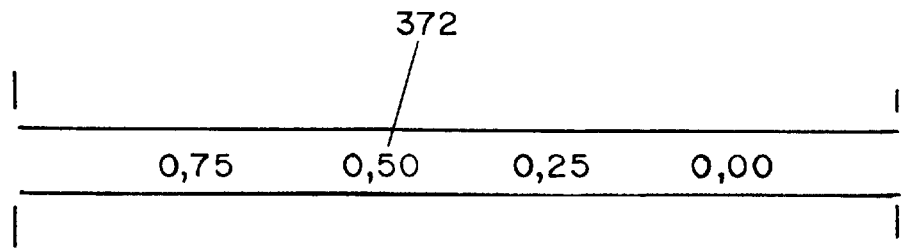
FIG. 53
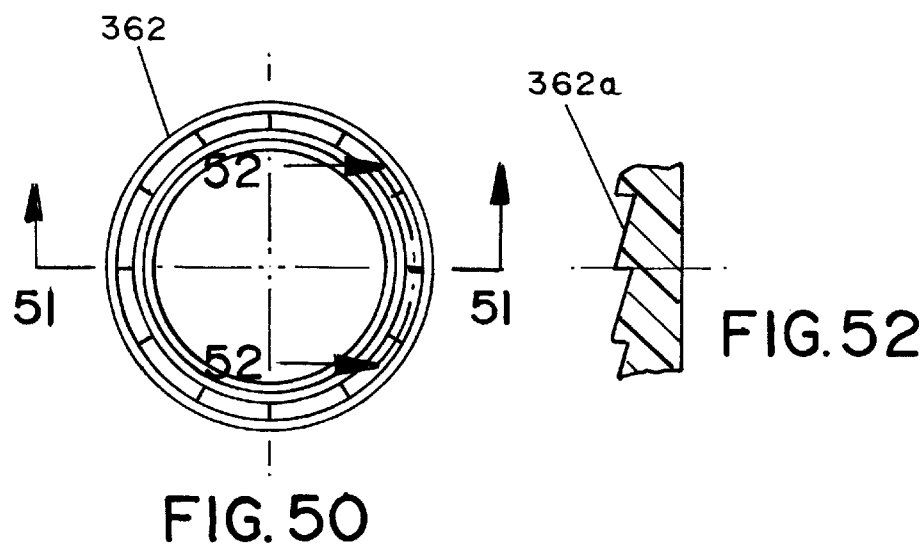
FIG. 52
FIG. 50
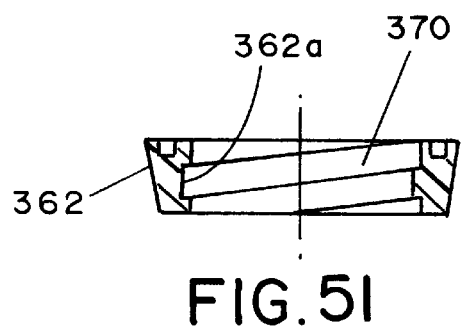
FIG. 51

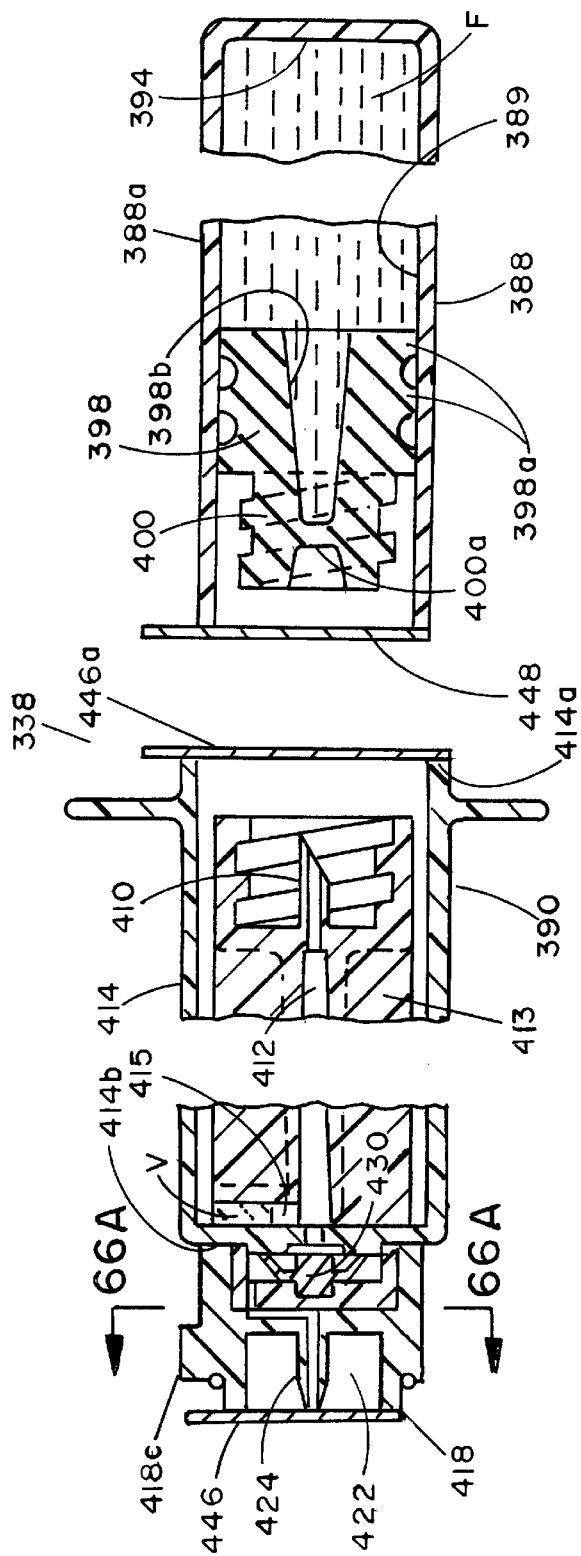
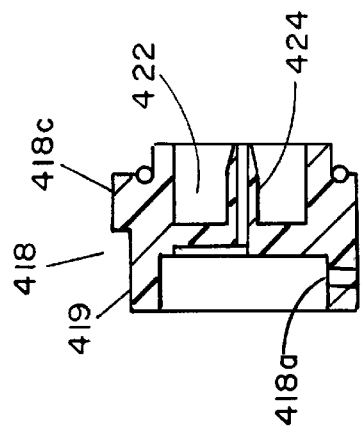
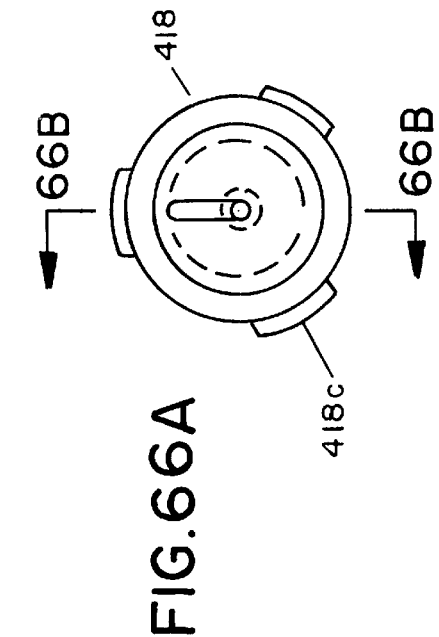
FIG. 66
FIG. 66A
FIG. 66B

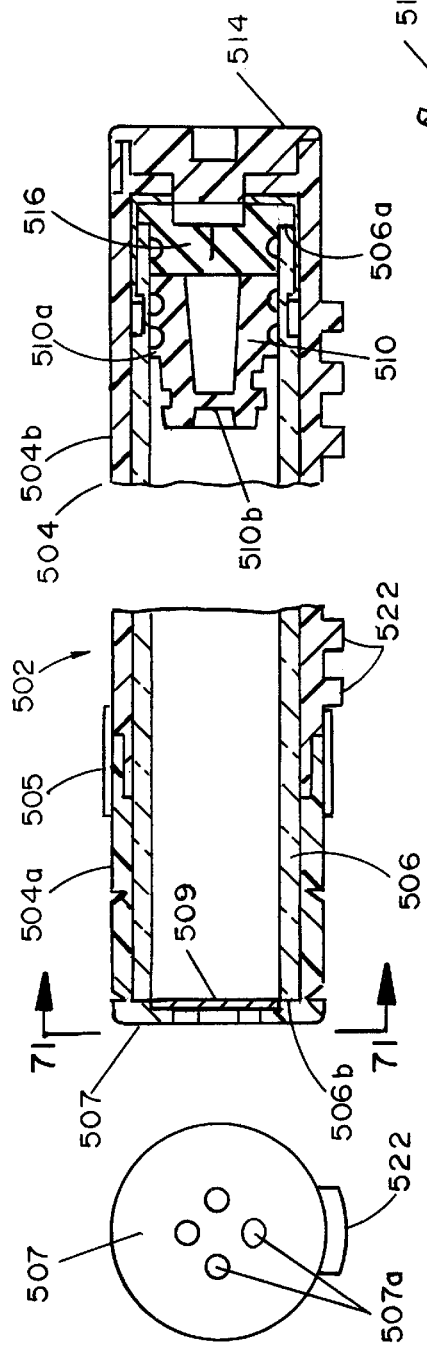
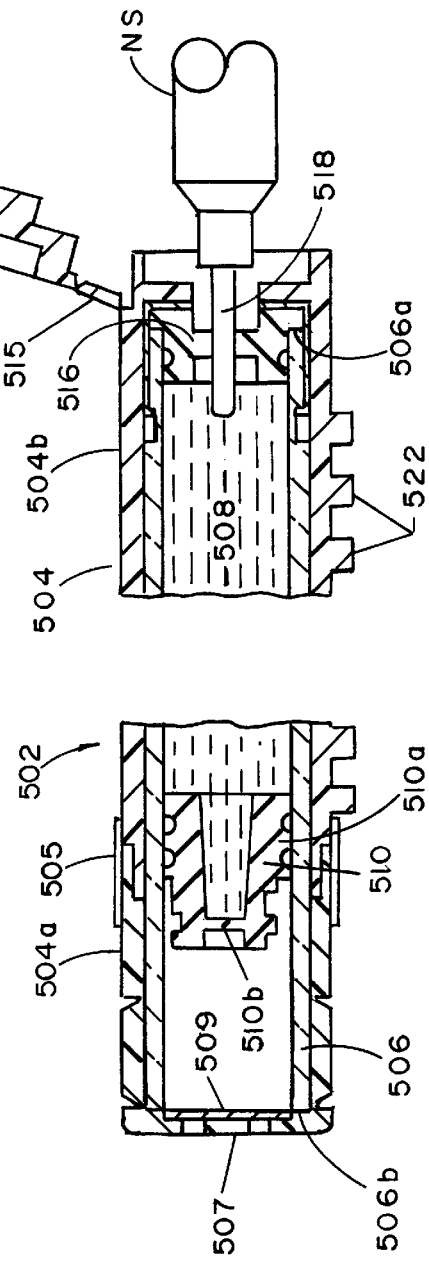
FIG. 70
FIG. 71
FIG. 72

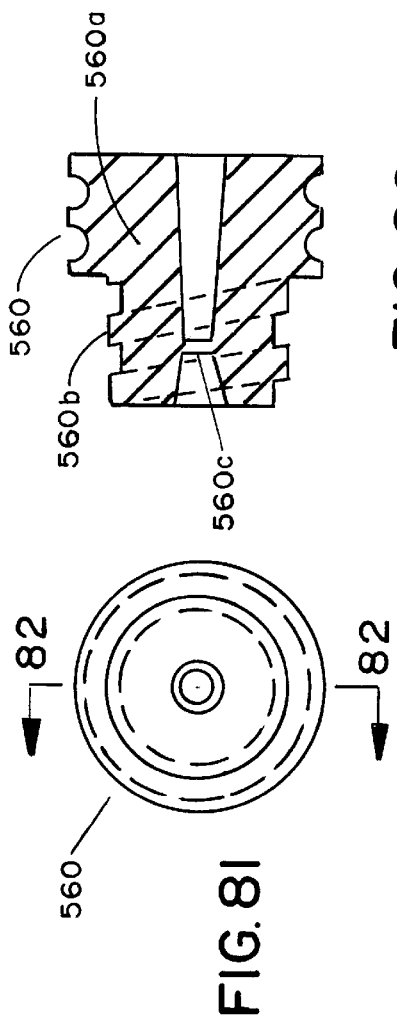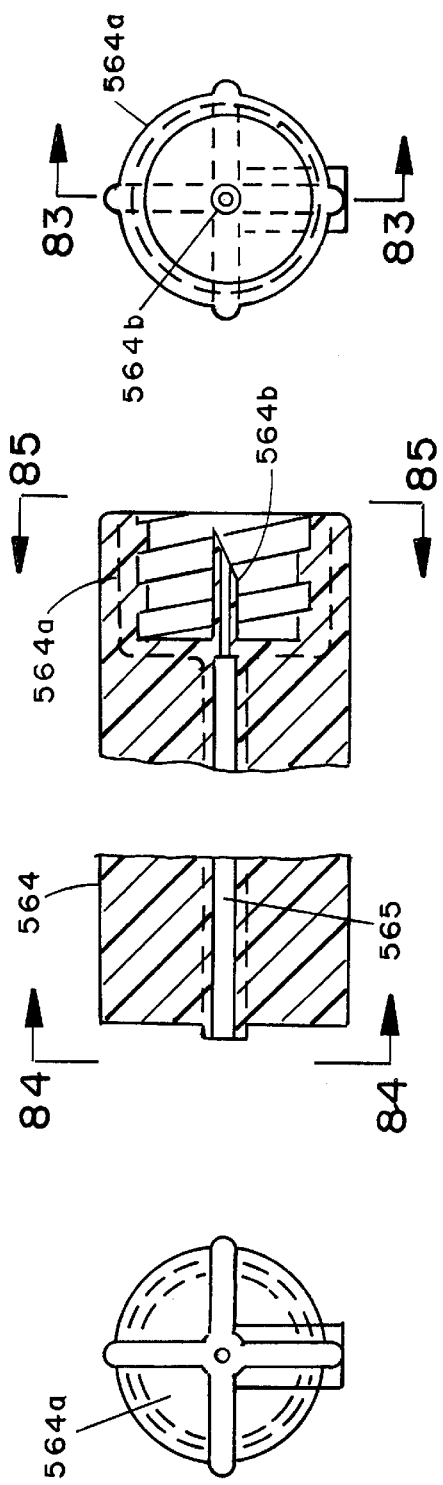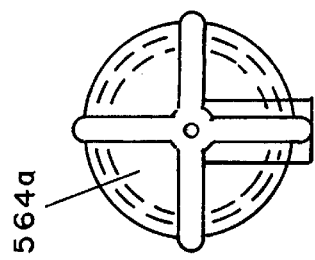

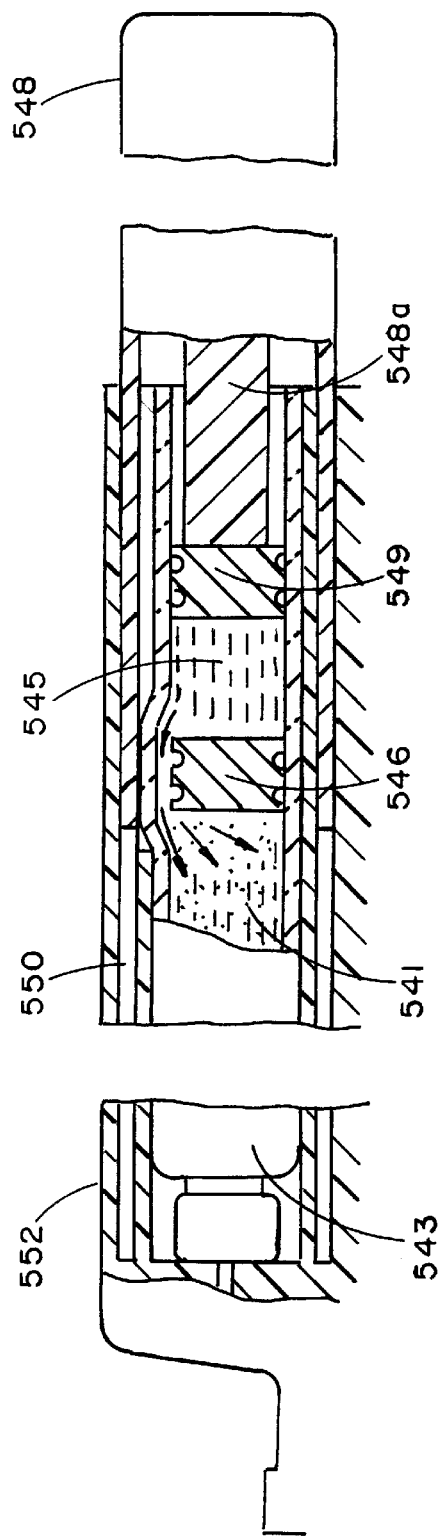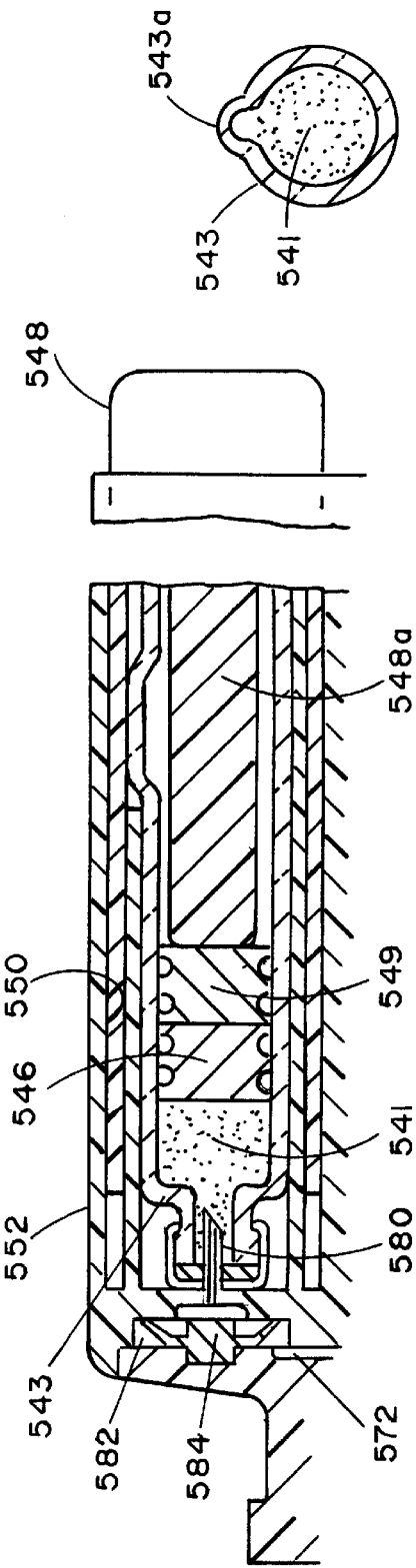

VARIABLE RATE INFUSION APPARATUS WITH INDICATOR AND ADJUSTABLE RATE CONTROL

This is a Continuation-In-Part of U.S. application Ser. No. 09/165,713 filed Oct. 2, 1998 now U.S. Pat. No. 6,231,545 which is a Continuation-In Part of U.S. application Ser. No. 08/768,663 filed Dec. 18, 1996 now U.S. Pat. No. 5,840,071.

BACKGROUND OF THE INVENTION

1. Field of the Invention

The present invention relates generally to fluid delivery devices. More particularly, the invention concerns an improved apparatus for infusing medicinal agents into an ambulatory patient at specific rates over extended periods of time. More particularly, the apparatus includes a novel dose dialing means for precisely adjustably controlling the volume of the dose of medicament to be delivered to the patient.

2. Discussion of the Prior Art

The biotechnology industry emerged in the 1980s as new molecular biological techniques made possible the commercial production of proteins, peptides and other biopharmaceuticals. These molecules are integral to numerous physiological processes and have enormous therapeutic potential as oncolytics, hormones, analgesics, antihypertensives, growth factors and other. It is believed that at the present time there are currently over 600 biotech drugs in advanced stages of development.

Because bioengineered molecules often have an extremely short biological half-life and poor bioavailability, continuous infusion is often considered to be a more economically and therapeutically practical route of drug delivery than oral, ocular, nasal, buccal, intestinal, rectal or pulmonary administration. As will be better appreciated from tile discussion which follows, tile apparatus of the present invention has been specifically engineered for these emerging therapies and will allow highly safe and accurate microscaled ambulatory infusion of drugs with narrow therapeutic windows. In one form of the invention, the apparatus will accept either 1.5 or 3.0 mL vial cartridges of injectable agent, consistent with tile expected dosing requirements of many biopharmaceuticals now under development.

Many of the pharmacological agents flow under development possess a very narrow range of therapeutic effectiveness, for instance, too small a dose results in no effect, while too great a dose results in toxic reaction. Additionally, the ever increasing medicinal use of proteins and peptides has created many challenging new problems concerning means for the effective delivery of the molecules to the patient. In general these molecules are difficult to stabilize and often undergo a variety of physical and chemical transformations including precipitation, aggregation and oxidation. Further, they are poorly absorbed after oral administration. Most proteins now being used or under development are given parenterally in order to insure rapid onset of action, with the main routes of delivery being intravenous, intramuscular, or subcutaneous. Intravenous administration results in the fastest, intramuscular injection is next, and subcutaneous injection exhibits the slowest onset of action. While other noninvasive methods of delivery, such as iontophoresis and nasal or buccal administration have been investigated, they have not been widely adopted.

A major advantage of infusion therapy is the opportunity to avoid repeated injections and to achieve a constant or controlled rate of delivery of the medicinal agents. Accordingly, many types of sophisticated electronic infusion devices have been suggested to achieve complex patters of dosing which are customized to the patient's need and do not require repeated injections in order to maintain a constant level of proteins in the blood. Another major advantage of infusion therapy over repeated needle injections resides in the fact that such therapy is less time consuming and considerably less costly because the caregiver can administer a single dose instead of multiple injections given over a period of time.

The primary disadvantage of infusion therapy is its limiting effect on the patient's lifestyle. This is largely due to the physical size of the prior art devices and the many precautions associated with parenteral therapy. Additionally, many of the prior art portable electromechanical devices are generally quite fragile and must be carefully handled to avoid breakage and preclude operational malfunction. Experience has shown that while a patient will tolerate restrictions on an active lifestyle for short periods of time, long-term use of the prior art devices have tended to create significant patient intolerance. In addition to the precautions associated with using the prior art devices, there are numerous logistical issues of battery changing and frequent replacement and the dedicated pump accessories. These logistical issues substantially contribute to the overall cost and complexity of prior art infusion therapy.

The unique combination of features in the apparatus of the present invention makes it superior to virtually all currently existing competitive systems. For example, although stationary electronic syringe pumps offer an excellent flow rate accuracy of 3–10%, they are expensive, high maintenance devices and do not allow patient mobility. Recently, portable, miniaturized versions of these syringe pumps have been developed which allow greater freedom; however, they are often fragile, non-waterproof and complicated to use, requiring battery and accessory changes. Also problematic is the fact that both of the latter two types of devices often require drugs to be diluted for parenteral administration, which may lead to unnecessary patient overhydration. In addition to syringe systems, depot delivery (via subcutaneous or intramuscular implants) has been developed for continuous infusion; however, its high cost, invasiveness and inability to provide drug stability makes it an unattractive alternative to potential users. Because the present application discloses improvements to the apparatus described in the U.S. Pat. No. 5,840,071, this Patent is also hereby incorporated by reference in its entirely as though fully set forth herein.

As will be better appreciated from the discussion which follows, the apparatus of the invention can be used with minimal professional assistance in an alternate health care environment, such as the home. By way of example, the completely mechanical devices of the invention can be comfortably and conveniently removably affixed to the patient's body and can be used for continuous infusion of various medicinal agents over substantial periods of time.

Because the present invention comprises an improvement over the embodiments of the invention described in Ser. No. 08/768,663, (now U.S. Pat. No. 5,840,071) this Patent is incorporated herein by reference as though fully set for the herein. While the inventions described in U.S. Pat. No. 5,840,071 comprises fluid delivery devices having a fluid reservoir and an indicator assembly for indicating fluid flow through the apparatus, they do not include the highly novel dose dialing feature or the adjustable fluid flow rate mechanism of the present invention which enables the fluid contained within the reservoir of the device to be precisely dispensed at various selected rates. As will be better understood from the description which follows, the novel adjustable fluid flow rate control mechanism of the present invention also includes novel locking means for preventing unauthorized adjustment of the rate control mechanism. This novel locking means is operable only by a physician or health care worker who is in possession of a physician operating key. Accordingly, once a particular flow rate is selected, the patient cannot unilaterally change the flow rate.

SUMMARY OF THE INVENTION

It is an object of the present invention to provide an apparatus for expelling fluids at a precisely controlled rate which is of a compact, low profile, laminate construction. More particularly, it is an object of the invention to provide such an apparatus which can be used for the precise infusion of pharmaceutical agents, including proteins and peptides into an ambulatory patient at controlled rates over extended periods of time.

It is an object of the present invention to provide an apparatus of the aforementioned character which is highly reliable and easy-to-use by lay persons in a non-hospital environment.

Another object of the invention is to provide an apparatus which can be factory prefilled with a wide variety of medicaments or one which can readily be filled in the field shortly prior to use.

A further object of the invention is to provide a low profile, fluid delivery device of laminate construction which can be manufactured inexpensively in large volume by automated machinery.

Another object of the invention is to provide a device of the aforementioned character which includes an adjustable flow rate control means disposed intermediate the fluid reservoir outlet and the outlet port of tile device for precisely controlling the rate of fluid flow from the outlet poll toward the patient.

Another object of the invention is to provide an apparatus of the aforementioned character in which the adjustable flow rate control means comprises a rotatable flow restrictor support disk that can be rotated by the treating physician to selectively position the flow restrictor between the fluid reservoir and the device outlet port.

Another object of the present invention is to provide a flow rate control means of the type described in the preceding paragraph in which the flow restrictors comprise porous frits of varying porosity.

Another object of the present invention is to provide a flow rate control means in which the flow restrictors comprise laser drilled wafers.

Another object of the invention is to provide an apparatus as described in the preceding paragraphs which includes locking means for locking the variable flow rate control disk in a preset position so that the rate control can be set only by the treating physician or an authorized health care worker having an operating key.

Another object of the invention is to provide a device of the character described which embodies a highly novel fluid flow indicator that provides a readily discernible visual indication of fluid flow status through the device.

Another object of the invention is to provide an apparatus of the aforementioned character in which the stored energy source is of a novel construction that can be precisely tailored to continuously deliver fluid from the device to the patient.

Another object of the invention is to provide novel fill means for use in controllably filling the fluid reservoir of the apparatus. More particularly, it is an object of the invention to provide a fill mean that includes a unique dose dialing feature for dialing in the medicament dose to be delivered to the patient.

Another object of the invention is to provide a novel vial assembly for use with the fluid dispenser subassembly of the apparatus which is easy to use, is inexpensive to manufacture, and one which maintains the vial in an aseptic condition until time of use.

By way of summary, the improved fluid delivery apparatus of the present form of the invention comprises five major cooperating subassemblies, namely a base assembly, a fill assembly, an adjustable key operated fluid flow rate control subassembly, a dose dialing feature and a flow indicator subassembly for visually indicating fluid flow through the device. The base assembly, which readily lends itself to automated manufacture, is generally similar to that described in copending U.S. Pat. No. 5,840,071 and includes a base and a stored energy means comprising at least one distendable elastomeric membrane which cooperates with the base to form a fluid reservoir. The fluid flow indicator subassembly is also somewhat similar to that described in U.S. Pat. No. 5,840,071 and comprises a mechanical fluid flow indicator that provides a clear visual indication of normal fluid flow and absence of fluid flow either because the reservoir is empty or because the flow lines are occluded.

As previously mentioned, the apparatus of the invention also includes fill means for use in filling the reservoir of the reservoir assembly which comprises first and second fill assemblies which can be mated with the base of the reservoir assembly for controllably filling the reservoir thereof.

BRIEF DESCRIPTION OF THE DRAWINGS

FIG. 7 is a cross-sectional view taken along lines 7—7 of FIG. 5.

FIG. 8 is an enlarged, cross-sectional view taken along lines 8—8 of FIG. 5.

FIG. 9 is a cross-sectional view taken along lines 9—9 of FIG. 8.

FIG. 22 is a cross-sectional view taken along the horizontal center line of the apparatus shown in FIG. 20 (see lines 22—22 of FIG. 28).

FIG. 25 is a cross-sectional view taken along lines 25—25 of FIG. 22.

FIG. 27 is a cross-sectional view taken along lines 27—27 of FIG. 22.

FIG. 28 is a cross-sectional view taken along lines 28—28 of FIG. 22.

FIG. 29 is a cross-sectional view taken along lines 29—29 of FIG. 22.

FIG. 30 is a cross-sectional view taken along lines 30—30 of FIG. 29.

FIG. 31 is a cross-sectional view taken along lines 31—31 of FIG. 22.

FIG. 32 is a cross-sectional view similar to FIG. 31 but showing the locking pin of the device moved into a locking position.

FIG. 33 is a cross-sectional view taken along lines 33—33 of FIG. 22.

FIG. 45 is a front view of the locking ring component of the medicament dose dialing assembly of the apparatus of the invention.

FIG. 46 is an end view taken along lines 46—46 of FIG. 45.

FIG. 47 is a front view of the vial support component of the apparatus of the invention.

FIG. 48 is a cross-sectional view taken along lines 48—48 of FIG. 47.

FIG. 49 is a side-elevational view of the vial support component.

FIG. 50 is a front elevational view of the adapter advancing component of the medicament dose dialing assembly of the apparatus of the invention.

FIG. 51 is a cross-sectional view taken along lines 51—51 of FIG. 50.

FIG. 52 is a fragmentary cross-sectional view of the advancing teeth formed on the adapter advancing component of the medicament dose styling assembly.

FIG. 53 is a generally diagrammatic plan view illustrating the indicia printed on the be outer surface of the adapter advancing component of the medicament dosing styling assembly of the apparatus of the invention.

FIG. 66 is a cross-sectional view similar to FIG. 64, but showing the container assembly separated from the adapter component.

FIG. 66A is a cross-sectional view taken along lines 66A—66A of FIG. 66.

FIG. 66B is a cross-sectional view taken along lines 66B—66B of FIG. 66.

FIG. 70 is a cross-sectional view of the unfilled field assembly of the apparatus of this latest form of the invention.

FIG. 71 is a view taken along lines 71—71 of FIG. 70.

FIG. 72 is a cross-sectional view of the fill assembly similar to FIG. 70 but showing the fluid reservoir of the fill assembly being filled by a hypodermic syringe.

FIG. 81 is a front view of the plunger component of the apparatus shown in FIG. 77.

FIG. 82 is a cross-sectional view taken along lines 82—82 of FIG. 81.

FIG. 83 is a side elevational view of the connector component of the apparatus to which the plunger shown in FIG. 82 is threadably interconnected, FIG. 84 is a view taken along lines 84—84 of FIG. 83.

FIG. 85 is a view taken along lines 85—85 of FIG. 83.

FIG. 87 is a cross-sectional view taken along lines 87—87 of FIG. 86.

FIG. 89 is a side elevational, cross-sectional view similar to FIG. 88, but showing the adapter sleeve of the assembly advanced into and intermediate position.

FIG. 90 is a side elevational, cross-sectional view similar to FIG. 89 to showing the adapter sleeve of the assembly fully advanced into the housing.

DISCUSSION OF THE INVENTION

Figure 1:
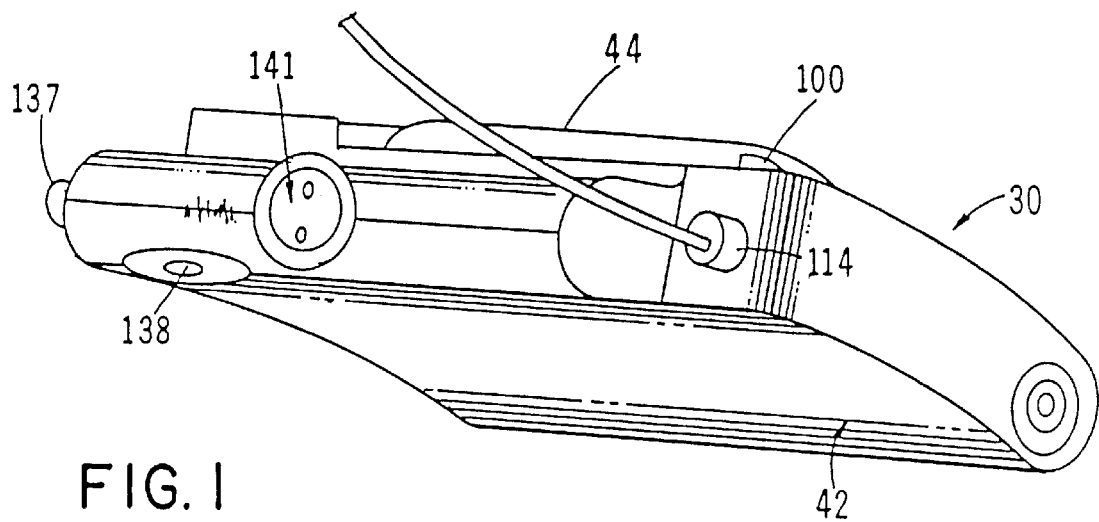
FIG. 1 is a generally perspective bottom view of one form of the infusion device of the present invention.

Referring to the drawings and particularly to FIGS. 1 through 7, one form of the apparatus of the invention for controlled delivery of medicinal fluid flow to a patient is there shown. The apparatus here comprises four major components which are generally designated in FIG. 1 as a hollow housing 30, a fill assembly 32, an adjustable flow rate mechanism 34 and an indicator assembly 36 for indicating fluid flow to the patient. Housing 30 of the apparatus is similar in some respects to that described in U.S. Pat. No. 5,721,382 issued Nov. 24, 1998 in that it includes a base assembly 42, a stored energy means which cooperates with the base assembly to form a fluid reservoir and an indicator assembly which provides a visual indication of fluid flow through the device. Because of the pertinence of U.S. Pat. No. 5,721,382, this patent is incorporated by reference as though fully set forth herein. Also generally pertinent to a complete understanding of the present invention is the apparatus disclosed in U.S. Pat. No. 5,830,187 issued Jun. 18, 1996, this Patent is also incorporated by reference as though fully set forth herein.

Figure 4:
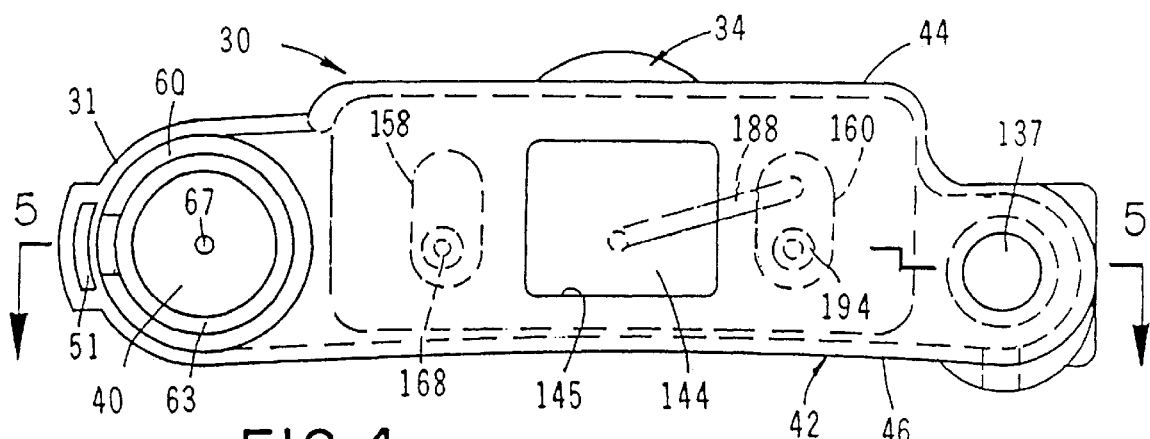
FIG. 4 is a front elevational view of the apparatus of the invention.
Figure 17A:
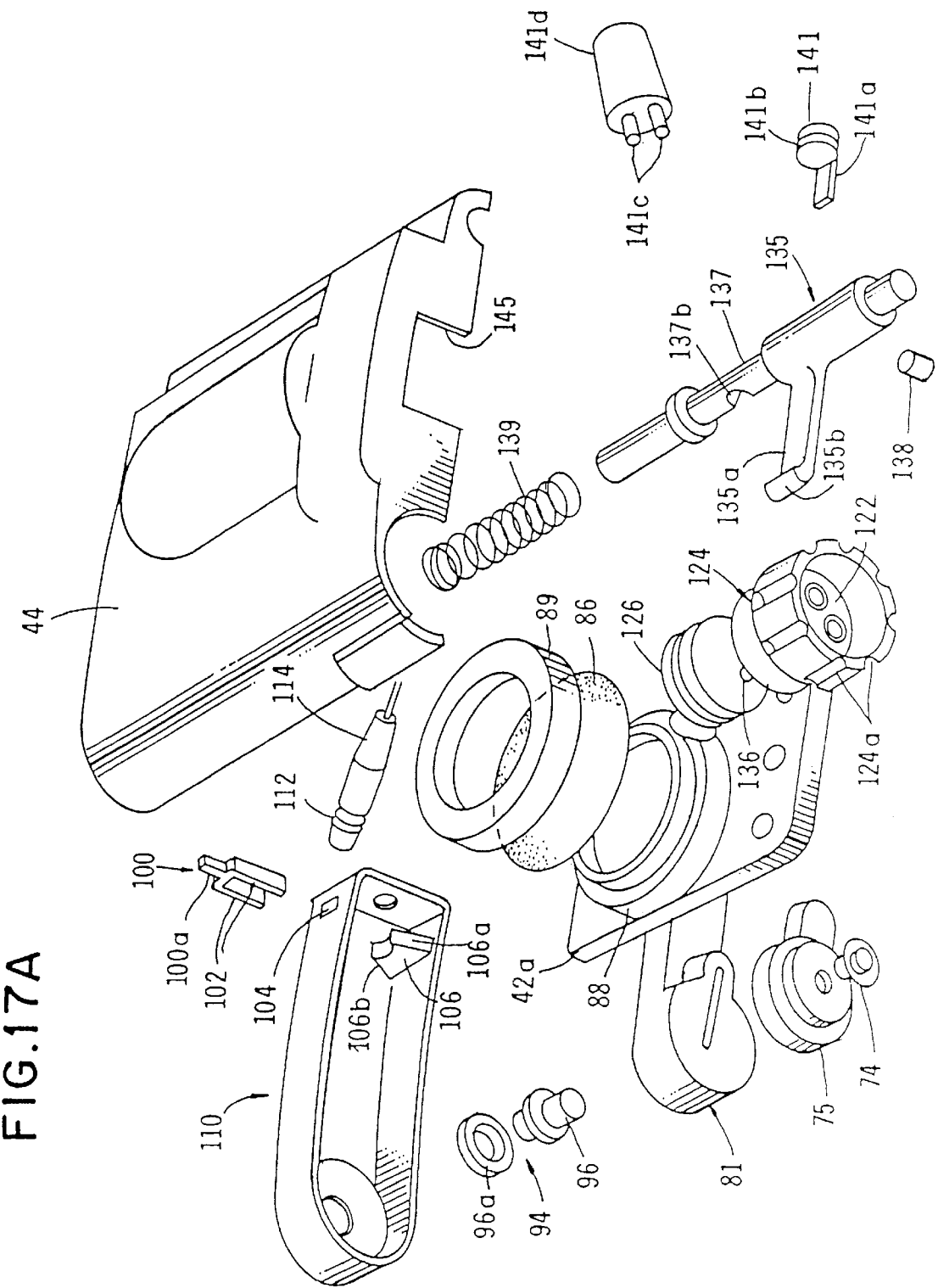
FIG. 17 is a generally perspective exploded view of the apparatus of the present form of the invention showing the appearance and interrelationship among the various component parts of the apparatus.
Figure 17B:
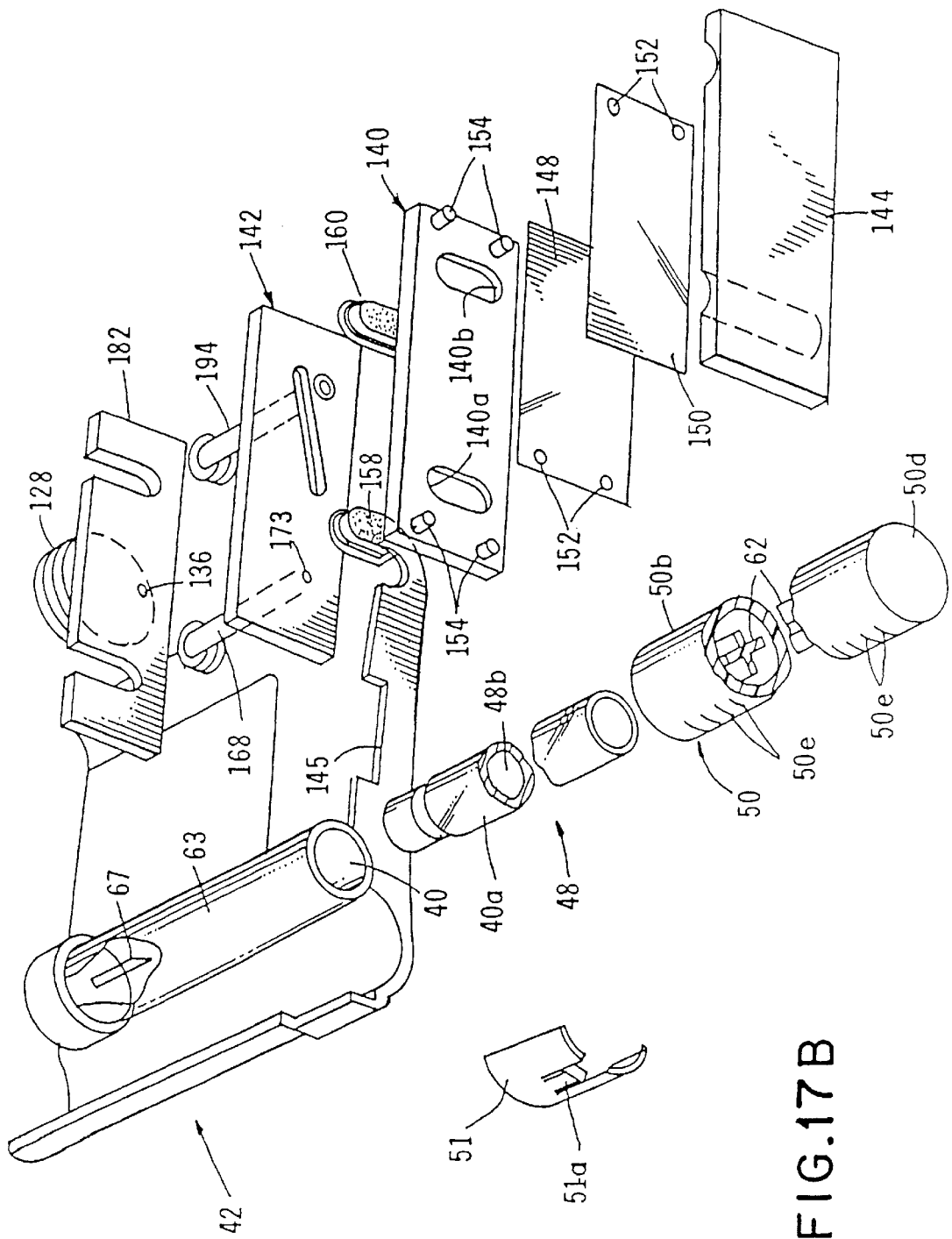

Considering first the hollow housing assembly 30, this assembly is provided with a uniquely configured receiving chamber 40 which is formed between the base assembly 42 and an interconnected cover component 44 (FIGS. 4 and 17). Base assembly 42 and cover component 44, when interconnected, cooperate to define hollow housing assembly 30. In a manner presently to be described, chamber 40 is adapted to telescopically receive the fill assembly of the invention to permit controlled filling of the reservoir of the device with a fluid to be dispensed to the patient.

Figure 19:
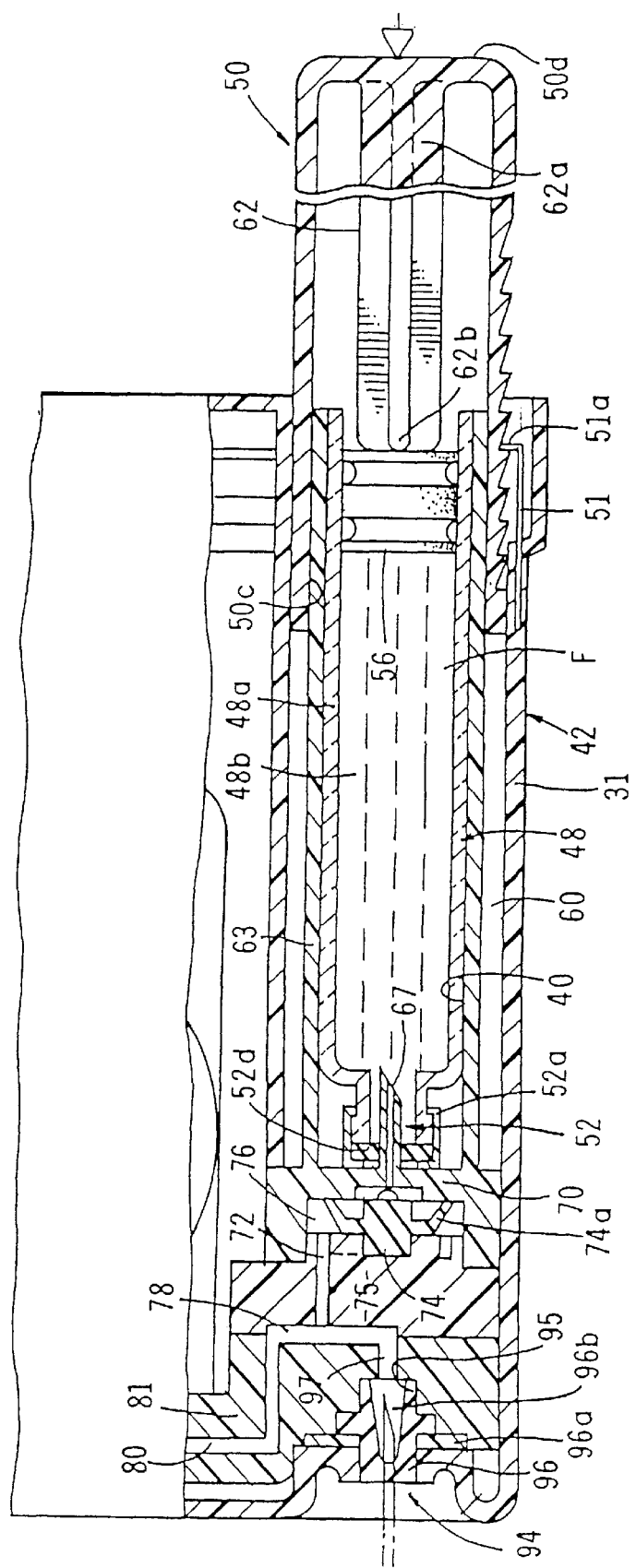
FIG. 19 is a cross-sectional view illustrating the manner of assembly of the fill vial of the apparatus with the housing.

Turning particularly to FIGS. 17 and 19, the fill assembly portion of the apparatus can be seen to comprise a container subassembly 48 and an adapter subassembly 50, the character of which will presently be described. Container assembly 48 includes a body portion 48a having a fluid chamber 48b for containing an injectable fluid "F". Chamber 48b is provided with first and second open ends, one of which is sealably closed by closure means here provided in the form of a pierceable septum assembly 52. Septum assembly 52 is held securely in position by a clamping ring 52a (FIG. 19). As best seen in FIG. 19, a plunger 56 is telescopically movable within chamber 48b of container assembly 48 between first and second locations. As is also shown in FIG. 19 subassembly 50 comprises a hollow housing 50b having a first open end 50c and a second closed end 50d. The adapter assembly 50 is telescopically receivable within an elongated, generally annular passageway 60 formed in device housing 30 in the manner shown in FIG. 19 so that the adapter assembly can be moved from a first extended position into a second vial encapsulation position. The adapter subassembly also includes pusher means shown here as an elongated pusher rod 62 which functions to move plunger 56 within the fluid chamber 48b of the container subassembly. Pusher rod 62 has a first end 62a which is interconnected with closure wall 50d and an opposite end 62b which engages plunger 56 and causes telescopic movement of the plunger forwardly within chamber 49b. Housing 50b includes a plurality of spaced-apart teeth 50d which are lockably engaged by a locking tab 51 a provided on a locking clip 51 (FIG. 17) which is carried by base 42. Those components, which comprise the adapter locking means, cooperate to lock the adapter against removal after it has been fully inserted into the housing.

Figure 6:
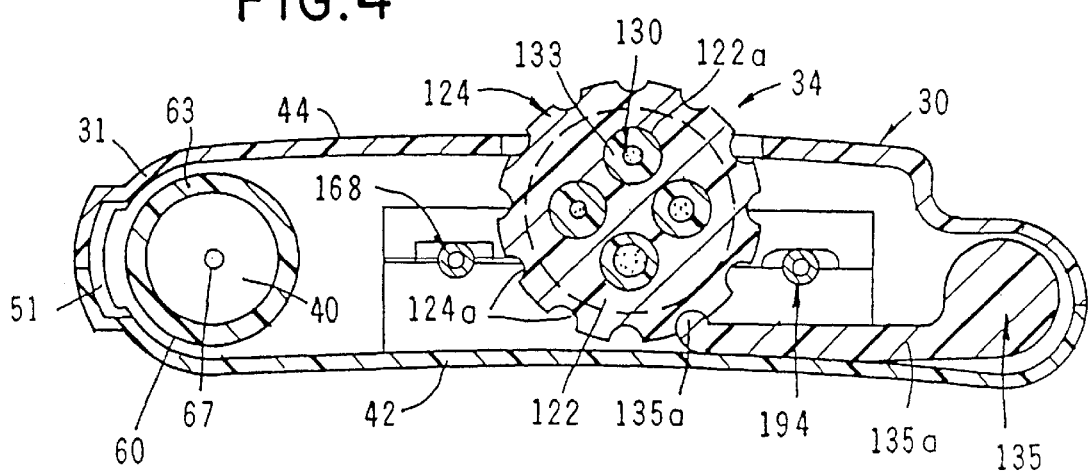
FIG. 6 is a cross-sectional view taken along lines 6—6 of FIG. 5.

As best seen in FIG. 19, provided within housing 30 is an elongated, generally cylindrically shaped wall 63 which is concentric with the outer housing wall which defines receiving chamber 40. Wall 63 is radially spaced from the outer wall 31 of the housing so as to define the longitudinally extending annular space 60 (FIGS. 6 and 19). With this construction, during the mating of the reservoir fill assembly with the base assembly, the outer wall of the housing 50 is closely received within space 60 as the adapter subassembly is urged inwardly or forwardly of the device housing 30. At the same time that hollow housing 50 moves forwardly of annular space 60, the container assembly telescopically moves inwardly so as to move septum 52d of septum assembly 52 into piercing engagement with a hollow cannula 67 which is connected to a base wall 70 so that it extends inwardly into chamber 40 (see FIG. 5).

As plunger 56 of the container assembly is moved forwardly of container 48a by pusher rod 62, the fluid contained within the container will flow under pressure into a passageway 72 via a hollow cannula 67 and via a valve means, shown here as an umbrella type check valve 74. Check valve 74 is disposed within a cavity 76 formed in housing 30 in the manner shown in FIG. 5. Valve 74 is constructed from an appropriate elastomer and has a resiliently deformable skirt portion 74a which will deform inwardly within cavity 76 to permit fluid flow toward the reservoir of the device, but will block reverse flow. From passageway 72, the fluid will flow into a passageway 78, then into passageway 80 formed in a manifold 81, and finally into reservoir 82 via a passageway 84. As a fluid flows into reservoir 82 it will cause the stored energy means or membrane 86 (FIG. 7) to extend outwardly from an ullage substrate 88a formed in a base platform 88 which comprises a part of the base assembly 42 (FIG. 7). As best seen in FIG. 7, ullage substrate 88a is specially configured to receive a membrane clamping ring 89 which mates with ullage substrate 88a in a manner shown in FIG. 7 to clamp membrane 86 about its periphery 86a. With this construction, distendable membrane is securely clamped in position with cover 44 overlaying ullage substrate 88a and membrane 86 in a manner to sealably enclose the assembly within the hollow housing portion of the device.

After the reservoir has been filled and as membrane 86 moves toward substrate 88a during the fluid dispensing step, fluid within reservoir 82 will be uniformly and controllably forced outwardly through a passageway 84 and then on toward the important flow control means of the invention.

Figure 3:
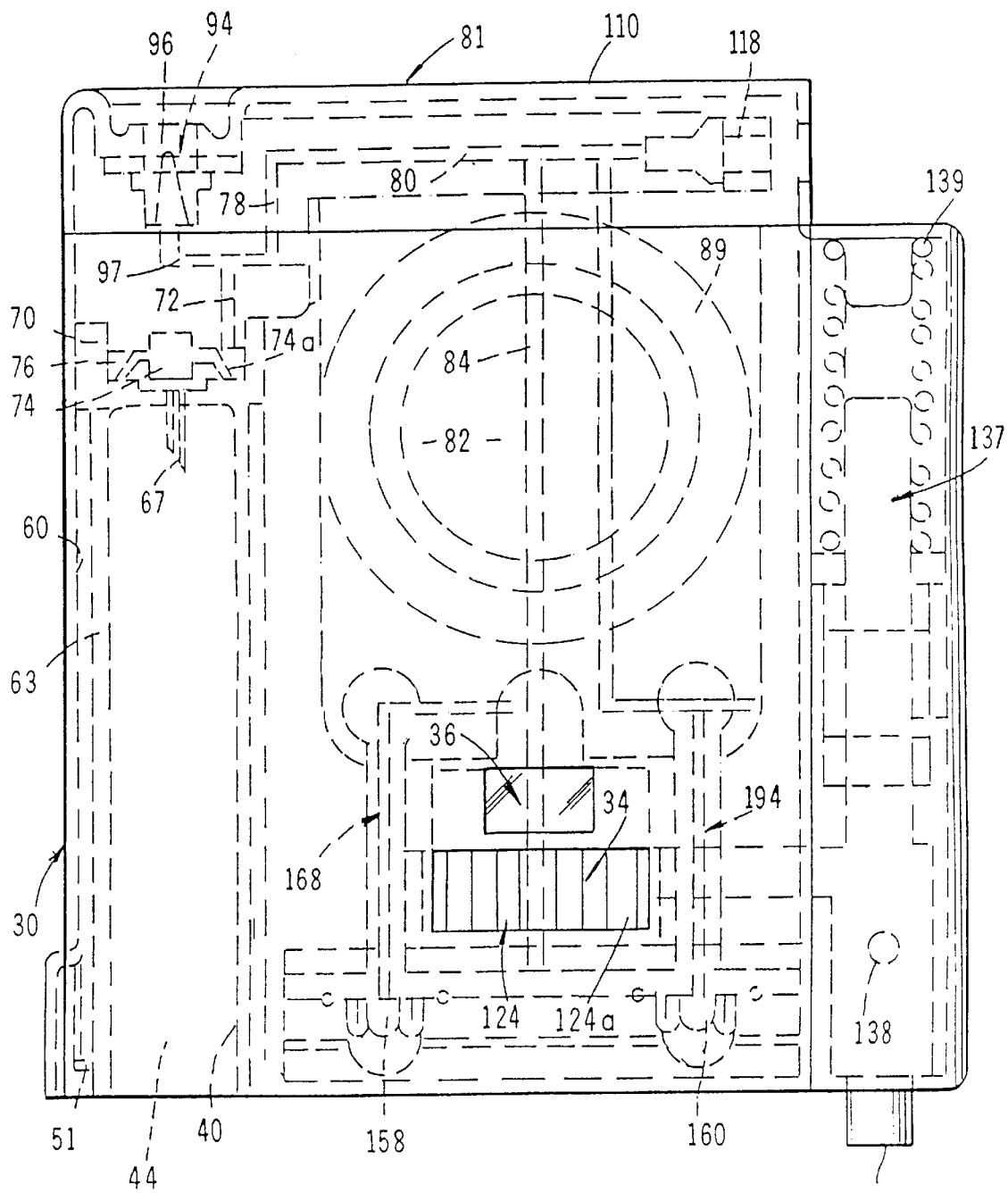
FIG. 3 is a top plan view of the apparatus shown in FIG. 1.
Figure 5:
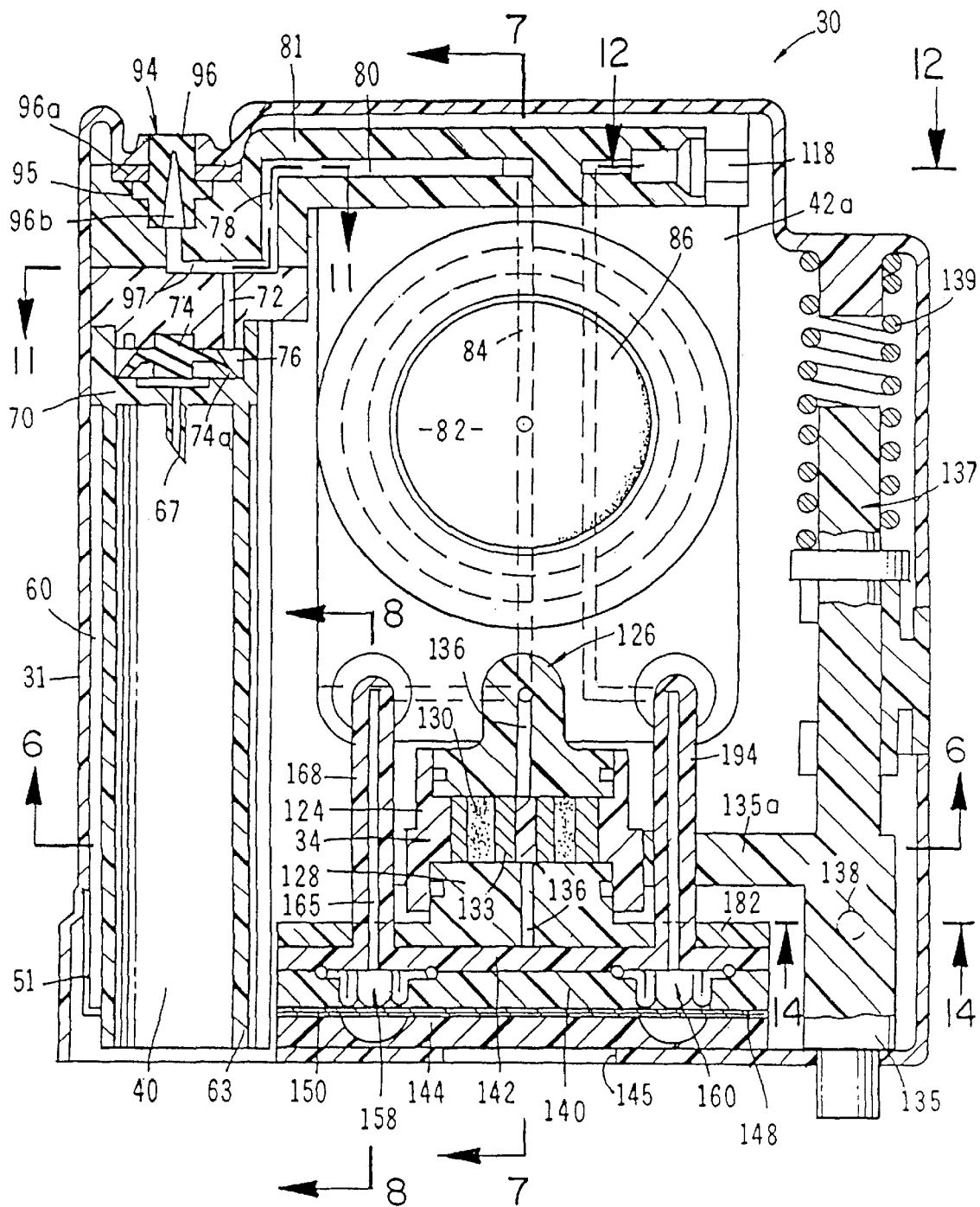
FIG. 5 is a cross-sectional view taken along lines 5—5 of FIG. 4.
Figure 10:
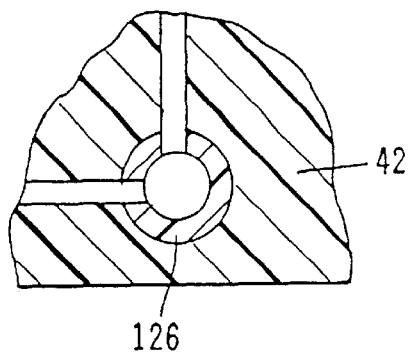
FIG. 10 is an enlarged, cross-sectional view taken along lines 10—10 of FIG. 7.
Figure 11:
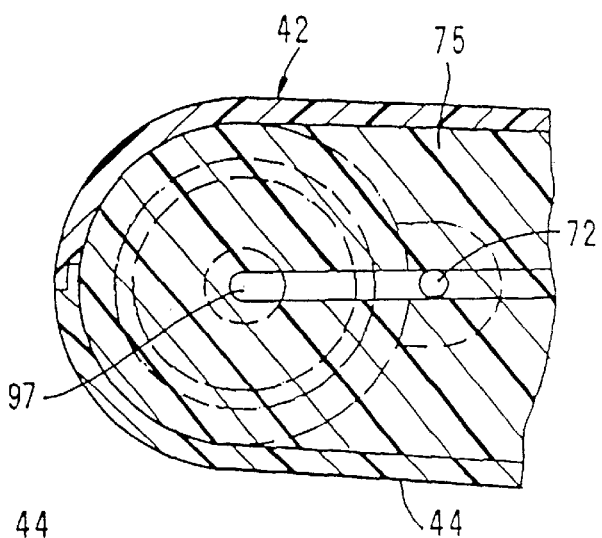
FIG. 11 is an enlarged, cross-sectional view taken along lines 11—11 of FIG. 5.
Figure 12:
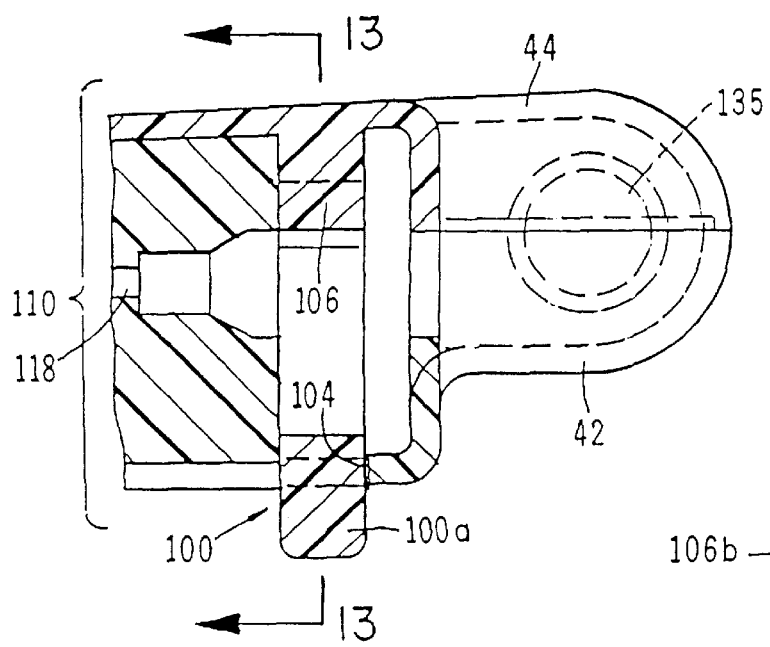
FIG. 12 is an enlarged cross-sectional view taken along lines 12—12 of FIG. 5.

As illustrated in FIGS. 3 and 5, the embodiment of this latest form of the invention also includes a uniquely designed fluid recovery means mounted within manifold 81. As indicated in FIGS. 5 and 17, manifold 81 is connected to ullage substrate 88a and is in communication with reservoir 82 so that fluid can be recovered as may be desired from reservoir 82. This novel recovery means here comprises a recovery septum assembly 94 which is mounted within a cavity 95 formed in manifold 81. Septum assembly 94 includes a septum retainer ring 96a (FIG. 17) and a pierceable elastomeric septum 96 of generally conventional design. Septum 96 includes an internal chamber 96b which is in communication with a fluid passageway 97 which, in turn, communicates with reservoir 82 via passageways 78, 80 and 84. Septum 96 is pierceable by the cannula of a conventional syringe so that, as desired, fluid can be readily recovered from reservoir 82 using a conventional syringe.

Figure 13:
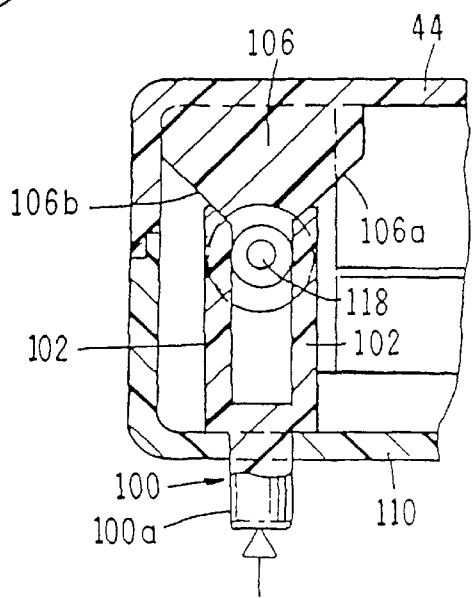
FIG. 13 is a cross-sectional view taken along lines 13—13 of FIG. 12.

Turning particularly to FIGS. 13 and 17, the novel delivery line interconnection and release means of the invention is there illustrated. This means functions to releasably interconnect the delivery assembly, which is of the character shown in FIGS. 1 and 17 to housing 30. This novel interconnection and release means here comprises a push button subassembly 100, which includes a head portion 100a and a pair of yieldably deformable legs 102 (FIG. 13). A part of head portion 100a extends through an aperture 104 formed in closure component 110 in the manner shown in FIG. 13 so that the deformable legs 102 engage the ramp sides 106a and 106b of a ramp unit 106 (FIG. 17). Ramp unit 106 is connected to the base portion of a closure component 110 which closes the back end of housing 30. Each of the legs 102 of the push button subassembly lockably engages a shoulder 112 provided on the delivery fitting 114 (FIG. 17) when the push button subassembly is in an upward, at-rest position. It is apparent that a downward force exerted on head portion 100a will cause legs 102 to move downwardly along rampsides 106a and 106b causing legs 102 to spread apart a sufficient distance to clear shoulder 112 so as to permit withdrawal of delivery fitting 114. When the delivery line is connected to the housing in the manner described, fluid can flow from reservoir 82 outwardly of the device via a novel flow rate control means, the character of which will next be described.

Figure 15:
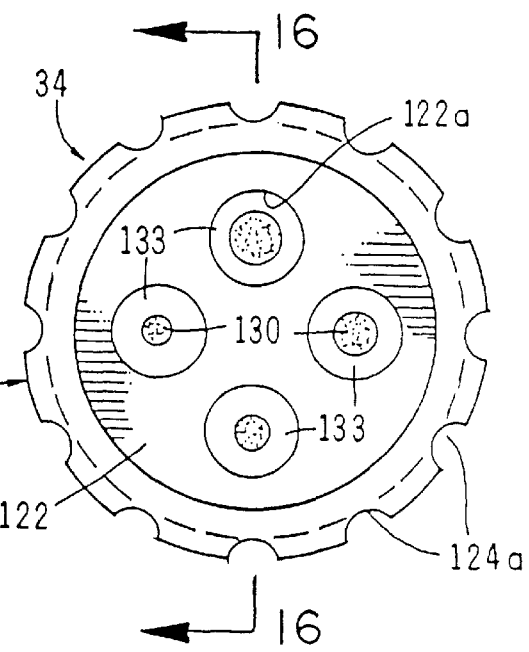
FIG. 15 is a front-elevational view of one form of the control member of the adjustable rate control means of the invention.
Figure 16:
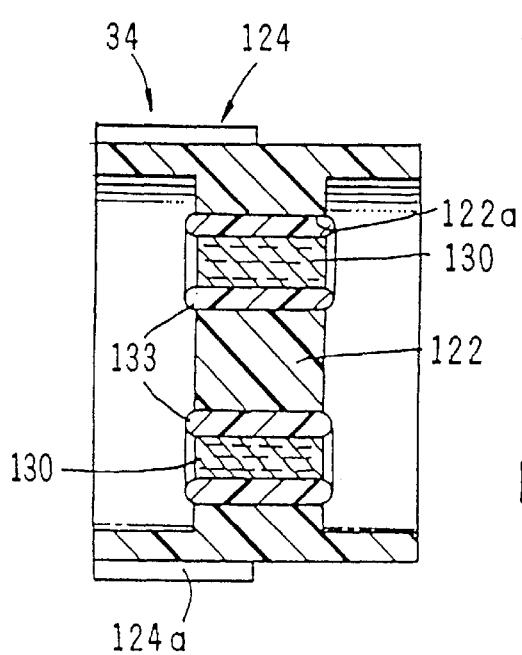
FIG. 16 is a cross-sectional view taken along lines 16—16 of FIG. 15.

The flow rate control means is a very important feature of the apparatus of the invention and functions to adjustably control the rate of fluid flow from the reservoir 82 of the apparatus to the device outlet passageway 118. This novel means here comprises the previously mentioned adjustable rate control mechanism 34 which is carried by housing 30. As best seen in FIGS. 6, 15, and 16, mechanism 34 includes a central body portion 122 which is disposed internally of a knurled control knob 124. Knob 124 is rotatably supported by members 126 and 128 which are mounted internally of housing 30 (FIG. 17). O-rings carried by members 126 and 128 sealably engage control knob 124 and prevent fluid leakage among the various cooperating components.

Figure 18A:
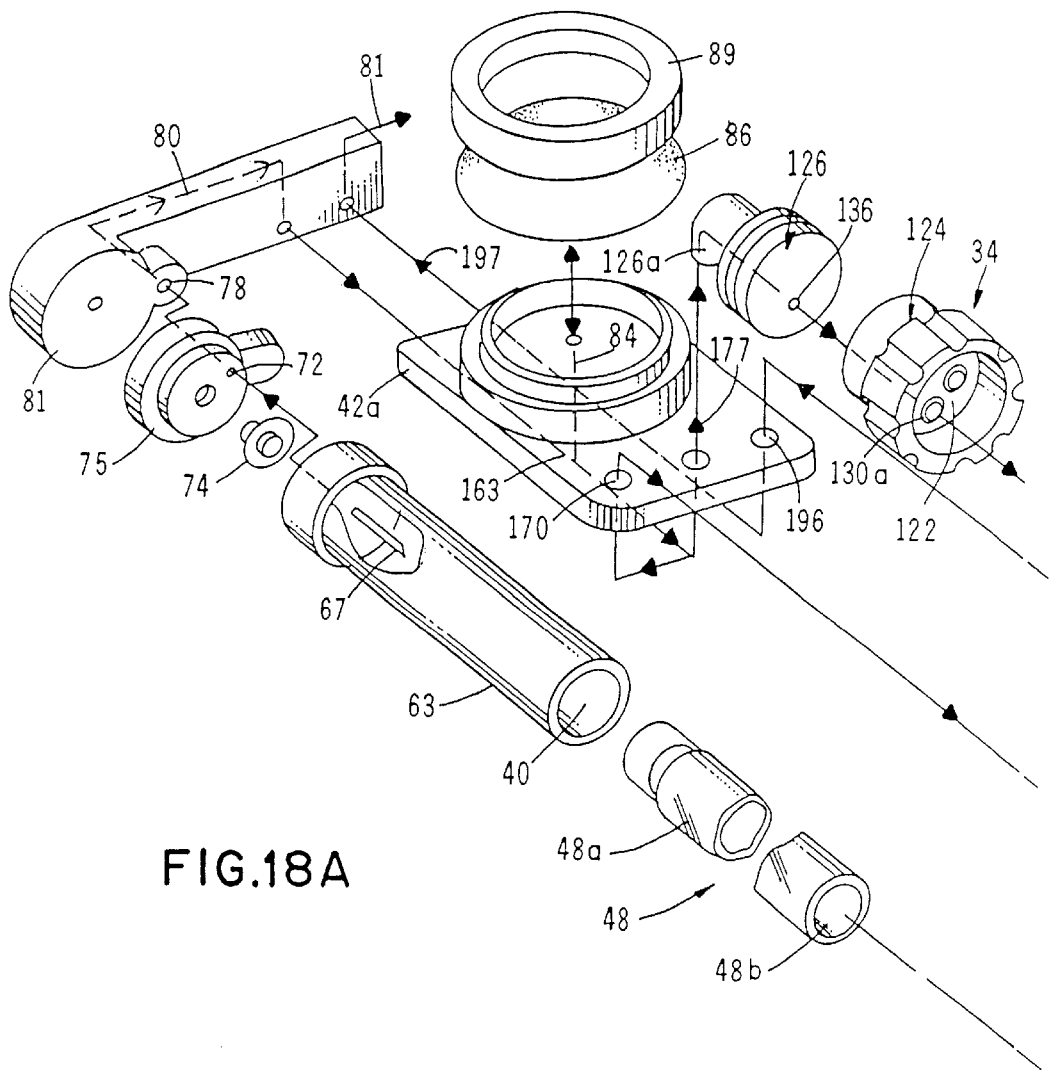
FIG. 18 is a generally perspective, exploded view similar to FIG. 17 and showing the fluid flow paths through the apparatus.
Figure 18B:
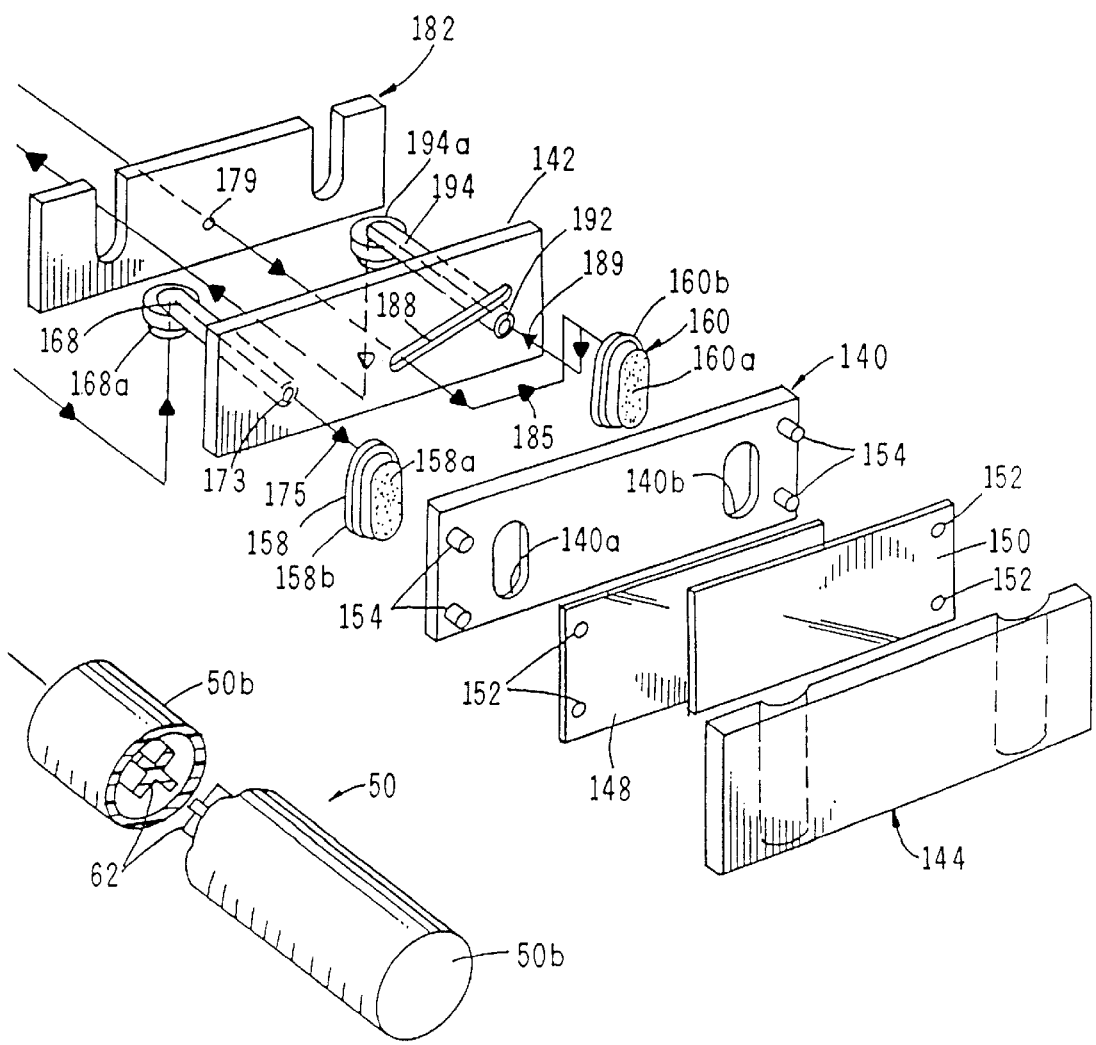

As best seen in FIGS. 15 and 16, central body portion 122 carries a plurality of circumferentially spaced apart flow restrictors. By rotating knob 124, each of the flow restrictors can be selectively moved into index with the flow passageways which carry the fluid from reservoir 82 to the outlet of the device. In the embodiment of the invention shown in the drawings, the flow restrictors are provided in the form of rate control frits 130 (see FIGS. 15 and 16), which are secured in place within apertures 122a formed in body 122 by a moldable elastomer 133 (see FIG. 16). With the construction shown, by rotating knob 124 relative to housing 30, each of the rate control frits 130 can be moved sequentially into alignment with a fluid passageway 136 which extends through members 126 and 128 (FIGS. 17 and 18). Because each of the frits 130 is of a different, preselected porosity, it is apparent that the rate of fluid flowing outwardly of the device through outlet passageway 118 can be precisely controlled by positioning a particular frit in the flow path.

Figure 14:
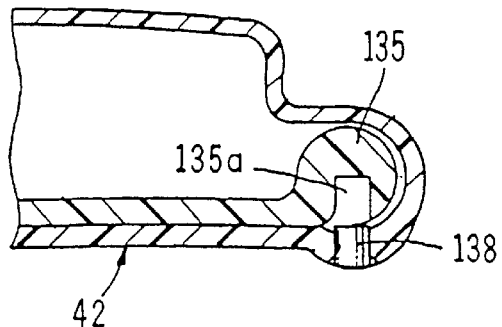
FIG. 14 is a cross-sectional view taken along lines 14—14 of FIG. 5.

An important feature of the invention is the rate control lock-out means which locks knob 124 against rotation This lock-out means here comprises a locking member 135 which is mounted on an elongated push rod 137 that is carried by base 42 for movement between a first extended locking position and an inward position. Extending from locking member 135 is a locking tab 135a which is movable into and out of locking engagement with channels 124a provided on knob 124 by movement of rod 137 between its first and second positions. A rod biasing means, here provided as a coil spring 139 which is carried within the device housing functions to continuously bias push rod 137 toward its second extended knob engaging locked position. As shown in FIG. 17, rod 137 can be locked in the extended locked position by a lock means here provided as a generally cylindrical shaped rotatable member 141. Member 141 has a stem portion 141a which can be rotated into and out of locking engagement with a notch 137b formed in rod 137. The head portion 141b of member 141 has spaced apart spanner holes which receive spanner pins 141c provided on the physician key 141d which is of the character shown in FIG. 17. Disabling means for disabling the device is here provided in the form of a disabling button 138 (FIGS. 14 and 17) which is carried by base 42. Button 138 can be pushed into a cavity 135a in member 135 so as to prevent its movement and thereby disable the device.

Another unique feature of the apparatus of the invention is a novel flow indicator means which functions to distinguish among three conditions of operation of the device, namely normal fluid flow, blockage or occlusion, and reservoir empty, Turning particularly to FIG. 17, this novel flow indicator means here comprises an indicator base or platform 140 and a boot clamping plate 142. Additionally, the indicator means comprises a support or lens plate 144. Platform 140, clamping plate 142 and support plate 144 are all enclosed within housing 30 to in the manner indicated in FIG. 17. When the components are positioned within housing 30, plate 144 is viewable through an aperture 145 provided in housing 30 (see also FIGS. 5 and 7).

Disposed between lens plate 144 and platform 140 are first and second indicia-carrying means shown here as a pair of closely adjacent, thin films 148 and 150. Films 148 and 150, are in intimate contact and are preferably constructed from a substantially transparent, flexible polymer material such as mylar. It is to be understood that the indicia-carrying means need not be thin films, but rather can be any type of surface presenting member upon which indicia can be provided. The downstream surface of the inferior or first film 148 is printed with three integrated symbols (see FIGS. 4,6, and 8 of incorporated by reference U.S. Pat. No. 5,721,382, which may comprise, by way of example, a blue circle, a green arrow, and a red cross, each consisting of diagonal strips of color printed in an alternating pattern (blue, green, red, blue, green, red, and so on). The second film 150 serves as a "mask" over film 148 and is printed with a pattern of diagonal alternating clear and opaque strips that occur in approximately a 1:2 ratio. The printed ratio of the "mask" allows only one colored symbol to appear at a time when viewed through viewing lens plate 144. The inferior and superior films are provided at their opposite ends with apertures 152 which receive retention pins 154 provided on platform 140 (FIG. 17) which permit attachment of the film to platform 140 in a manner such that the non-patterned portions of each film covers boot openings 140a and 140b provided proximate each end of platform 140 with the patterned portions of both the superior and inferior films being maintained in index. With this construction, each thin film is able to move in response to pressure exerted thereon by the actuating means of the invention, the character of which will presently be described, in opposing directions parallel to the film plane with its range of motion limited to one axis in the film plane. As the films move, the visible symbol pattern will, of course, change due to the transverse displacement of the patterns imprinted thereon.

As will be discussed in greater detail hereinafter and as is apparent from a study of FIGS. 17 and 18, the central portions of both the first and second elastomeric actuator elements or boots 158 and 160, which here comprise the actuator means of the invention, will be deflected outwardly in a direction toward plate 144 when the device is filled and primed, but not in a state of delivery or when there is a build up of fluid pressure during delivery that is caused by blockage of the delivery line downstream from boot 158. While boot 158 can be deflected by normal line pressure, boot 160 is deflected only by pressure buildup resulting from the downstream blockage (see FIG. 18). When both elastomeric boots 158 and 160 are deflected outwardly, both the superior and inferior films are displaced transversely to a second position revealing a second symbol, as for example, an X as viewed through the viewing aperture of the support plate (see also FIGS. 35 and 36 of U.S. Pat. No. 5,721,382 which is incorporated herein by reference).

A third alignment of symbol patterns as shown in FIG. 32 of U.S. Pat. No. 5,721,382 is visible when the device is in an unfilled state or when the delivery line is open, the reservoir is empty and fluid delivery of the patient has been completed. In this case, there is no fluid pressure in the line on either the upstream or the downstream side of the flow control means and thus both the first and second boots are in a non-deflected position. In this condition, the inferior and superior films are not transversely displaced and thus exhibit a third combination of patterns resulting in a third symbol as, for example, a circle being visible through the viewing aperture of the support plate. Boots 158 and 160 can be precisely tailored to deflect under various pressures thereby permitting great apparatus versatility.

During the fluid dispensing step, when fluid is forced through reservoir outlet 163 by the stored energy means, the fluid will flow into a passageway 165 formed in a first base connector element 168 which has a connector head 168a that fits into a first socket 170 formed in base platform 42a. Next, the fluid will flow through an aperture 173 formed in plate 142 and finally into a chamber formed in the distendable, elastomeric first boot 158 of the flow indicator means of the invention. Boot 158 includes a yieldably distendable fluid flow blocking body portion 158a which is circumscribed by a marginal portion 158b. Marginal portion 158b is clamped between plate 142 and platform 140 so that the boot extends through opening 140a formed in platform 140. It is to be understood that, when the fluid flowing from reservoir 82 in the direction of the arrow 175 of FIG. 18 impinges upon boot 158, the central portion of the boot will be deflected outwardly into pressural engagement with indicator film 148.

Fluid flowing from reservoir 82 will also flow in the direction of arrow 177 (FIG. 18) into a stub passageway 126a formed in member 126 and then through aperture 136 formed in member 126. After flowing through aperture 136, the fluid will flow through the flow restrictor that is aligned with aperture 136. (This flow restrictor is identified in FIG. 18 by the numeral 130a. Next, the fluid will flow into through an aperture 136 formed in a knob support platform 182 which is connected to base platform 42a. The fluid will then be diverted in the direction of arrow 185 of FIG. 18 into a passageway 188 formed in plate 142.

Next, the fluid will flow from passageway 188 into a chamber 160a formed in elastomeric, distendable boot 160 which also forms a part of the indicator means of the invention. The periphery 160b of indicator boot 160, which is of identical construction to boot 158, is clamped within opening 140b formed in platform 140. After impinging on boot 160, the fluid will next flow back toward plate 142 in the direction of arrow 189, through an orifice 192 formed therein and into a second base connector element 194 which has a base connector head 194a that fits into a socket 196 formed in base platform 42a. From connector element 194, the fluid will flow in the direction of arrow 197 toward the outlet port 118 of the device (FIG. 18).

It is to be observed that fluid flowing from reservoir 82 into passageway 196, and then on toward boot 160 is under a lower pressure than fluid flowing toward boot 158. This is because the pressure of the fluid flowing toward boot 160 has been reduced as a result of the fluid flowing through the adjustable rate control means of the invention. As is more fully discussed in incorporated by reference U.S. Pat. No. 5,721,382, this result enables a determination of the various fluid flow operating conditions of the device namely normal fluid flow, fluid flow blockage or occlusion, and reservoir empty.

Figure 2:
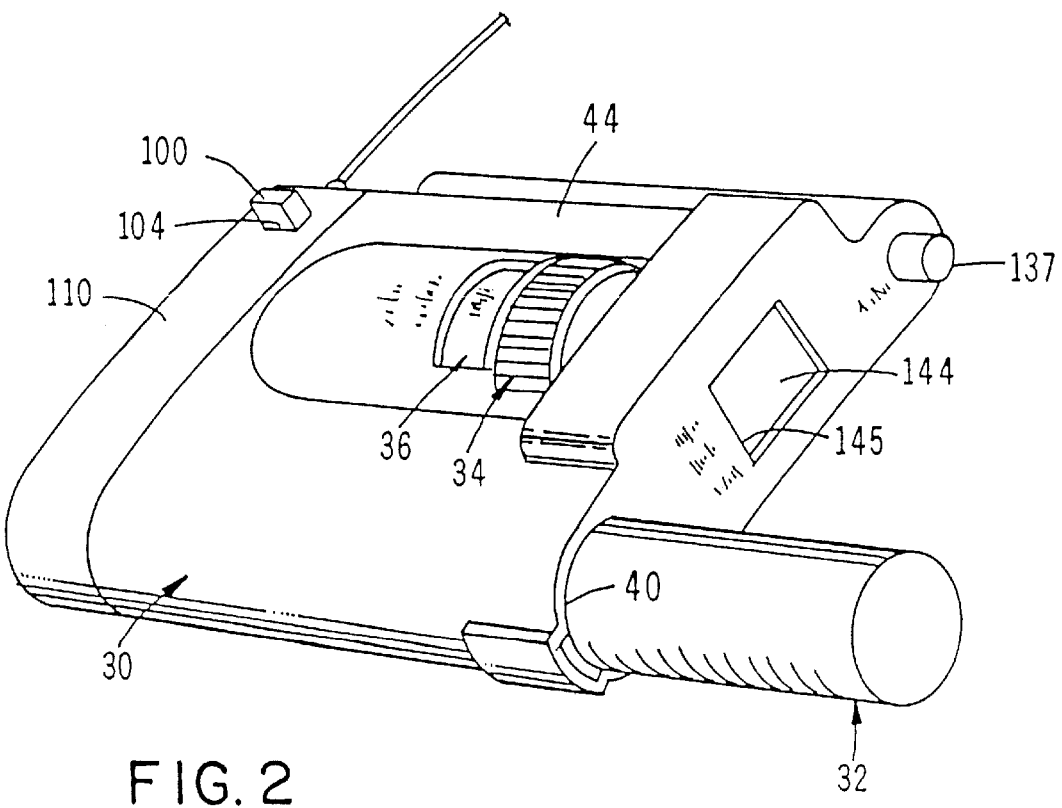
FIG. 2 is a generally perspective top view of the infusion device shown in FIG. 1.

In addition to boots 158 and 160 the flow indicator means also comprises the earlier identified lens 144, which along with platform 140 and support plate 142 are enclosed within housing 30. As best seen in FIG. 2, the viewing lens 144 is viewable through an opening 145 provided in the forward wall.

In using the apparatus of the invention and after the reservoir had been filled using the fill means, the flow rate control means is set to the desired rate of fluid flow. This is done by rotating locking member 141 using a spanner type physician's key. When tab 141*a* is rotated out of locking engagement with notch 137*b*, push rod 137 can be pushed forwardly moving the extremity 135*b* of tab 135*a* out of engagement with one of the finger engaging channels 124*a* formed in knob 124 so as to permit rotation of the knob. After the knob has been rotated by the care giver to bring the appropriate rate control frit 130 into index with the fluid flow passageway, the push rod can be released so that spring 139 will urge the locking tab once more into locking engagement with knob 124. By then rotating member 141 to its locked position and removing the spanner type physician's key from head portion 141*b*, no further adjustment can be made to the rate control means.

Turning now to FIGS. 20 through 34, an alternate form of the apparatus of the invention for controlled delivery of medicinal fluid flow to a patient is there shown and generally designated by the numeral 200. The apparatus is similar in many respects to that shown in FIGS. 1 through 19 and like numerals are used to identify like components. The apparatus here comprises five major components which include a hollow housing, a fill assembly, an adjustable flow rate mechanism and an indicator assembly for indicating fluid flow to the patient. Housing 202 of the apparatus is quite similar to that shown in FIGS. 1 through 19 and includes a base assembly 204, a stored energy means which cooperates with the base assembly to form a fluid reservoir and an indicator assembly which provides a visual indication of fluid flow through the device. The device housing also carries the important dosing means, the character of which will presently be discussed.

Figure 20:
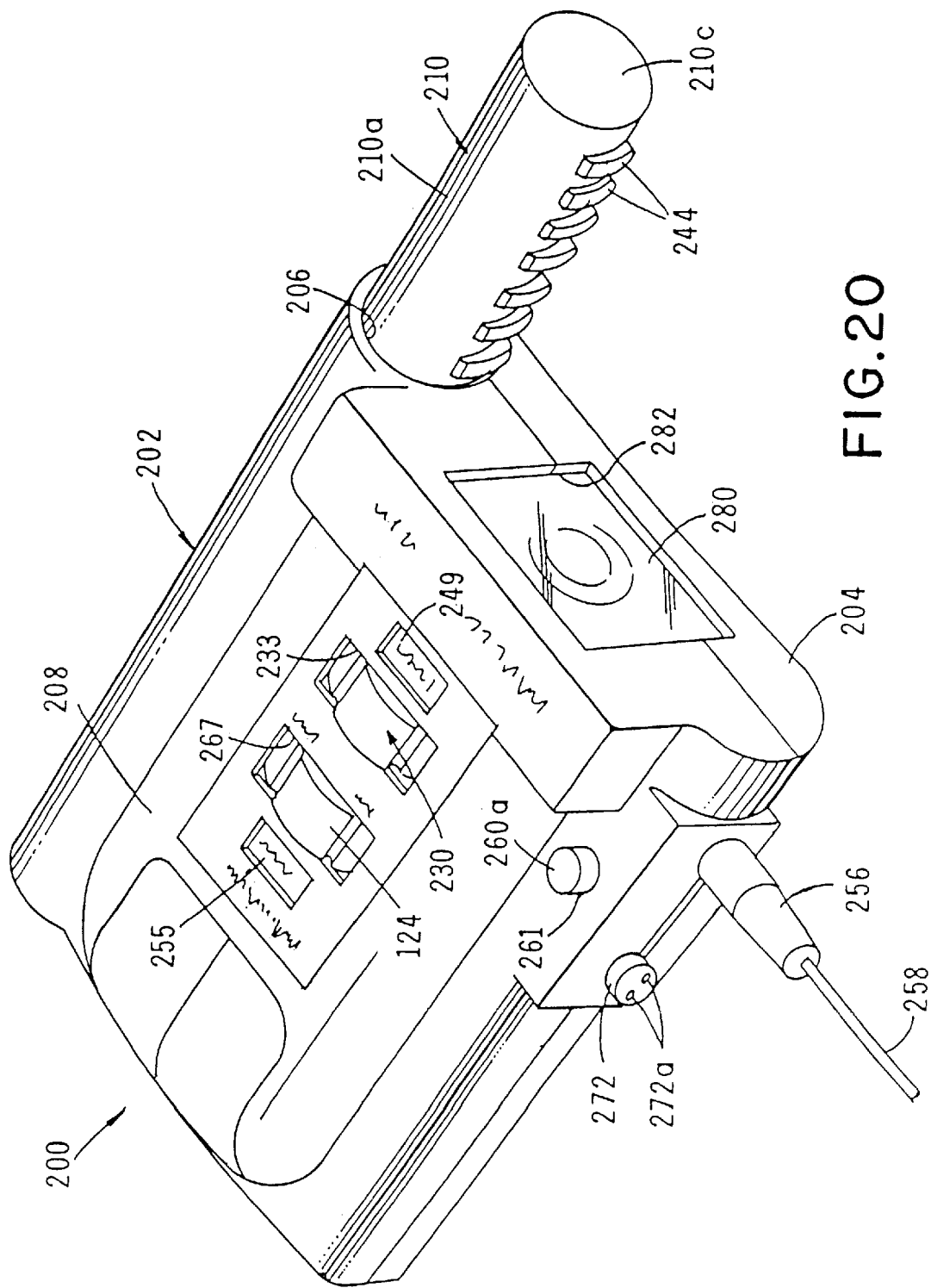
FIG. 20 is a generally perspective view of an alternate form of the infusion device of the present invention.
Figure 21B:
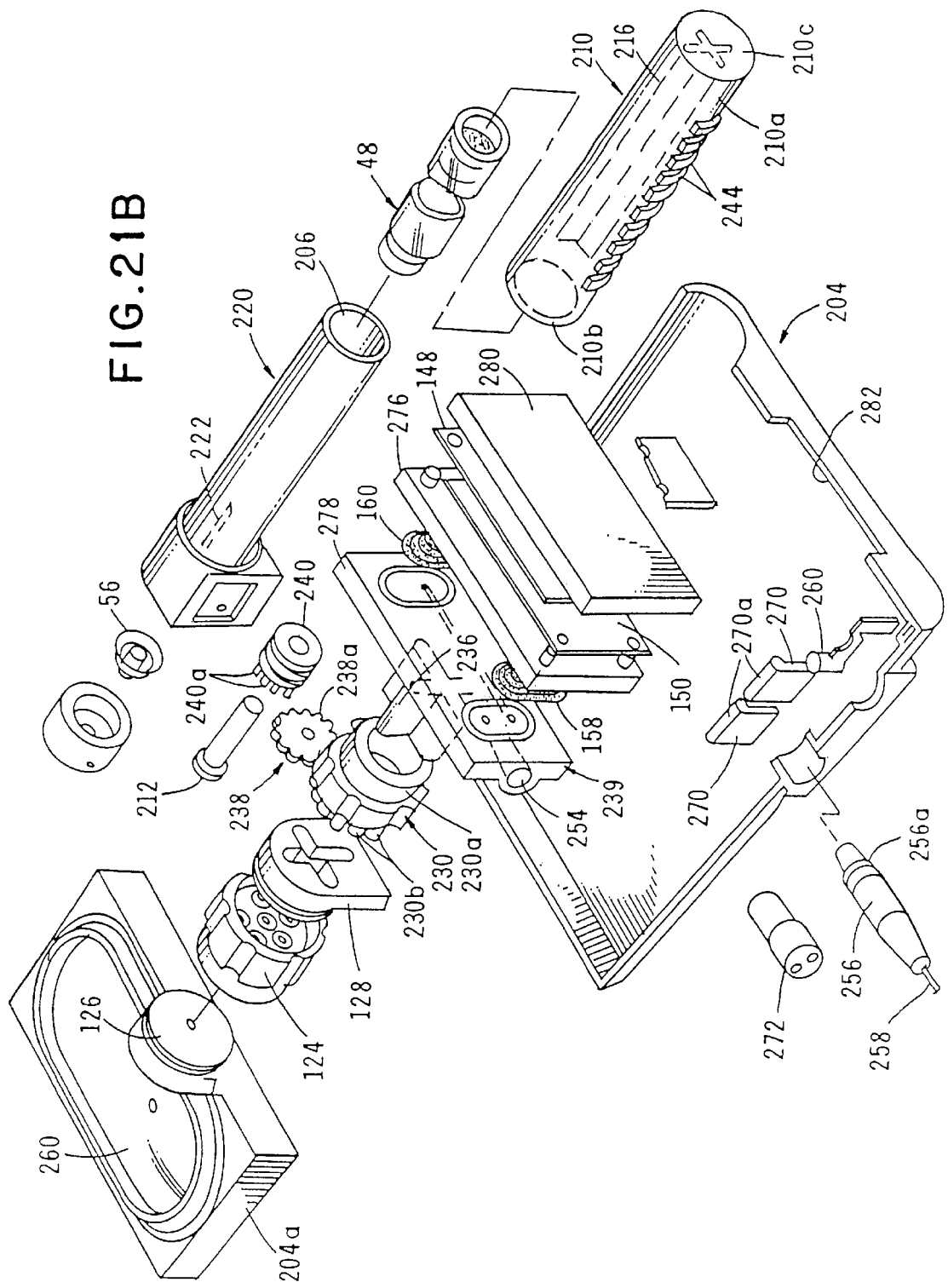
FIG. 21 is a generally perspective exploded view of the infusion device shown in FIG. 20.
Figure 23:
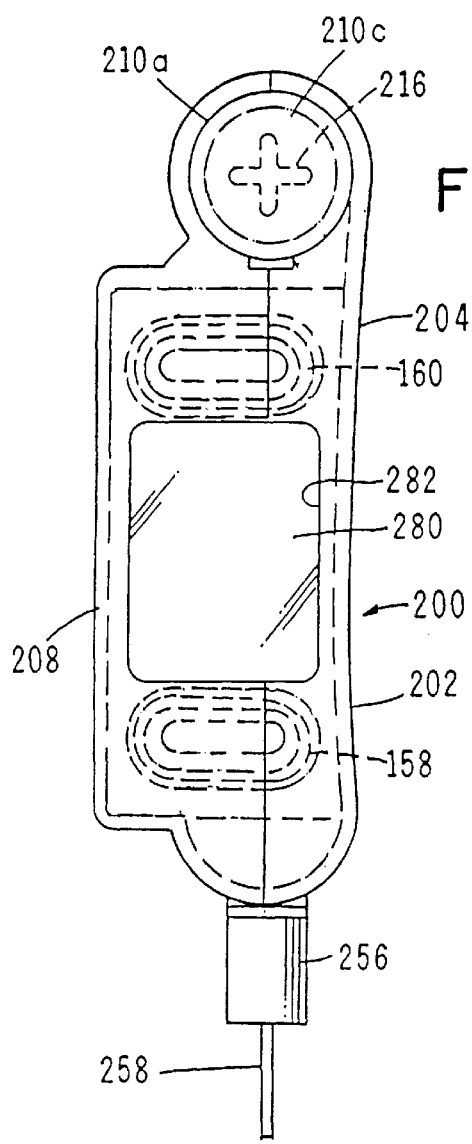
FIG. 23 is a front view of the apparatus shown in FIG. 20.
Figure 24:
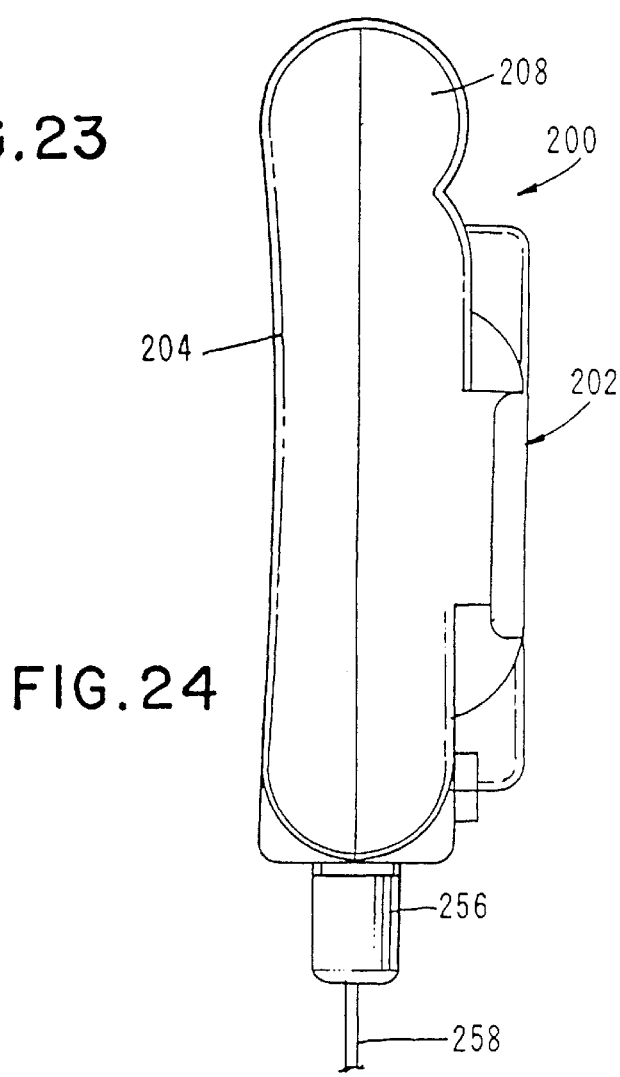
FIG. 24 is a rear view of the apparatus shown in FIG. 20.
Figure 26:
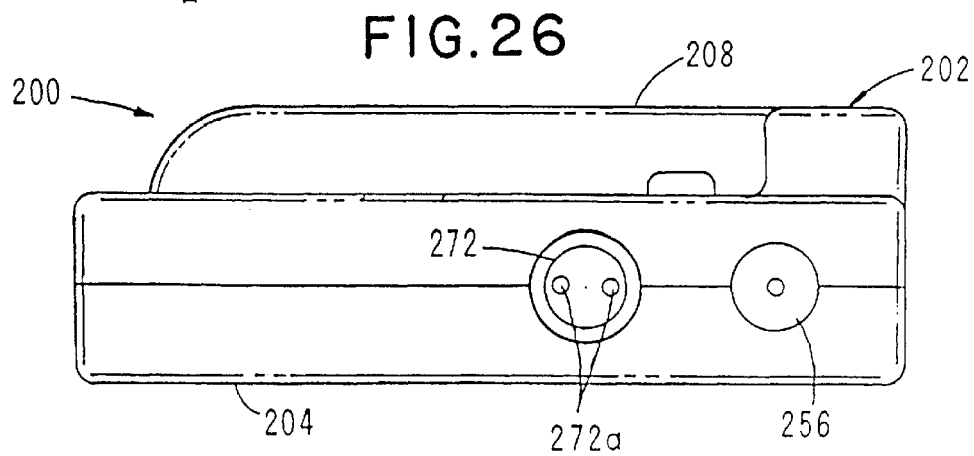
FIG. 26 is a left side view of the apparatus shown in FIG. 20.

Considering first the hollow housing assembly 202, this assembly is here provided with a uniquely configured receiving chamber 206 which is formed between the base assembly 204 and an interconnected cover component 208 (FIGS. 20 and 21). As before, base assembly 204 and cover component 208 when interconnected, cooperate to define the hollow housing assembly 202. In a manner presently to be described, chamber 206 is adapted to controllably receive the fill assembly of the invention to permit controlled filling of the reservoir of the device and the controlled dispensing of the medicament to the patient.

Turning particularly to FIGS. 21 and 22 the fill assembly portion of the apparatus can be seen to comprise a container subassembly 48, which is of identical construction to that previously described, and an adapter subassembly 210, which is of a slightly different configuration. As before, a plunger 56 is telescopically movable within chamber 48*b* of container assembly 48 between first and second locations. As best seen in FIG. 22 adapter assembly 210 comprises a hollow housing 210*a* having a first open end 210*b* and a second closed end 210*c*. The adapter assembly 210 is telescopically receivable within an elongated, generally annular passageway 214 formed in device housing 202 in the manner best seen in FIG. 22 so that the adapter assembly can be moved from a first extended position shown in FIGS. 20 and 22 into a second fluid dispensing position. As was the case with adapter subassembly 50, adapter assembly 210 also includes pusher means shown here as an elongated pusher rod 216 which functions to move plunger 56 within the fluid chamber 48 of the container subassembly upon operation of the dose control means of the invention.

As best seen in FIG. 22, provided within device housing 202 is an elongated, generally cylindrically shaped wall 220 which is concentric with the outer device housing wall which defines receiving chamber 206. Wall 220 is radially spaced from the outer wall 203 of the housing so as to define the previously mentioned longitudinally extending annular space 214 (see also FIG. 25). With this construction, during the mating of the reservoir fill assembly with the base assembly, the outer wall of adapter assembly 210 is closely received within space 214 as the adapter subassembly is urged inwardly or forwardly of the device housing by means of the dose control means. When the adapter assembly is originally mated with the device housing in the manner shown in FIG. 22, the container assembly will be moved telescopically inwardly to move septum 52*a* of septum assembly 52 into piercing engagement with a hollow cannula 222 which extends inwardly into chamber 206 (see FIG. 21).

Once the fluid flow path between the hollow cannula 222 and the fluid reservoir 224 of the apparatus is thus created via a passageway 226 (FIG. 22), an inward movement of the adapter subassembly can be accomplished using the novel dose control means of the invention. As the operating mechanism of the dose control means controllably moves the adapter subassembly inwardly, pusher rod 216 will move plunger 56 forwardly of chamber 48*b*. As plunger 56 is moved forwardly, fluid contained within vial chamber 48*b*, will flow through hollow cannula 222, past check valve 57, into passageway 226 and finally into fluid reservoir 224 (FIG. 25). In certain instances, reservoir 224 may be prefilled with a saline solution or the like with which the fluid contained in vial 48 will be controllably intermixed as the adapter assembly is moved inwardly.

Considering now the previously mentioned dose control means of the invention, this important means here comprises a control knob assembly 230 which includes a collar portion 230*a*. Assembly 230 is rotatably mounted within device housing 202 so that a portion of the knob extends through an opening 233 formed in cover 208 (FIGS. 20 and 21). More particularly, control knob assembly 230 is rotatably carried by a generally cross-shaped knob support member 236 which is connected to a support platform 239. The details of construction of knob assembly 230 and the drive mechanism associated therewith for advancing adapter assembly 210 into housing 202 are illustrated in FIGS. 21, 22, and 27. As indicated in FIG. 27, control knob 230 is provided with gear teeth 230*b* which mate with teeth 238*a* formed on an idler gear 238 which is rotatably carried within device housing 202 in the manner shown in FIG. 30. Idler gear teeth 238*a*, in turn, mesh with teeth 240*a* formed on the drive gear 240 which is rotatably supported by a shaft 242 mounted within device housing 202. Drive gear 240 engages longitudinally spaced apart teeth 244 which are formed on adapter housing 210a (FIG. 21). With this construction, as knob 230 is rotated by rotational forces exerted thereon, adapter housing 210a will be caused to controllably move inwardly of annular space 214 causing pusher rod 216 to move plunger 56 inwardly of vial assembly 48. In this way precise incremental doses of the medicament contained within vial 48 can be controllably introduced into reservoir 224. Indicia viewable through a window 249 formed in cover 208 indicate the volume of the dose being dispensed (FIG. 20).

Figure 34B:
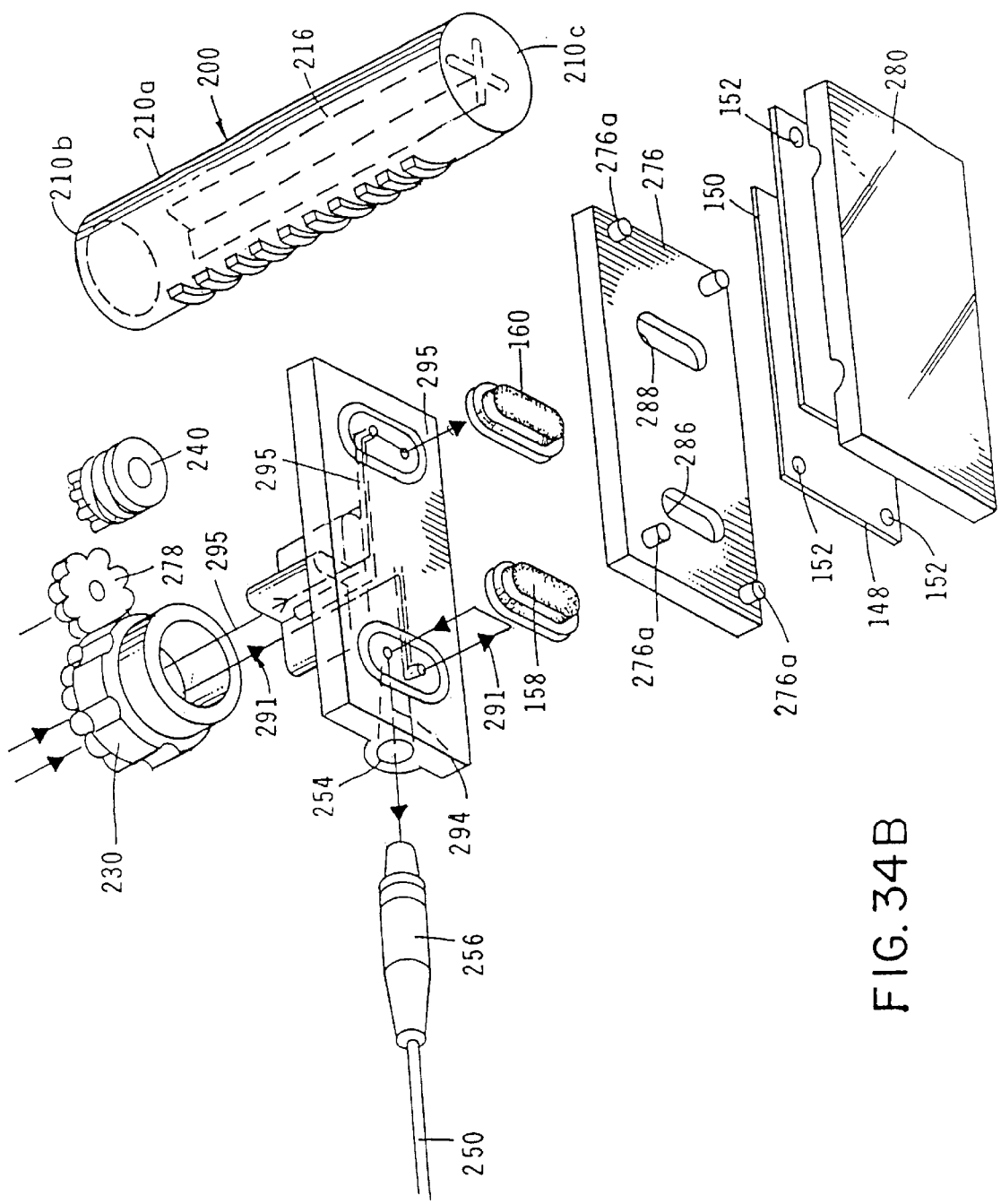
FIG. 34 is a generally perspective exploded view similar to FIG. 21 and showing the fluid flow paths through the device.

Once the reservoir has been filled and the adapter assembly has been appropriately mated with device housing 202, the apparatus will remain in this readied condition until the outlet passageway of the device is opened. Once the outlet passageway has been opened, the stored energy means or membrane 250 will tend to return to a less distended condition causing fluid to flow outwardly of the apparatus via a passageway 252 formed in base assembly 204, through the novel rate control means of the invention and finally outwardly of the device via an outlet portion 254 (FIG. 34). In a manner presently to be described, a connector 256 and delivery line 258 are connected to the outlet port 254.

As best seen in FIG. 28, base platform 204a, which includes an ullage protuberance 260, is specially configured to receive a membrane clamping ring 262 which functions to securely clamp membrane 250 about its periphery 250a. With this construction, distendable membrane 250 is securely clamped in position with cover 208 overlaying membrane 250 in the manner shown in FIGS. 25 and 28.

Turning next to FIGS. 20, 21, and 33, the novel delivery line interconnection and release means of the invention is there illustrated. This means functions to releasably interconnect the delivery assembly, which here includes connector 256 and delivery line 258. This novel interconnection and release means here comprises a push button subassembly 260, which includes a head portion 260a which extends through an opening 261 formed in cover 208. Connected to head portion 260a is a leg 264 which terminates in a tab 266 which is securely connected to cover 208 (FIG. 33). Disposed between leg 264 and tab 266 is a yieldably deformable segment 268 which functions as a living hinge so that pushing upon head 260a will cause leg 264 to move out of locking engagement with a shoulder 256a formed on connector 256. When the push button subassembly is in an upward, at-rest position, leg 264 locks against shoulder 256a preventing removal of connector 256 from the device housing. However, it is apparent that a downward force exerted on head portion 260a will cause legs 264 to move away from the connector so as to permit it to be disconnected from housing 202. When the delivery line is connected to the housing in the manner described, fluid can flow from reservoir 224 outwardly of the device via the indicator means and via the novel flow rate control means, the character of which will next be described.

The flow rate control means is also a very important feature of this latest form of the invention and functions to adjustably control the rate of fluid flow from the reservoir 224 of the apparatus to the device outlet passageway 254. This novel rate control means is virtually identical in construction and operation to that described in connection with the first embodiment of the invention shown in FIGS. 1 through 19. As before, the rate control means comprises a mechanism 124 which includes a central body portion 122 which is disposed internally of a knurled control knob 124. Knob 124 is rotatobly supported by members 126 and 128 which are quite similar to the previously described members 126 and 128 and are mounted internally of housing 202 (FIGS. 17 and 34). A portion of knob 124 extends through an opening 267 formed in cover 208 (FIG. 20).

As best seen in FIGS. 31 and 32, central body portion 122 carries a plurality of circumferentially spaced apart flow restrictors. By rotating knob 124, each of the flow restrictors can be selectively moved into index with the flow passageway 252 (FIG. 28) which carries the fluid from reservoir 224 to support member 126 of the device. In the manner previously described, by rotating knob 124 relative to housing 202, each of the rate control frits 130 can be moved sequentially into alignment with fluid passageway 252 and with a passageway 126a (FIGS. 28 and 34) which extends through member 126. Because each of the frits 130 is of a different, preselected porosity as indicated by indicia viewable through a window 255 formed in cover 208, it is apparent that tie rate of fluid flowing outwardly of the device through outlet passageway 254 can be precisely controlled by positioning a particular frit in the flow path.

Another unique feature of the apparatus of this latest form of the invention which is shown in FIGS. 21, 31, and 32 is a novel control knob locking means which locks knobs 124 and 230 against rotation. This locking means here comprises yieldable knob engagement arms 270 which engage knobs 124 and 230 and prevent their rotation when a locking button 272 is pushed inwardly of housing 202 in the manner shown in FIG. 32. Arms 270 terminate in an end portion 270a which ratchet out of engagement with the grooves 124a formed in knob when the push button is in the retracted position shown in FIG. 31. However, when the push button is pushed in, it will engage arm 270 to prevent its separation from knob 124. Push button 272 is provided with spanner holes 272a (FIG. 26) which accept spaced apart pins provided on a physician's locking key 141d (FIG. 17) which can be used to lock the push button in the locked configuration shown in FIG. 32, With this arrangement once the flow rate is set it cannot be changed by anyone other than an authorized care giver having access to the locking key.

As in the earlier described embodiment, this latest embodiment also includes novel indicator means which functions to distinguish among three conditions of operation of the device, namely normal fluid flow, blockage or occlusion, and reservoir empty. Turning particularly to FIGS. 21 and 34, this novel flow indicator means is quite similar in construction and operation to the previously described flow indicator means and includes an indicator base or platform 276 and a boot clamping plate 278. Additionally, the indicator means here comprises a support or lens plate 280. Platform 276, clamping plate 278 and support plate 280 are all enclosed within housing 202 in the manner indicated in FIG. 21. When the components are positioned within housing 202, plate 280 is viewable through an aperture 282 provided in housing 202 (FIG. 20).

Disposed between lens plate 280 and platform 276 are first and second indicia-carrying means shown here as a pair of closely adjacent, thin films 148 and 150 which are of identical construction and operation to those embodied in the first form of the invention (see also FIGS. 4, 6, and 8 of incorporated by reference U.S. Pat. No. 5,721,382. The inferior and superior films are provided at their opposite ends with apertures 152 which receive retention pins 276a provided on platform 276 (FIG. 34) which permit attachment of the film to platform 276 in a manner such that the non-patterned portions of each film covers boot openings 286 and 288 provided proximate each end of platform 276 with the patterned portions of both the superior and inferior films being maintained in index. With this construction, each thin film is able to move in response to pressure exerted thereon by the actuating means of the invention which is of the character previously. As the films move, the visible symbol pattern will, of course, change due to the transverse displacement of the patterns imprinted thereon.

As before, boots 158 and 160, which here comprise the actuator means of this latest form of the invention, will be deflected outwardly in a direction toward plate 280 when the device is filled and primed, but not in a state of delivery or when there is a build up of fluid pressure during delivery that is caused by blockage of the delivery line downstream from boot 158. While boot 160 can be deflected by normal line pressure, boot 158 is deflected only by pressure buildup resulting from the downstream blockage. When both elastomeric boots 158 and 160 are deflected outwardly, both the superior and inferior films are displaced transversely to a second position revealing a second symbol, as for example, an X as viewed through the viewing aperture of the support plate (see also FIGS. 35 and 36 of U.S. Pat. No. 5,721,382 which is incorporated herein by reference).

A third alignment of symbol patterns as shown in FIG. 32 of U.S. Pat. No. 5,721,382 is visible when the device is in an unfilled state or when the delivery line is open, the reservoir is empty and fluid delivery of the patient has been completed. In this case, there is no fluid pressure in the line on either the upstream or the downstream side of the flow control means and thus both the first and second boots are in a non-deflected position. In this condition, the interior and superior films are not transversely displaced and thus exhibit a third combination of patterns resulting in a third symbol as, for example, a circle being visible through the viewing aperture of the support plate. As before, boots 158 and 160 can be precisely tailored to deflect under various pressures thereby permitting great apparatus versatility.

During the fluid dispensing step, when fluid is forced through the reservoir outlet by the stored energy means, the fluid will flow into passageway 252, and then will be split into two flow paths 252a and 252b. Flow path 252a extends through a first orifice 126c formed in member 126 and then through a central orifice 122a formed in control member 122. Flow path 252b extends through a second orifice 126a formed in member 126 and then through a selected frit 130 of the rate control means. From the selected frit 130, the fluid will flow at a reduced pressure into a chamber formed in the distendable elastomeric first boot 158 in the direction of the arrows 291. When the fluid flowing from reservoir 224 in the direction of the arrow 291 of FIG. 34 impinges upon boot 158, the central portion of the boot will be deflected outwardly into pressural engagement with indicator film 148. After impacting boot 158, the low pressure fluid will then flow back into outlet passageway 294 (FIG. 22) and outwardly of outlet 254 at the predetermined rate of flow.

Fluid flowing from reservoir 224 along path 252a will flow through orifice 126c formed in member 126 and then through a passageway formed in hub-like member 236. Next, fluid will flow in the direction of arrows 295 into elastomeric, distendable boot 160 which also forms a part of the indicator means of this latest form of the invention.

It is to be observed that fluid flowing from reservoir 224 along path 252a and through central orifice 122a of member 122 will flow toward boot 160 under a higher pressure than fluid flowing toward boot 158. This is because the pressure of the fluid flowing toward boot 158 has been reduced as a result of the fluid flowing through the adjustable rate control means of the invention. As is more fully discussed in incorporated by reference U.S. Pat. No. 5,721,382, this result enables a determination of the various fluid flow operating conditions of the device namely normal fluid flow, fluid flow blockage or occlusion, and reservoir empty Turning now to FIGS. 35 through 38, an alternate form of the apparatus of the invention for controlled delivery of medicinal fluid to a patient is there shown and generally designated by the numeral 300. The apparatus here comprises four major components, namely a housing, first and second fill assemblies and infusion means for infusing medicinal fluids into the patient. Housing 302 of the apparatus includes a base assembly 304 and a stored energy means which cooperates with the base assembly to form a fluid reservoir 306 (FIG. 37). Reservoir 306 is provided with first and second inlets 308 and 310 respectively. Base assembly 304 includes a base 312 having a receiving chamber 314 formed therein. The stored energy means of this latest form of the invention comprises an elastomeric membrane 316 which is clamped to base 312 by means of a clamping ring 320 in a manner similar to that described in incorporated by reference U.S. Pat. No. 5,840,071. Clamping ring 320, along with elastomeric membrane 316 is enclosed by a cover 322 of the configuration shown in FIGS. 35 and 37. As best seen by referring to FIG. 37, receiving chamber 314 of base 312 is adapted to controllably receive the first fill assembly 324 of the invention to permit controlled filling of the reservoir of the device through the use of a novel dose dialing mechanism the character of which will presently be described. Base 312 also includes a fill port assembly 328 to which the second fill assembly 338 of the invention can be removably interconnected. As indicated in FIG. 37 fill port assembly 328 communicates with second inlet 310 via a fluid passageway 332. The construction and operation of the important fill port assembly 328 will presently be described.

Figure 35:
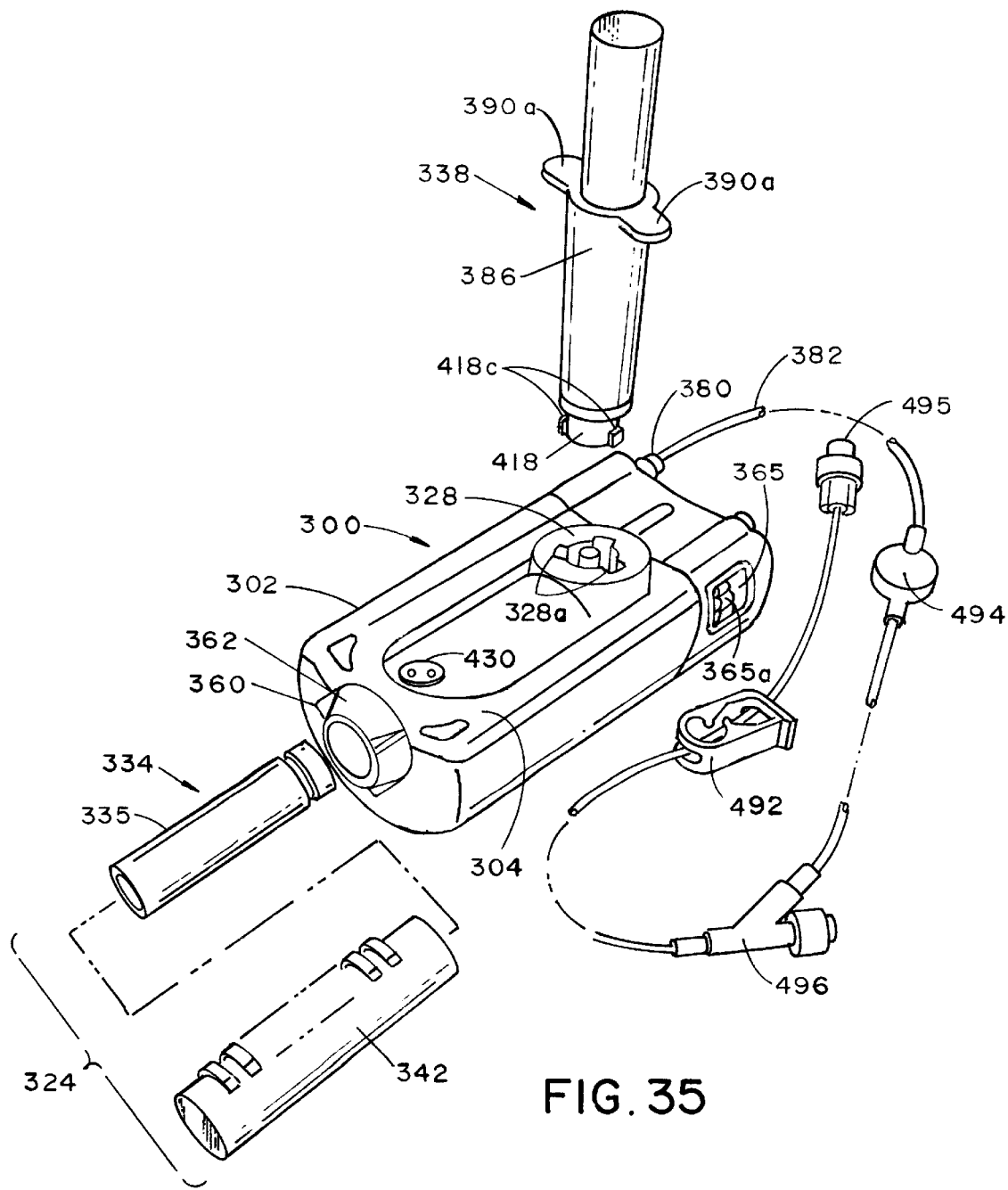
FIG. 35 is a generally perspective view of an alternate form of fluid dispensing apparatus of the invention which includes a novel medicament dose dialing feature.

Turning particularly to FIGS. 35 and 37, the first fill assembly 324 of the apparatus can be seen to comprise a container subassembly 334, which is of similar construction to that previously described, and an adapter sleeve 342, which is of a highly novel configuration and is adapted to mate with the important advancing means of the invention for incrementally advancing the adapter sleeve along with the container or vial subassembly 334 into the receiving chamber 314. As before, as the adapter sleeve is advanced into receiving chamber 314, a plunger 344 is telescopically moved within a fluid chamber 346 of container assembly 334 between first and second locations. As best seen in FIG. 37, adapter sleeve 342 has a first open end 342a and a second closed end 342b. The adapter assembly 342 is telescopically receivable within receiving chamber 314 and is moved by the advancing means of the invention from a first extended position shown in FIG. 37 into a second fluid dispensing position. As was the case with adapter subassembly 50, adapter assembly 342 also includes pusher means shown here as an elongated pusher rod 342c which functions to move plunger 344 within the fluid chamber 346 of the container subassembly upon operation of the dose dialing means of the invention.

Figure 40:
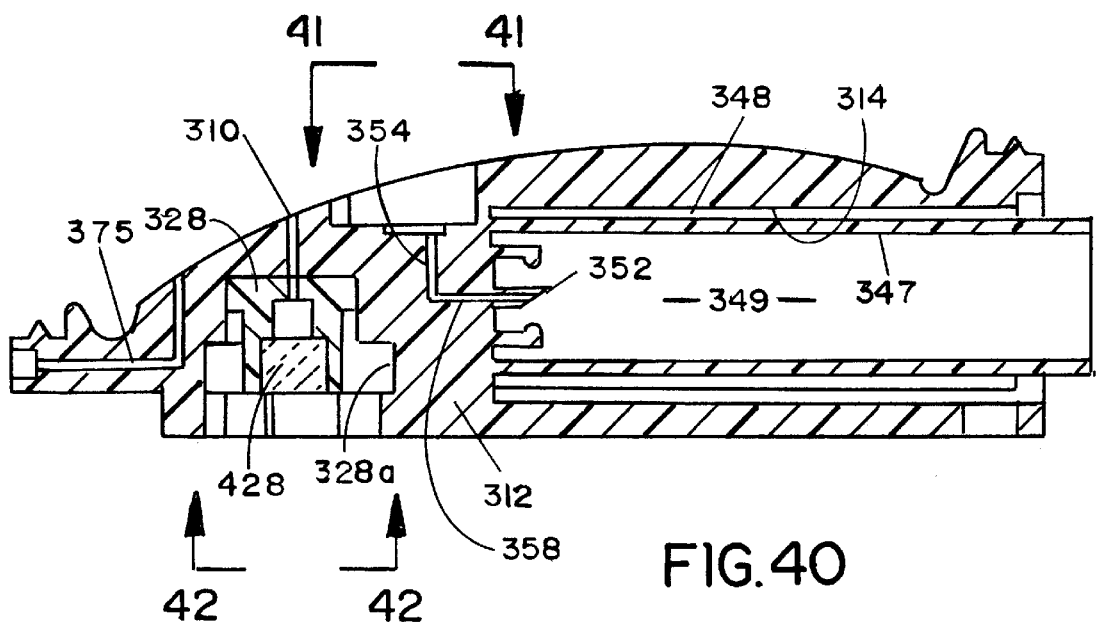
FIG. 40 is a cross-sectional view of the base portion of the apparatus shown in FIG. 37.
Figure 42:
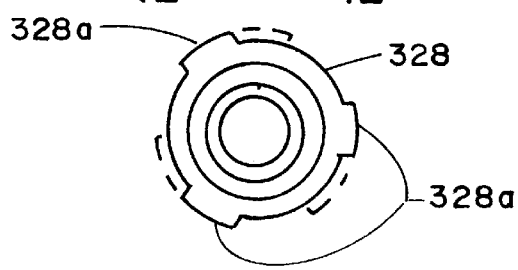
FIG. 42 is a view taken along lines 42—42 of FIG. 40

As best seen in FIG. 40, provided within base 312 is an elongated, generally cylindrically shaped wall 347. Wall 347 is radially spaced from the interior wall of receiving chamber 314 so as to define a longitudinally extending annular space 348 and cylindrical space 349 (see also FIG. 37). With this construction, during the mating of the reservoir fill assembly with the base assembly, the outer wall of adapter assembly 342 is closely received within annular space 348 as the adapter subassembly is moved inwardly or forwardly of the device housing by means of the dose dialing means.

When the adapter assembly is originally mated with the base in the manner shown in FIG. 37, the container assembly will be moved telescopically inwardly to move a septum 350 of container assembly 334 into piercing engagement with a hollow cannula 352 which extends inwardly into cylindrical space 349.

Once the fluid flow path between the hollow cannula 352 and the fluid reservoir 306 of the apparatus is thus created via a passageway 354, an inward movement of the adapter subassembly can be accomplished using the novel dose dialing means of the invention. As the dose dialing means controllably moves the adapter subassembly inwardly, pusher rod 342c will move plunger 344 forwardly of chamber 346. As plunger 344 is moved forwardly, fluid contained within vial chamber 346 will flow through hollow cannula 352, past an umbrella check valve 358 of conventional construction (FIGS. 37 and 40) and into inlet 308 of fluid reservoir 306 (FIG. 37). As will be discussed hereinafter, in certain instances, reservoir 306 may be prefilled with a solution with which the fluid contained in vial assembly 334 will be controllably intermixed as the adapter assembly is moved inwardly.

Considering now the previously mentioned dose dialing means of the invention, this important means here comprises advancing means connected to housing 302 for controllably advancing adapter assembly 342 into receiving chamber 314. In the form of the invention shown in the drawings, this important advancing means can be seen to comprise an advancing subassembly 360 that includes an advancing dial 362 which is rotatably connected to base 304 in the manner indicated in FIG. 37. Advancing subassembly 360 also includes a dial support component 364, which is of the configuration best seen in FIGS. 47, 48 and 49. Additionally, advancing subassembly 360 includes a locating ring 366 of the character illustrated in FIGS. 45 and 46. Locating ring 366 is provided with a yieldably deformable, reverse rotation blocking tab 366b (FIG. 46) which engages teeth 362a provided on ring 362 to prevent reverse rotation of advancing dial 362 (FIG. 52).

Dial support component 364 includes a skirt like portion 364a which is receivable within an opening 367 formed in base 304 (FIG. 37) and a flange portion 364b. Locating ring 366 is provided with a locating tab 366a (FIG. 45) which is receivable within a locating slot 364c formed in skirt portion 364a of dial support component 364. When the various components of the advancing means are assembled in a manner shown in FIG. 37 advancing dial 362 is held captive between flange 364b and locating ring 366.

Figure 55:
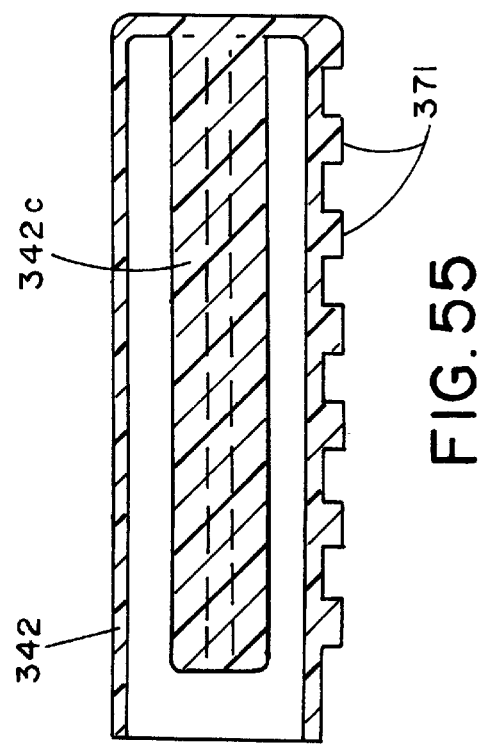
FIG. 55 is a cross-sectional view taken along lines 55—55 of FIG. 54.

As shown in FIGS. 51 and 52, advancing dial 362 includes teeth engaging means here provided as threads 370 formed on the interior wall of advancing dial 362. Upon insertion of vial subassembly 334 into cylindrical space 349 and insertion of adapter sleeve 342 into annular space 348, threads 370 will mate with a plurality of longitudinally spaced advancing teeth 371 formed on the exterior wall of adapter sleeve 342 (FIGS. 37 and 55). With this construction it is apparent that rotation of the advancing dial 362 will cause adapter sleeve 342 to be incrementally advanced into annular space 348. As the adapter sleeve so advances, pusher rod or member 342c will urge plunger 344 inwardly of fluid chamber 346 of container subassembly 334.

When the container subassembly is seated and a manner shown in FIG. 37 with hollow cannula 352 piercing septum 350, an inward movement of plunger 344 resulting from one rotation of dial 362 will cause one-tenth of the fluid contained within container 335 of the container subassembly 334 to flow into the hollow cannula, through passageway 354, past umbrella-like check valve 358 and then into reservoir 306 via inlet 308.

Figure 36:
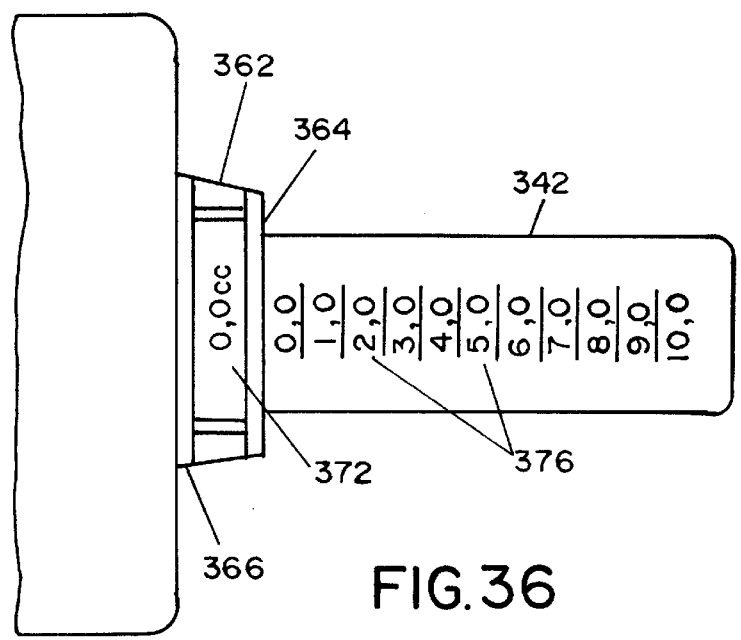
FIG. 36 is an enlarged, fragmentary top plan view of the medicament dose dialing assembly and fill assembly of the apparatus of the invention shown in FIG. 35.
Figure 37A:
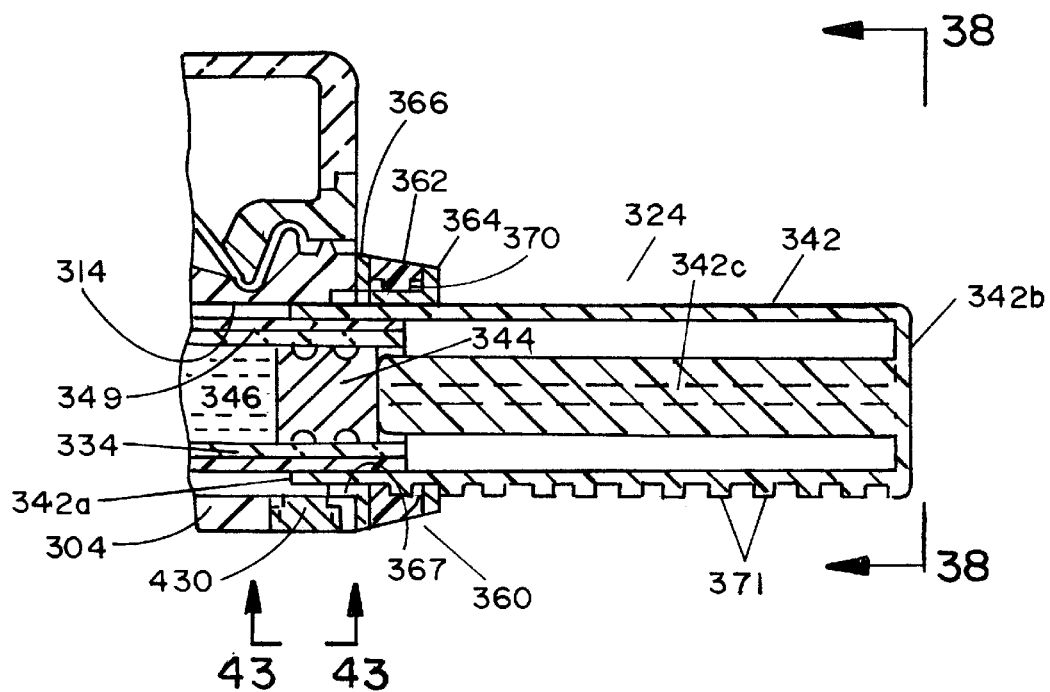
FIG. 37 is a side elevational, cross-sectional view of the housing and fill assemblies of the apparatus of the invention shown in FIG. 35.
Figure 37:
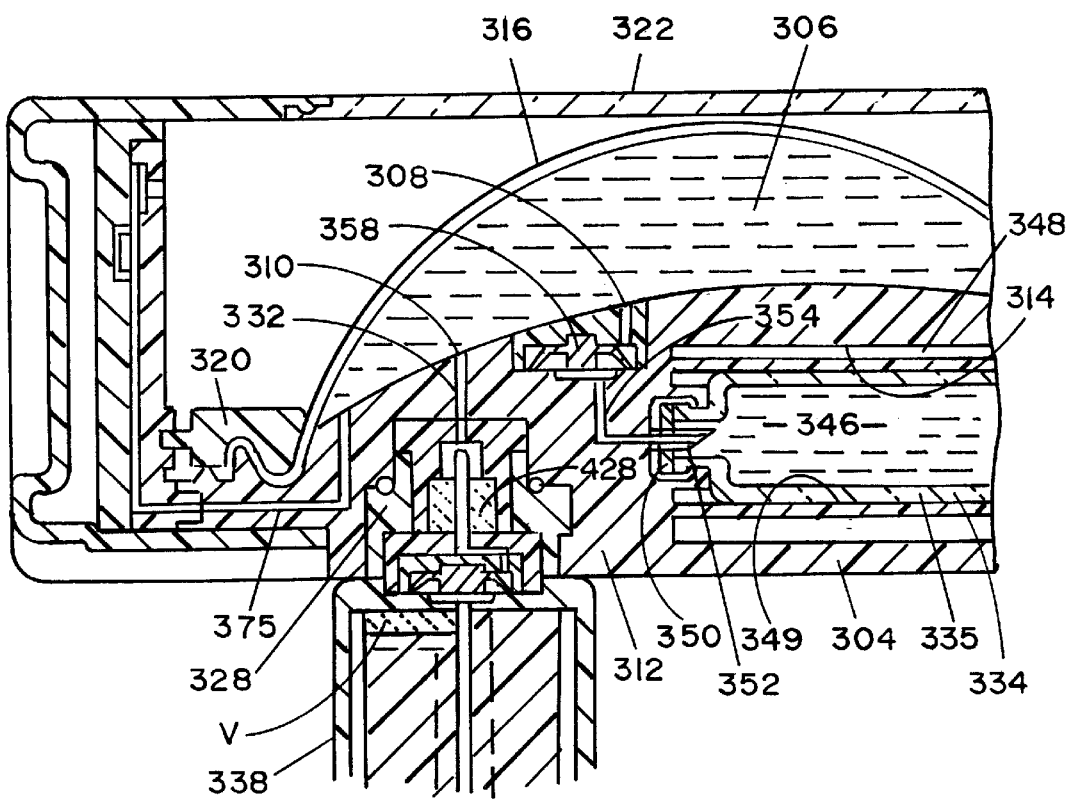
Figure 39:
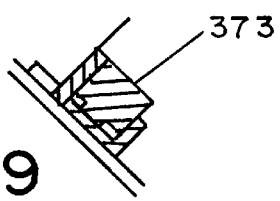
FIG. 39 is a cross-sectional view taken along lines 39—39 of FIG. 38.
Figure 38:
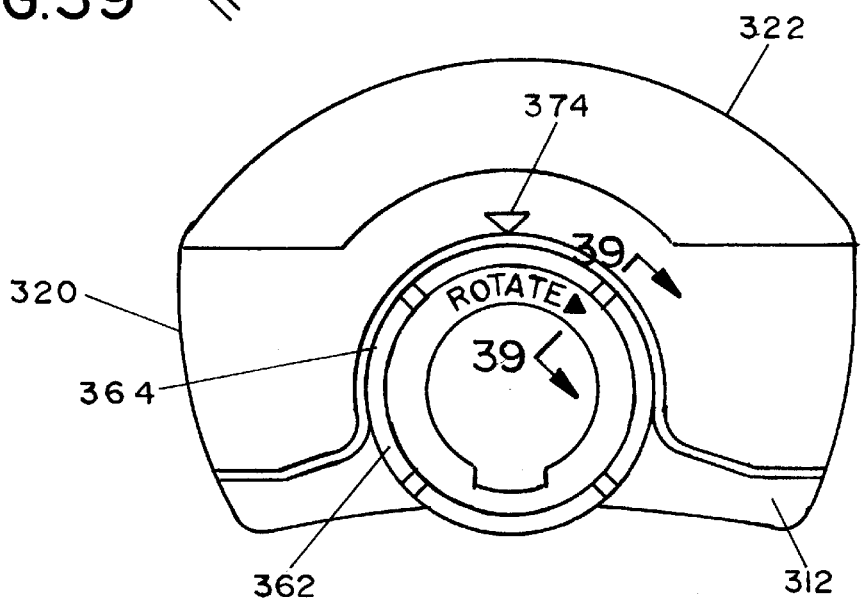
FIG. 38 is a view taken along lines 38—38 of FIG. 37.
Figure 41:
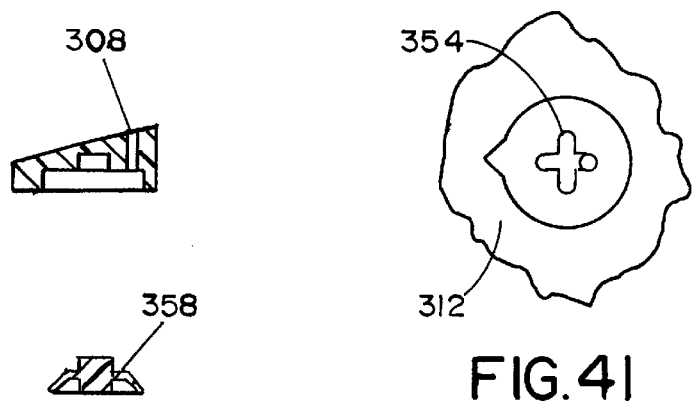
FIG. 41 is a view taken along lines 41—41 of FIG. 40.
Figure 54:
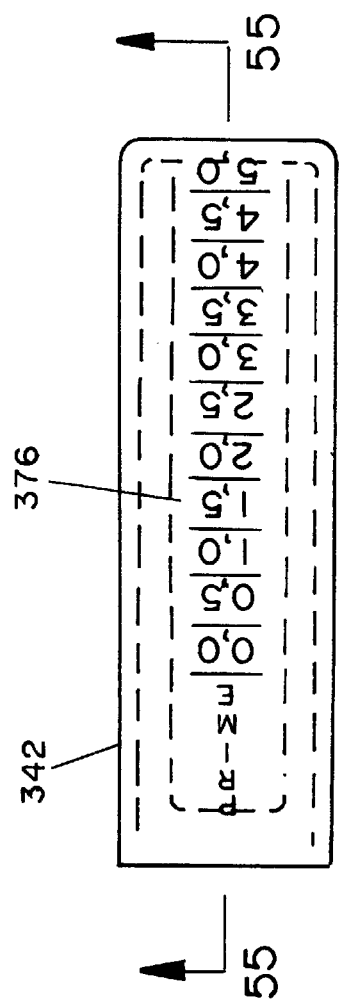
FIG. 54 is a top plan the view of one form of the fill assembly housing of the apparatus of the invention showing the indicia printed thereon for determining the volume of medicament being delivered to the fluid reservoir of the dispensing component of the apparatus of the invention.

Referring next to FIGS. 36 and 54 it is to be noted that advancing dial 362 is provided with circumferentially spaced incremental indicating indicia 372. As advancing dial 362 is rotated by finger engagement with tabs 373 (FIG. 39) the indicia 372 will sequentially move past an indicating arrow 374 imprinted on housing 302 (FIG. 39). As best seen in FIG. 54, hollow housing 342 of the adapter subassembly is provided with longitudinally spaced dose volume indicating indicia 376. Each of the indicia 376 indicates one-tenth of the volume of the container or vial 335 of the vial assembly 334. Similarly the indicating indicia 372 imprinted on advancing dial 362 indicate a ¼ division of the indicia 376 imprinted on the hollow housing of the adapter sleeve 342, that is 0.25, 0.50 and 0.75. Accordingly when advancing dial 362 is rotated a full 360 degrees, one-tenth of the fluid contained within the vial 335 will be introduced into reservoir 306. In similar fashion when the advancing dial 362 is rotated ¼ of a turn as indicated by the indicia 372, 0.025 of the fluid contained within the vial will be introduced into reservoir 306 (FIG. 53). With this arrangement the volume of fluid introduced into reservoir 306 by the rotation of advancing dial 362 can be precisely controlled. It is to be understood that indicia indicating alternate dosing parameters can be used if desired with corresponding alternate thread configurations on the adapter sleeve and advancing dial.

Once the reservoir has been filled and the adapter assembly has been appropriately mated with housing 302, the apparatus will remain in this readied condition until the outlet passageway of the device is opened. Once the outlet passageway has been opened, the stored energy means or membrane 316 will tend to return to a less distended condition causing fluid to flow outwardly of the apparatus via a passageway 375 formed in base 304, through the novel rate control means 365 of the invention (FIG. 35) and finally outwardly of the device via the infusion means. Rate control means 365 is similar in construction to that shown in FIGS. 15 and 16 and includes a central body portion which carries a plurality of circumferentially spaced flow resistors. By rotating the knob 365a of the rate control means, (FIG. 35) each of the flow restrictors can be selectively moved into index with the flow passageway that carries the fluid from the reservoir to the infusion means of the device.

Figure 63:
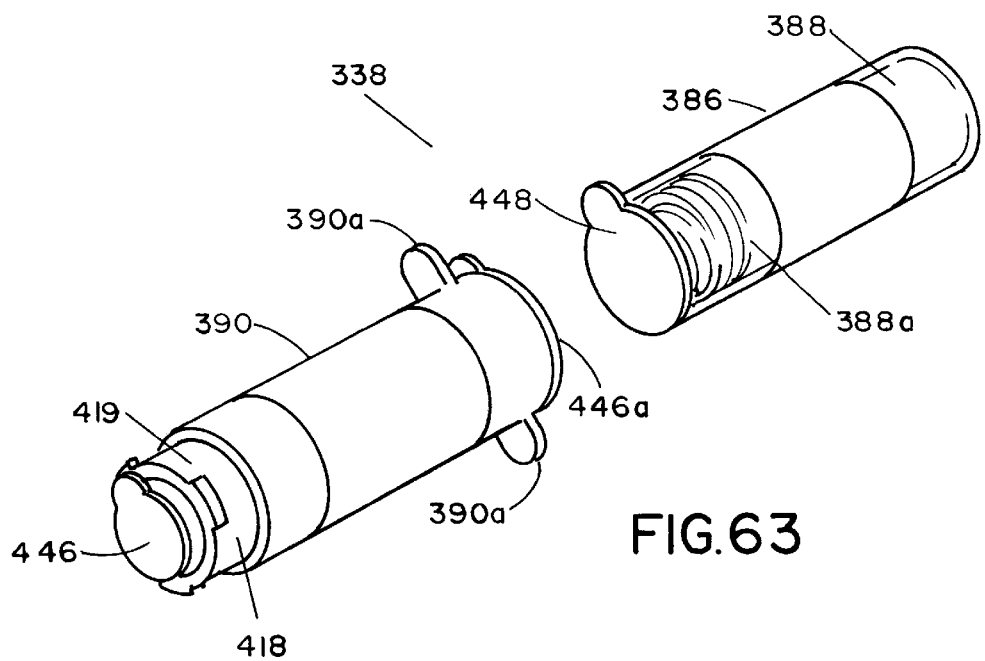
FIG. 63 is a generally perspective exploded view of the second fill assembly of the apparatus of the invention.
Figure 64:
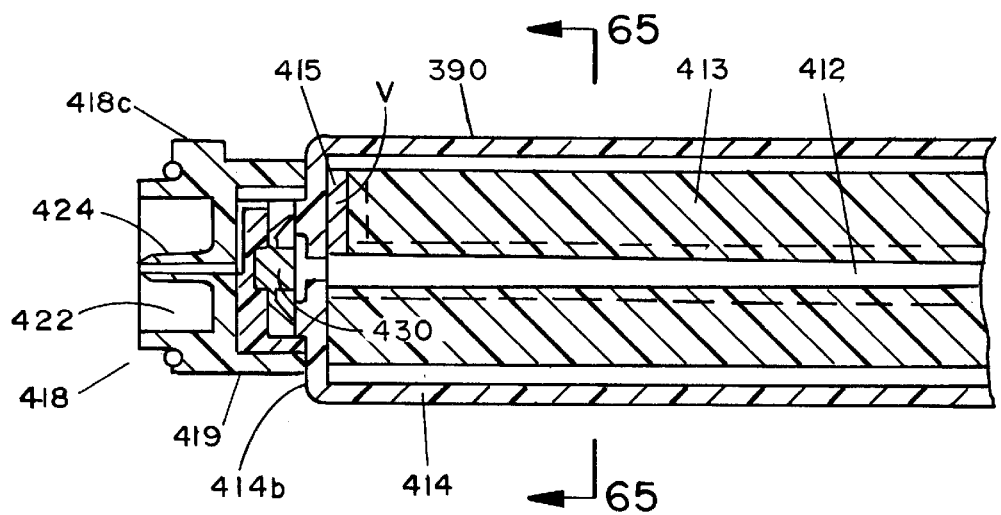
FIG. 64 is a side elevational, cross-sectional view of the second fill assembly shown in an assembled configuration.

Considering next the second fill assembly 338 of the invention, this subassembly is also used to fill reservoir 306 and, as previously mentioned, comprises a novel fluid transport assembly 386 of the general configuration shown in FIG. 35. Referring to FIGS. 63 and 64, it is to be noted that second fill subassembly 338 is specially designed to be mated with fill port assembly 328. As illustrated in FIGS. 63 and 64, fluid transport assembly 386 comprises a container subassembly 388 and an adapter assembly 390 which telescopically accepts the container subassembly. Container subassembly includes a body portion 388a, having a fluid chamber 389 for containing a fluid "F". Body portion 388a is provided with a first open end 392 and a second closed end 394. First open end 392 is sealably closed by closure means here provided in the form of a plunger assembly 396 (FIG. 64). Plunger assembly 396 comprises an elastomeric plunger 398 and a connector means, or connector 400 which functions to interconnect the container assembly with the adapter assembly. Plunger assembly 396 is telescopically movable within chamber 199 of container subassembly 388 from a first location proximate first open end 392 to a second location proximate closed end 394.

As best seen in FIG. 64, connector 400 includes threads 402 which can be threadably connected to threads 406 provided on adapter assembly 390. Connector 400 also includes a pierceable central wall 400a (FIG. 66) which is pierceable by a cannula 410 of the adapter assembly. Cannula 410 comprises a part of first flow control means of the adapter assembly for controlling fluid flow into a fluid flow passageway 412 formed interiorly of a pusher member 413 (FIG. 66). Connector 400 is integrally formed with plunger 398 in the manner shown in FIG. 66 so that as plunger 398 is moved toward closed end 394, in a manner presently to be described, connector 400 and plunger 398 will move as a unit. To prevent leakage of fluid past plunger 398, the plunger is provided with rings 398a which are of a diameter slightly greater than the inside diameter of container body 388a. Plunger 398 also includes a central passageway 398b which is in open communication with chamber 389.

Figure 65:
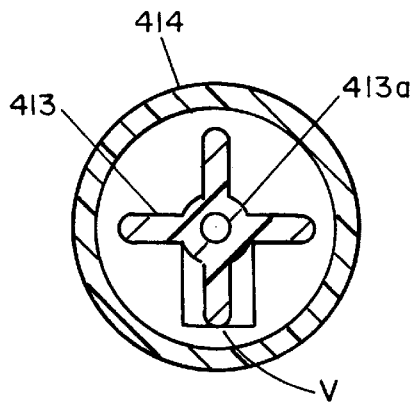
FIG. 65 is a cross-sectional view taken along lines 65—65 of FIG. 64.
Figure 64A:
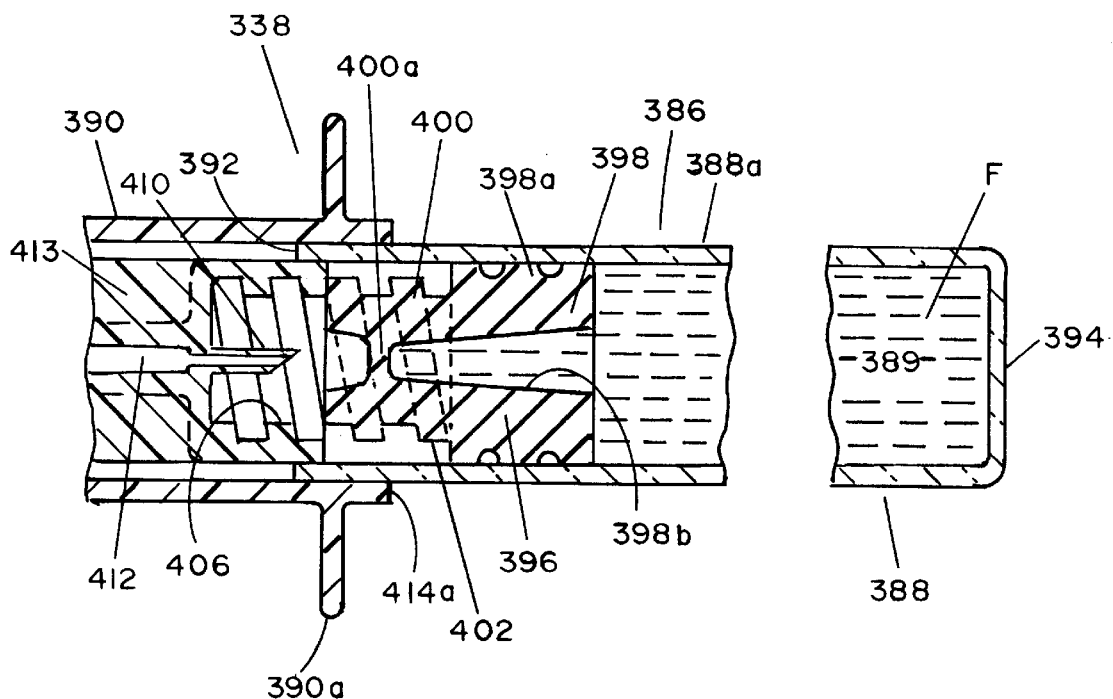

Referring now particularly to FIGS. 64 and 66, it can be seen that adapter subassembly 390 comprises a hollow housing 414 having a first open end 414a and a second closed end 414b. Container subassembly 388 is telescopically receivable within open end 414a of housing 414 so that the container can be moved from a first extended position shown in FIG. 64 to a second container encapsulation position wherein container 388 is substantially encapsulated within housing 414. Provided interiorly of the adapter subassembly is a pusher means shown here as the previously identified pusher member 413. As best seen in FIG. 65 pusher member 413 has an elongated, generally cross shaped pusher section 413a (FIG. 65) which functions to move plunger 398 within fluid chamber 389 from the first forward position shown in FIG. 64 to the second position wherein it is disposed proximate end wall 394. Pusher member 413 also includes a passageway 415 which permits gases trapped within passageway 412 to be vented to atmosphere via hydrophobic vent means "V".

Also forming a part of the adapter assembly of the invention is a connector means or cap assembly 418 (FIG. 66B) which is connected to body portion 414 in the manner shown in FIG. 66. Cap assembly 418 includes a generally cylindrical exterior wall 419, the interior surface of which forms a chamber 422 into which a second cannula 424 extends. To interconnect second fill assembly 338 with the fluid delivery apparatus, the barrel-like portion of closure cap 418 of the second fill assembly is mated with fill port 328 formed in base 304. As the barrel-like portion enters the lower portion of the fill port, the circumferentially spaced, bayonet type connectors or locking tabs 418c of closure cap 418 (see FIGS. 35 and 66B) are received between the circumferentially spaced tab receiving slots 328a formed in the fill port. Relative rotation of the fill assembly and the fluid delivery component enables secure interconnection and sterile coupling of the second fill assembly with the fill port 328. As the second fill assembly 338 is mated with the delivery component, cannula 424 of the fill assembly will pierce a pierceable septum 428 which is mounted within fill port 328.

When the second fill assembly is connected to the fill port, an inward pressure exerted on container assembly 388a will cause adapter cannula 410 to pierce wall 400a of connector 400 (FIG. 64) and will cause fluid to flow into passageway 412) past an umbrella check valve 430, through cannula 424 and into fluid reservoir 306 via inlet 310, is to be understood that second fill assembly 338 can be used to fill reservoir 306 with a wide variety of different fluids. By way of example, and not by way of limitation, the second fill assembly may be used to fill reservoir 306 with a diluent. When the second fill assembly is so used, the medicament contained within container 335 of the first fill assembly will be intermixed with the diluent prior to the delivery of the mixture to the patient via the infusion means of the apparatus.

Figure 58:
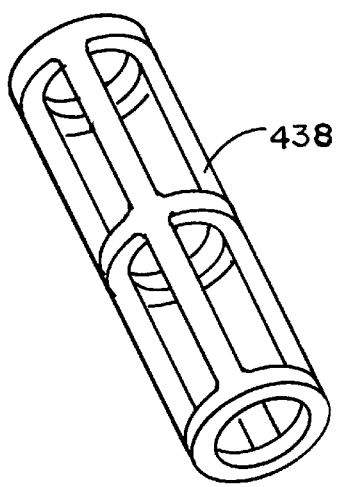
FIG. 58 is a generally perspective view of the vial spacer component of the apparatus of the invention.
Figures 59, 60:
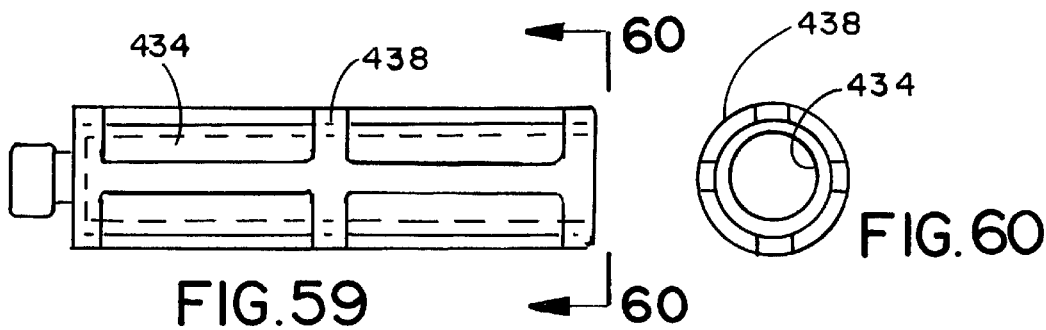
FIG. 59 is a side elevational view of the vial spacer component shown in FIG. 58.
FIG. 60 is a view taken all lines 60—60 the of FIG. 59.
Figures 61, 62:
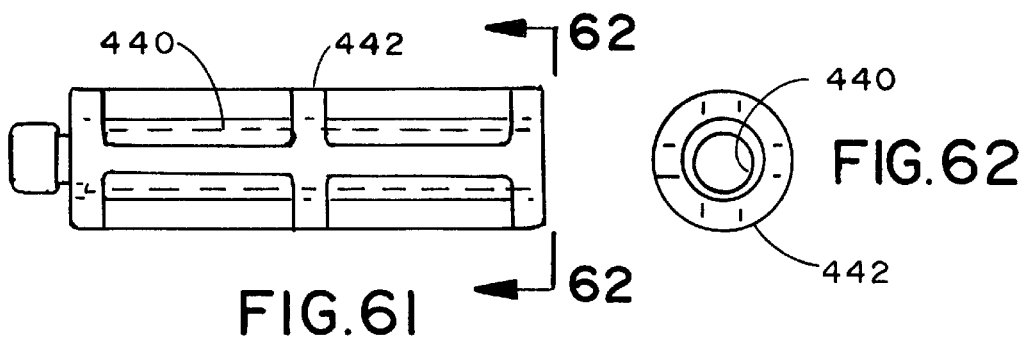
FIG. 61 is a side elevational view ol all alternate form of the vial spacer component of the invention adapted for use with smaller volume vials.
FIG. 62 is a view taken all lines 62—62 of FIG. 61.

As previously mentioned, the medicament doses contained within vial assembly 334 can be precisely controlled through use of the dial dosing means of the invention. In this regard, as earlier pointed out, one rotation of dial 362 of the advancing means of the invention will cause $\frac{1}{10}$ of the volume of the vial 335 to be introduced in the to reservoir 306. Increments of that volume can be introduced by rotating dial 362 in increments of $\frac{1}{4}$ of a turn. By knowing the volume of vial 335, the physician or caretaker can precisely control the medicament dose to the reservoir by manipulation of the advancing means of the invention in a manner previously described herein. With this in mind, it should be noted that medicament vials of a various sizes can be used with the first filling assembly of the apparatus of the invention. More particularly, as illustrated by FIGS. 58, 59 and 61, when a smaller volume medicament file, such as the 3.0 cubic centimeter (cc) vial 434 identified in FIG. 59 is used, a vial spacer such as that identified by the numeral 438 in FIG. 58 can be used. When even a smaller vial, such as the 1.5 cc vial 440 shown in FIG. 61 in used, a vial spacer such as that identified by the numeral 442 in FIG. 61 can be used. Vial spacers 438 and 442 are configured to be closely received within the interior space defined by a wall 347 of the base assembly.

Figure 43:
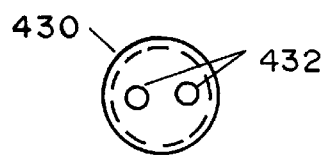
FIG. 43 is a view taken along lines 43—43 of FIG. 37.
Figure 44:
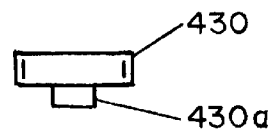
FIG. 44 is a side-elevational view of the locking member of the apparatus of the invention for preventing inward movement of the filling assembly.
Figure 44A:
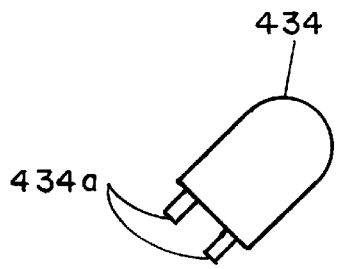
FIG. 44A is a top view of a physician's key used with the lock-out means of the invention.

Once the dosing regimen has been determined by the physician, the advancing means can be locked against further advancement through use of the novel locking means of tie invention which here comprises a locking member 430 that is threadably connected to base 304 in the manner illustrated in FIG. 37. As indicated in FIGS. 43 and 44 locking member 430 is provided with spaced apart spanner receiving openings 432 which are adapted to receive spanner elements 434a of a physician's key 434 of the character shown in FIG. 44A. Using the physician's key, the physician or caretaker can rotate member 410 so that the stem 430a thereof is threadably moved into blocking engagement with one of the teeth 371 formed on adapter sleeve 342 thereby preventing further operation of the advancing means.

It is to be understood that the connector or barrel portion 418 of the second fill assembly can be provided with one or two rather than three circumferentially spaced locking tabs, and fill port assembly 328 can be provided with one or two specially configured tab receiving openings of a predetermined size and angular location. With this novel arrangement, fill assemblies containing a first medicament, such as morphine sulfate can be provided with a three-tab closure cap assembly 418 and the fluid delivery device can be provided with a mating three-slot, fill port to enable sterile coupling. In like manner, fill assemblies containing a second medicament, such as a first anti-infectant agent can be provided with a two-tab closure cap assembly 418 and the fill port of the fluid delivery device can be provided with a mating two-slots to enable sterile coupling. When the fill assembly contains a third medicament such as an oncolytic agent, the second fill assembly can be provided with a single-tab closure cap assembly having a tab of a predetermined size and angular location. Similarly, the fill port of the fluid delivery device can be provided with a single-slot specifically sized and located to receive the single locking tab of the closure cap. In this way, potentially serious errors of misadministration of medicaments can be elegantly and positively avoided. Additionally, the fill assemblies can be color coded to identify a particular medicament and the fill ports can also be color coded to identify the fill assembly usable with that dispenser component. For example, the fill port can be of a first color and the mating portion of the second fill assembly can of a color corresponding to the first color.

In using the apparatus of this latest form of the invention, after the peelable seals 446 and 446a (FIG. 63) of fill assembly 386 have been removed and after the container peelable seal 448 has been removed, the reservoir fill step can commence. This is accomplished by first mating the container subassembly with adapter assembly 390. This done, the assemblage thus formed can be interconnected with the delivery component in the manner previously described. With the fill assembly mated with the delivery component, fluid can be expelled from fluid chamber 389 of the container subassembly into the fluid reservoir 306 of the dispenser component by urging container 388 into the annular space defined by the interior wall of hollow housing 414 and the exterior surface of member 413. This is accomplished by gripping finger engaging ears 390a (FIGS. 35 and 63) and then urging the container assembly inwardly with the thumb.

During the initial mating of container assembly 388 with adapter assembly 390, cannula 410 will pierceably engage and penetrate wall 400a of connector assembly 400 thereby opening fluid communication between reservoir 389 of container 388 and the internal fluid passageway of cannula 410. Once wall 400a has been penetrated, an inward force exerted on the container subassembly will cause pusher rod or member 413 to urge plunger 398 inwardly of container reservoir 389 from a first location proximate open end 392 to a second location proximate closed end 394. As plunger 399 moves inwardly, fluid within reservoir 389 will be caused to flow into central fluid passageway 412 of member 413. Fluid will then flow past the umbrella check valve 430, into the interior passageway of cannula 424 and finally into fluid reservoir 306 via inlet 310. As the fluid under pressure flows through inlet passageway 310, the stored energy means, or elastomeric member 316, will be distended in the manner shown in FIG. 37 causing internal stresses to be built up within the elastomeric member, which stresses tend to return the member toward its less stressed initial starting state.

Once reservoir 306 has been filled, fluid will remain in the reservoir until a line clamp 492 of infusion line 382 is opened (FIG. 35). Line 382 is connected proximate its inboard end to connector 380 in the manner shown in FIG. 35. In addition to line 382, the infusion means of this form of the invention includes a gas vent and filter unit 494 which is disposed between line clamp 492 and connector 380. A suitable luer connector 495 is affixed to the outboard end of the infusion line. The infusion means also includes bolus injection means in the form of a conventional Y-site 496, for infusion into the patient of a bolus dose of the same or alternate medication. After the line clamp is opened, the stored energy source, or distendable membrane 316 will move from its second distended state toward its first less distended state forcing fluid from reservoir 306 into delivery line 382 via outlet passageway 373 and via the flow indicating means of the invention that is similar in construction to that described in incorporated by reference U.S. Pat. No. 5,840,071 (FIG. 37).

The important dose dialing and rate control means of the invention as described in the preceding paragraphs has numerous medical applications. For example, the does dialing feature will permit the health care provider to adjust the volume of medication filled into the dispenser reservoir based on variables Such as body mass index (BMI). The provider will simply dial in the volume of medication to be used rather than grueling over complicated equations in order to determine individualized dosing schedules. In a similar vein, anticoagulants are often used as an adjunct to percutaneous coronary intervention for the prevention of cardiac ishemic complications. This typically requires an initial bolus dose followed by 12-hour continuous infusion. A patient's dose is determined by his body mass index, or BMI. The dose dialing and variable flow rate features of the apparatus of the present invention makes the apparatus ideally suited for this important treatment. Additionally, the apparatus is well suited for ambulatory parenteral delivery of chemotherapeutic medications and allows therapy to be provided in minimally infusive settings, such as the home.

Figure 56:
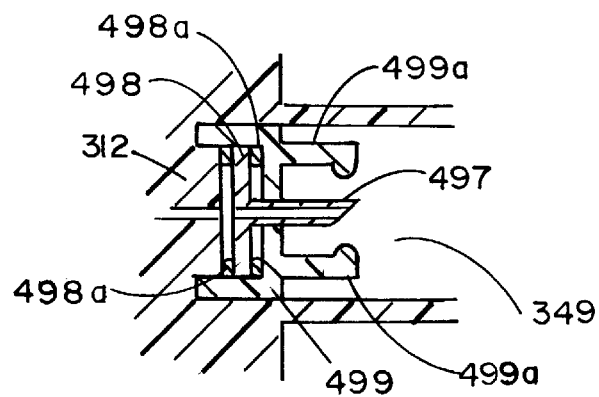
FIG. 56 is a fragmentary cross-sectional view of an alternate form of the cannula assembly of the fluid delivery component of the apparatus of the invention.
Figure 57:
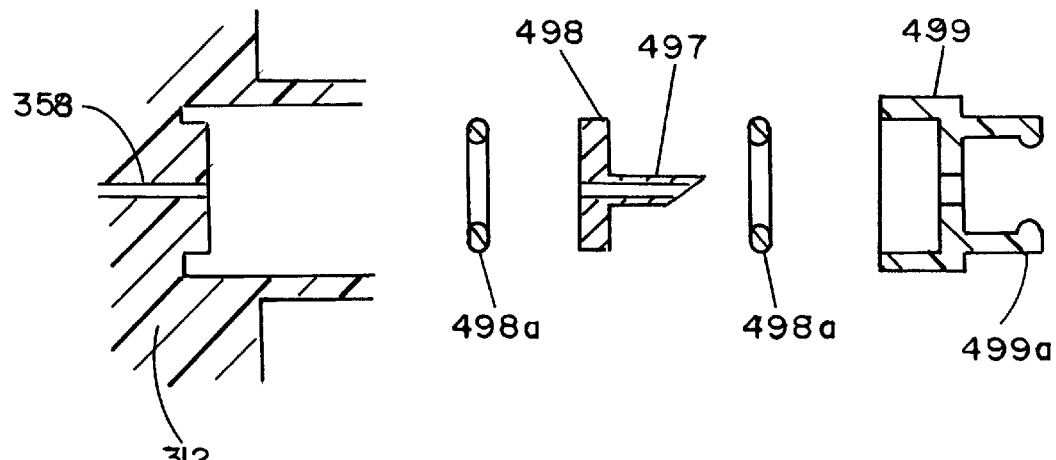
FIG. 57 is an exploded cross-sectional view of the alternate cannula assembly shown in FIG. 56.

Turning next to FIGS. 56 and 57 an alternate form of the delivery device cannula assembly is there shown. This assembly includes a hollow cannula 497, which, like cannula 352, extends into receiving chamber 314 and is adapted to pierce septum 350 of the container subassembly. However, as best seen in FIG. 57, cannula 497 is laser welded to a stainless-steel plate 498. Plate 498 along with hollow cannula 497 is sealably mounted within a needle retainer housing 499 which is of the character best seen in FIG. 57. A pair of O-rings 498a sealably retain plate 498 within housing 499 in the manner shown in FIG. 56. A gripping protuberance 499a is provided on housing 499 and functions to grip the neck portion of container 335 when the container is fully inserted into receiving chamber 314 (see for example FIG. 37).

Figure 67:
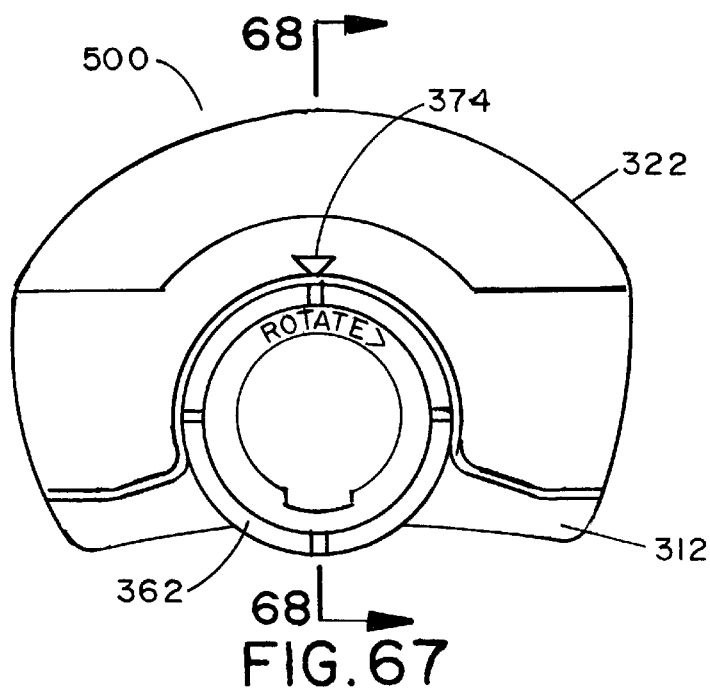
FIG. 67 is a front elevational view of still another embodiment of the fluid delivery apparatus of the invention.
Figure 68:
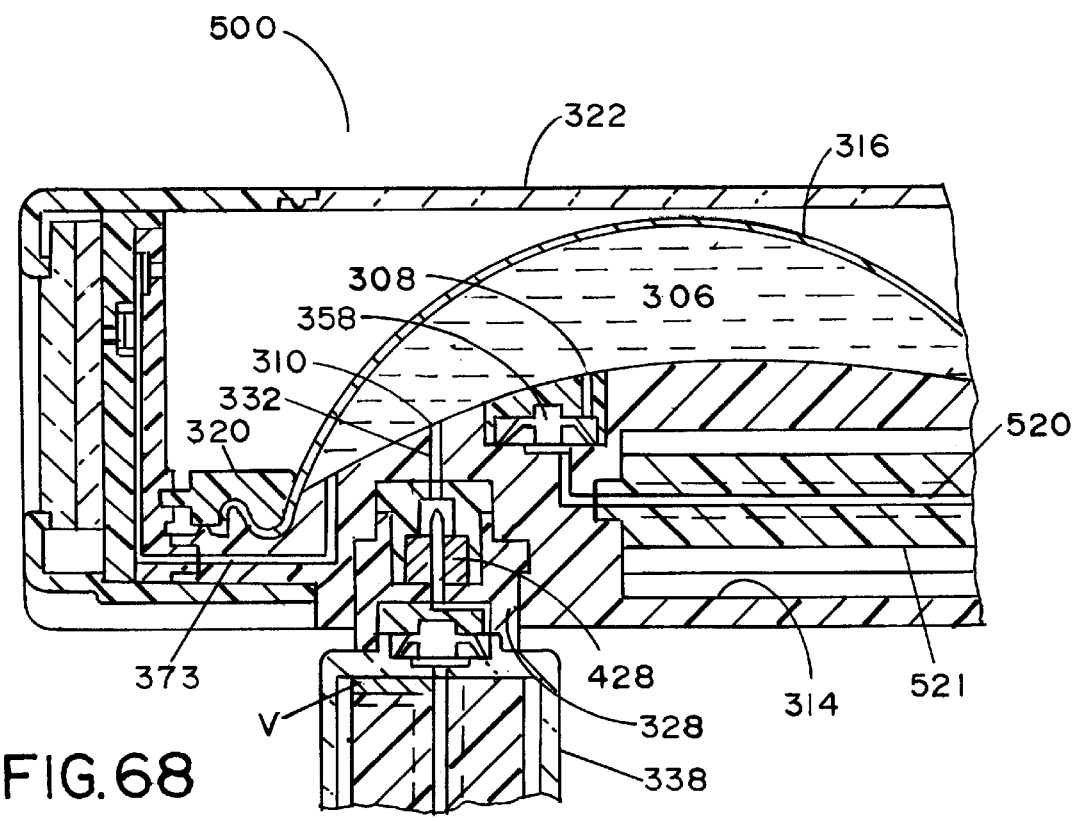
FIG. 68 is a cross-sectional view taken along lines 68—68 of FIG. 67.
Figure 69:
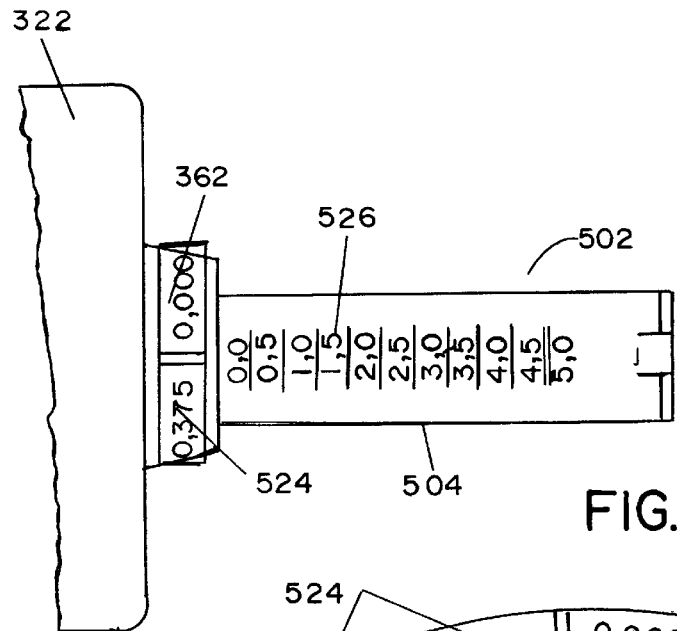
FIG. 69 is a top plan the view of the right hand portion of the apparatus shown in FIG. 68.

Referring now to FIGS. 67 through 69, still another form of the apparatus of the invention for controlled delivery of medicinal fluid to a patient is there shown and generally designated by the numeral 500. This embodiment of the invention is similar in many respects to the previously described embodiment and like numerals are used in FIGS. 67 through 69 to identify like components. The primary difference between the embodiment shown in FIGS. 67 through 69 and that shown in FIGS. 35 and 37 resides in the fact that the first fill assembly of the apparatus is of a somewhat different construction. More particularly, the first fill assembly, which is generally designated in FIG. 68 by the numeral 502, comprises an assembly that can be filled with fluid in the field.

Turning particularly to FIGS. 68, 70, 72 and 72A, the first fill assembly 502 of the apparatus can be seen to comprise a two-part adapter sleeve 504, which is adapted to mate with the advancing means of the invention which is identical to that previously described and functions to advance the adapter sleeve 504 into the receiving chamber 314. Parts 504a and 504b are held in an assembled configuration by an adhesively applied tape connector 505 (FIGS. 70 and 72). The first fill assembly 502 also includes a container, or vial, 506 having a fluid chamber 508 for containing the fluid to be added to the reservoir 306 of a fluid dispenser (FIG. 72). The fluid can be a diluent or any of the medicaments or beneficial agents previously described. Vial 506 has open ends 506a and 506b and closely receives a pierceable, piston-like plunger 510 which, during field filling, is movable within vial 506 from a first position where it is proximate end 506a of the vial to a second position where it is disposed proximate end 506b of the vial. Container 506 can be a glass vial or any other suitable sterile container for containing the fluid that is to be used in filling or partially filling the reservoir of the fluid delivery device. Vial 506 can also be constructed from various plastic materials. Materials suitable for the construction of plastic vials include polycarbonate, high density polyethylene, polypropylene, nylon, polystyrene, polyamides, styrenes, and various like materials.

In a manner presently to be described, as the fluid chamber of the vial is filled with fluid using a container filling means, here comprising a needleless syringe "NS" (FIG. 72), piston 510 is moved within the vial by fluid pressure from the first position shown in FIG. 70 to a second position shown in FIG. 72. Piston 510 is provided with a plurality of circumferentially extending sealing beads 510a which sealably engage the inner walls of container 506 as the piston moves internally thereof so as to prevent fluid leakage past the piston.

Figure 72B:
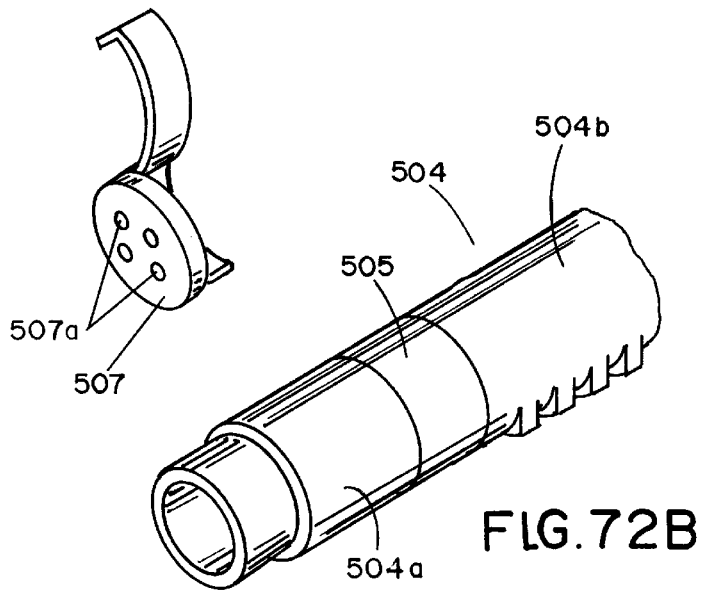
FIG. 72B is a generally perspective, exploded view of the forward end of the assemblage shown in FIG. 72A.
Figure 72A:
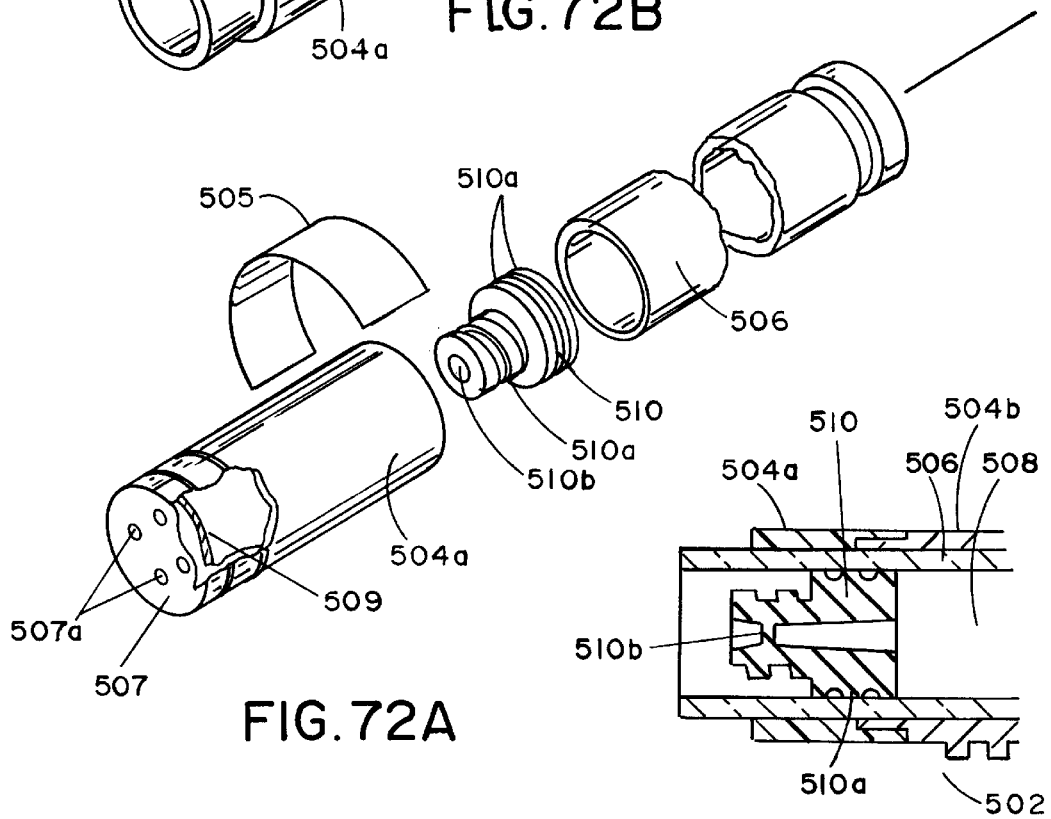
FIG. 72A is a generally perspective, exploded view of the assemblage shown in FIG. 72.
Figure 72C:
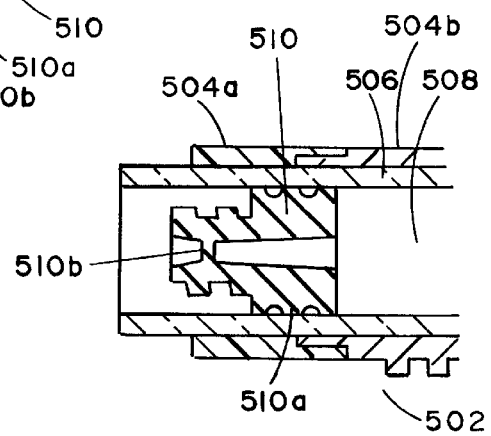
FIG. 72C is a fragmentary, cross-sectional view of the filling assembly showing the peel away end wall having been removed.
Figure 72A:
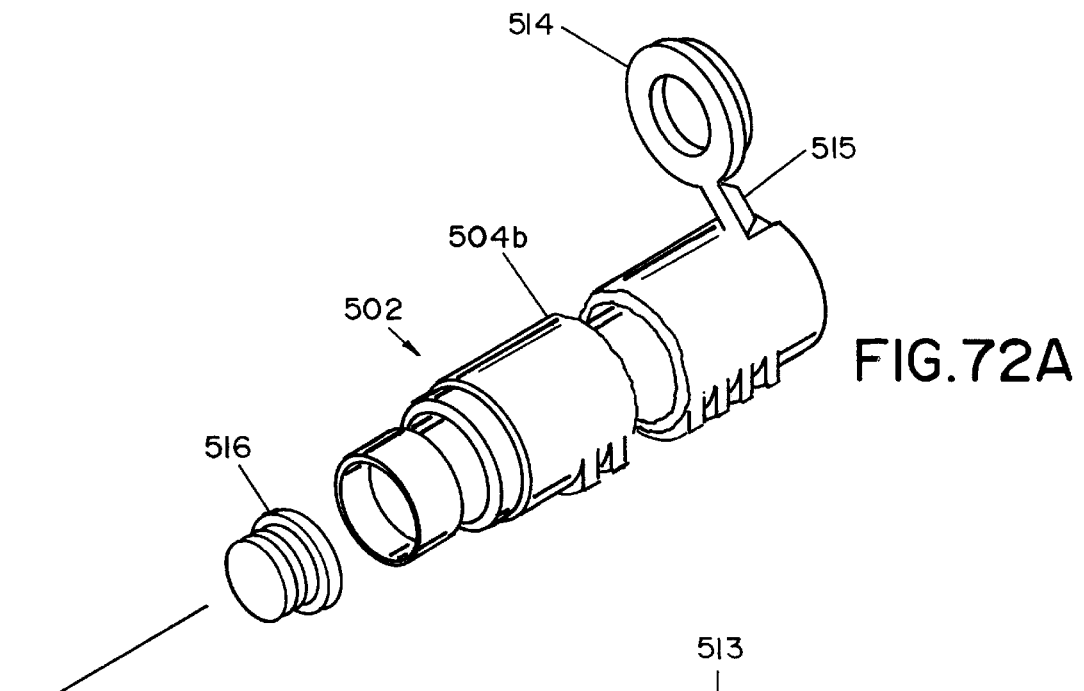

Referring particularly to FIGS. 70, 72 and 72A, after the vial assembly has been assembled in the manner shown in FIG. 70 and closure cap 514 has been pivoted upwardly about living hinge 515 in the manner shown in FIGS. 72 and 72A to expose to view the syringe connector means of the invention, chamber 508 can be filled with fluid. The syringe connector means of this form of the invention which functions to interconnect the container with a needleless syringe NS here comprises sealing means for sealing the open end 506a of vial 506. In the present form of the invention, this sealing means comprises a slit septum 516 which will accept the blunt-end cannula 518 of the needleless syringe in the manner shown in FIG. 72.

In filling vial 506 in the field, as fluid is forced from the filling syringe NS into reservoir 508 the fluid will impinge on plunger 510 forcing it to the left until it engages a peel-away end wall 507. End wall 507 is provided with a plurality of vent apertures 507a. Bonded to end wall 507 is a hydrophobic vent patch 509 (FIG. 72A). When the vial 506 is filled in the manner thus described, when the end wall 507 is peeled away and filled assemblage is then mated with the delivery component, end 520a of an elongated hollow cannula 520, which is positioned within the pusher means or member 521 of this latest form of the invention will pierce end wall 510b of plunger 510 to enable filling of the dispenser reservoir 306. As best seen in FIG. 68 the inboard end of cannula 520 is in fluid communication with inlet 308 to reservoir 306 via umbrella check valve 358. As shown in FIG. 70, adapter sleeve 504 is provided with a plurality of longitudinally spaced apart advancing teeth 522 which are of similar construction to the teeth 371 formed on sleeve 342.

Figure 69A:
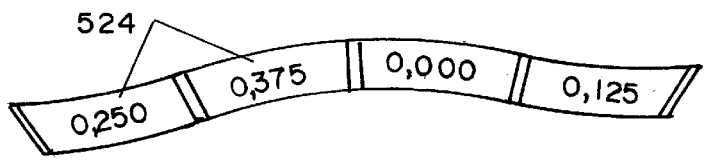
FIG. 69A is a generally schematic view of the indicating indicia imprinted on the dose dial of the apparatus of this latest form of the invention.
Figure 68A:
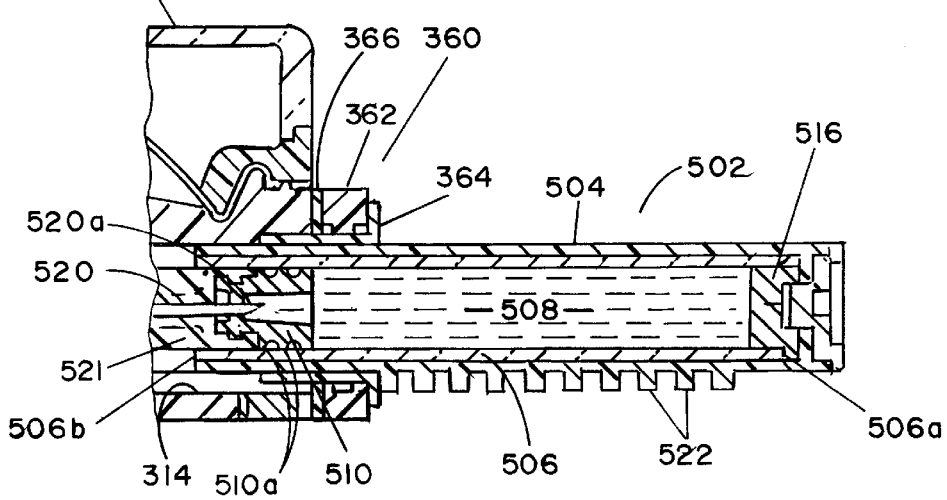

With the various components of the apparatus in the position shown in FIG. 68, one full rotation of the dose dial 362 in the manner previously described will result in the incremental advancement of the first fill assembly and will result in the incremental flow of fluid into reservoir 306. As shown and FIGS. 69 and 69A, dose dial 362 is provided with incremental indicia 524 and adapter sleeve 504 is provided with longitudinally spaced incremental indicia 526. As in the earlier described embodiment, a full rotation of dose dial 362 will result in one-half or one-tenth of the volume of the container 506 being introduced into reservoir 306. Similarly, rotation of dose dial 362 in ¼ turn increments as indicated by indicia 524 will result in 0.0125 of the volume of container 506 being introduced into reservoir 306.

Figure 72E:
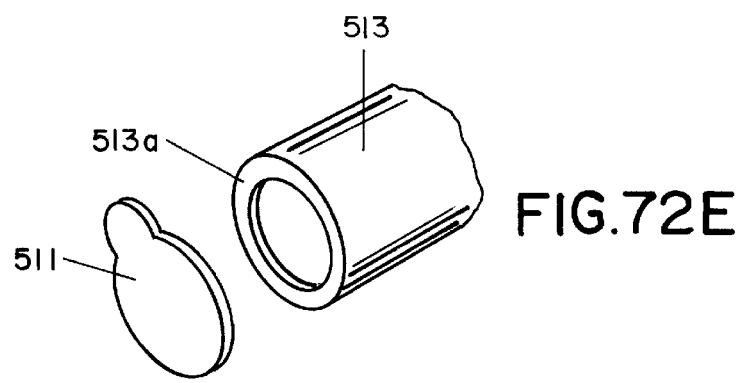
FIG. 72E is a generally perspective, fragmentary, exploded view of the alternate fill assembly showing the peel away cap removed.
Figure 72D:
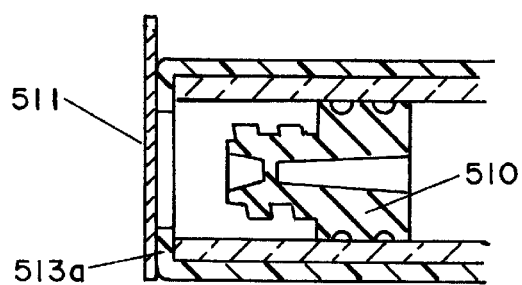
FIG. 72D is a fragmentary, cross-sectional view of the forward portion of an alternate form of the first fill assembly.
Figure 73:
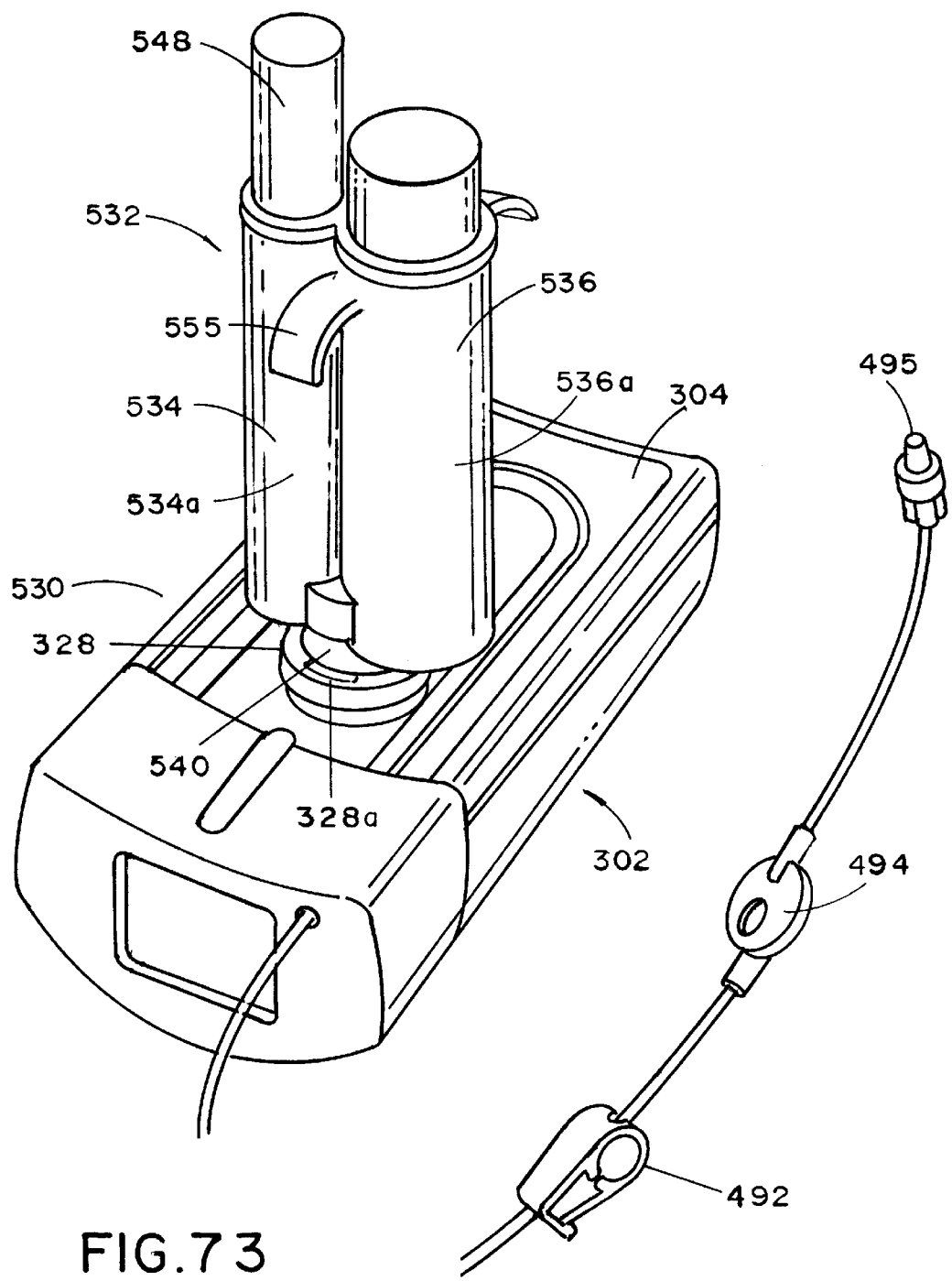
FIG. 73 is a generally perspective bottom view of yet another form of the fluid delivery apparatus of the present invention.

Referring to FIGS. 72D and 72E an alternate form of first fill assembly is there shown. This embodiment is substantially identical to that shown in FIGS. 70 through 72C, but includes a tear-away peel cap 511. Additionally an inwardly protruding lip 513a is formed on adapter sleeve 513 to retain plunger 510 within the sleeve as it is advanced forwardly thereof (FIG. 72E).

Turning next to FIG. 73 through 85, still another form of the fluid delivery apparatus of the invention is there shown and generally designated by the numeral 530. This apparatus is also similar to the apparatus shown in FIGS. 35 through 72 and like numerals are used in FIGS. 73 through 85 to identify like components. In this latest embodiment of the invention the fluid delivery component is identical to that previously described. However, in this latest form of the invention an entirely different, dual housing, second fill assembly is provided. This second fill assembly, which is generally designated by the numeral 532, is interconnected with the outlet port of the fluid delivery component by means of connector means comprising a barrel connector that is of similar construction to barrel connector 418. However, unlike the previously described second fill assembly, this latest fill assembly comprises a pair of side-by-side fill assemblies generally designated in the drawings by the numerals 534 and a 536 respectively. Each of the fill assemblies is interconnected with and is in fluid communication with the connector, or barrel like portion 540, that is provided with circumferentially spaced apart bayonet-like tabs 542. As in the earlier described embodiments, tabs 542 are lockably received within circumferentially spaced-apart slots 328a formed in the inlet port 328 of the fluid delivery component 302.

Figure 77:
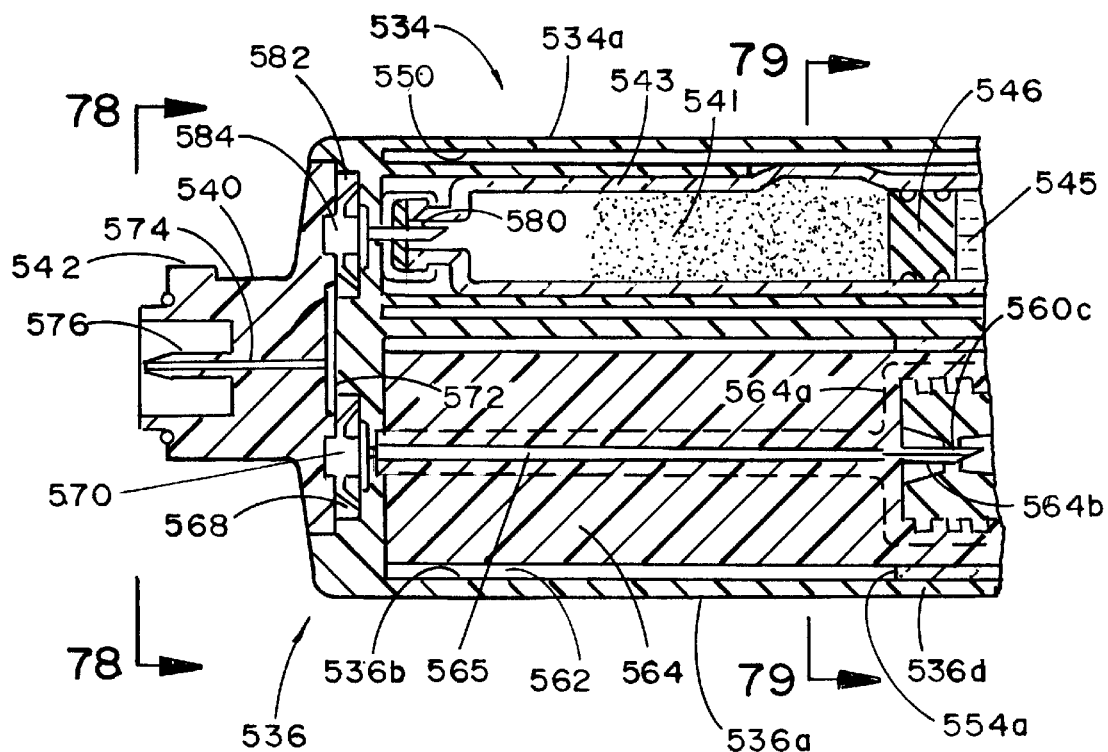
FIG. 77 is a cross-sectional view taken along lines 77—77 of FIG. 76.
Figure 76A:
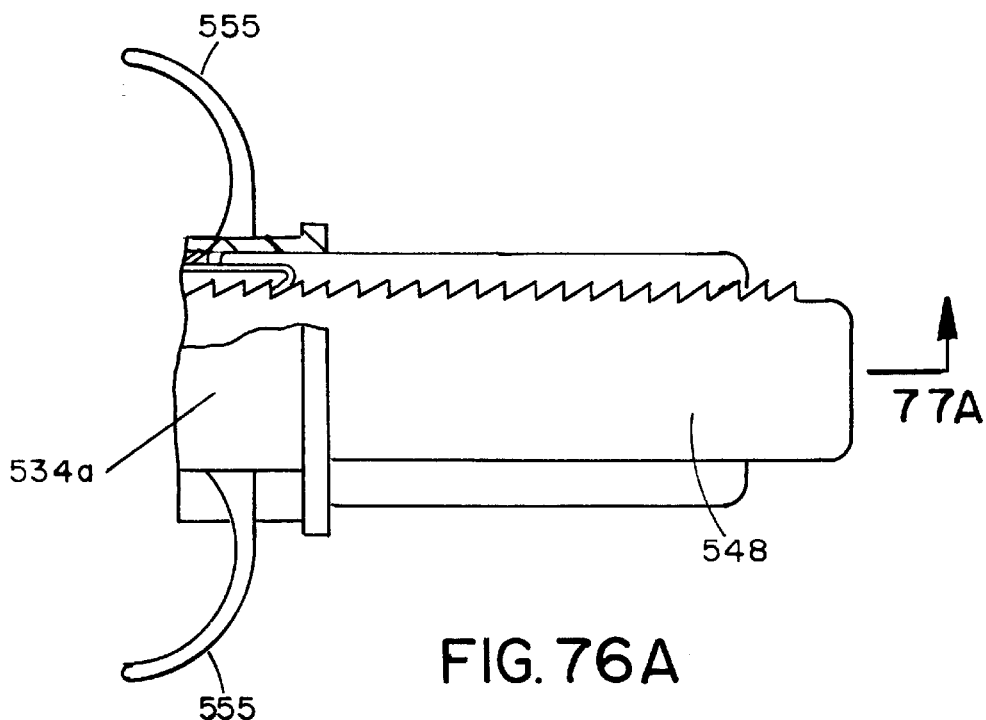
Figure 77A:
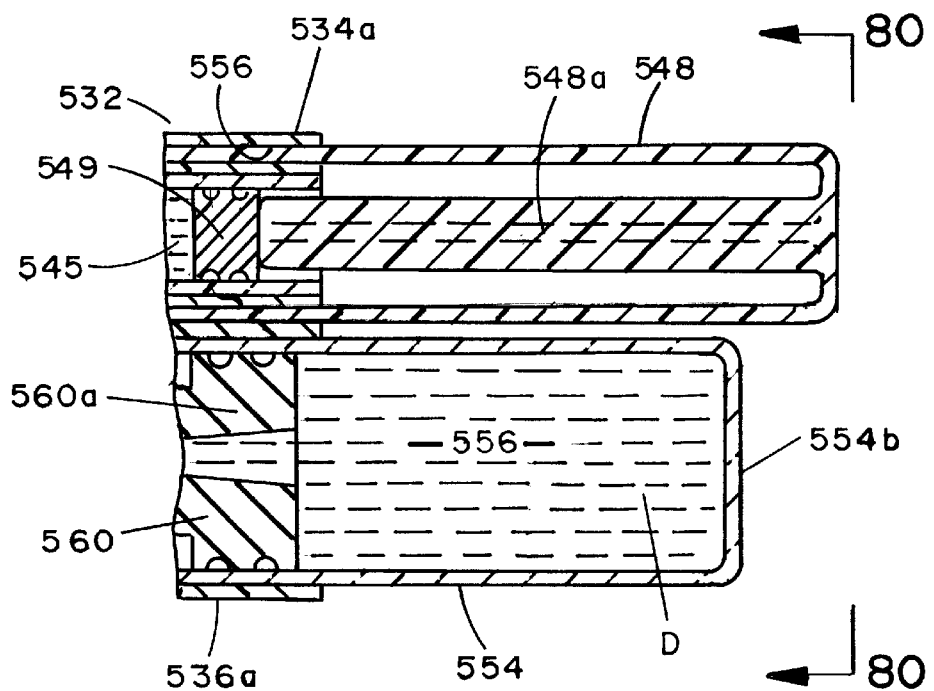
Figure 80:
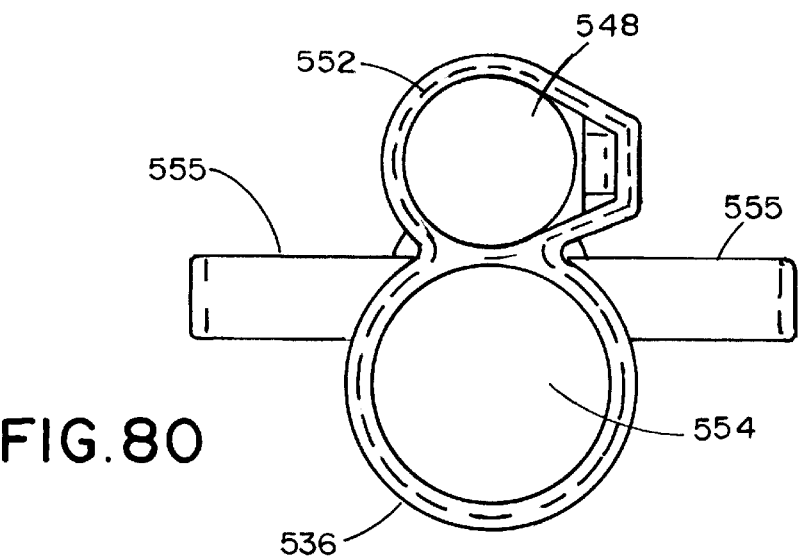
FIG. 80 is a view taken along lines 80—80 of FIG. 77.
Figure 79:
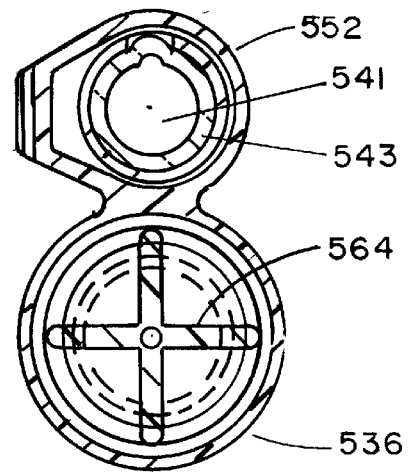
FIG. 79 is a cross-sectional view taken along lines 79—79 of FIG. 77.
Figure 78:
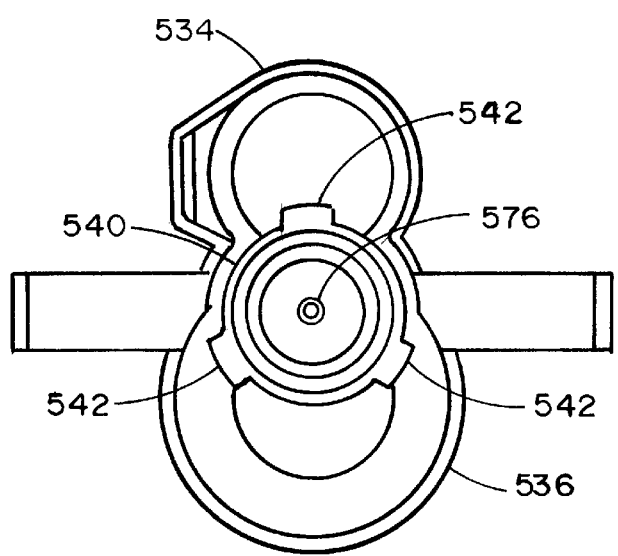
FIG. 78 is a view taken along lines 78—78 of FIG. 77.
Figure 86:
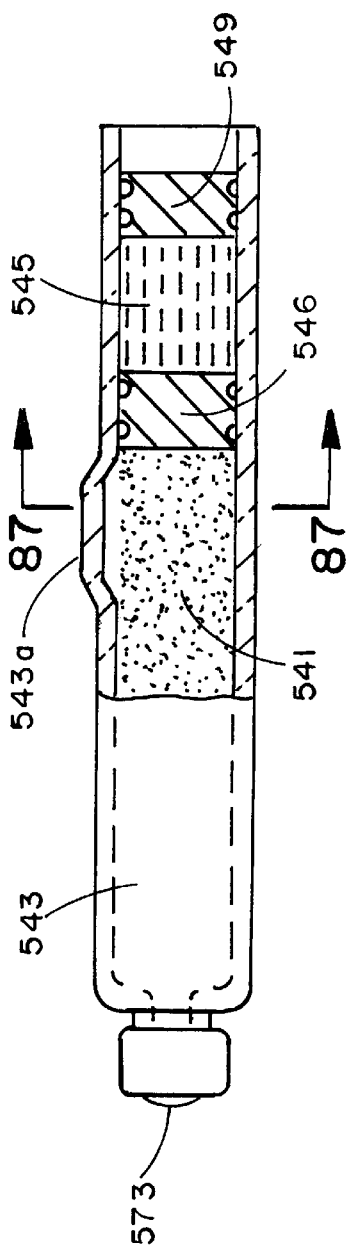
FIG. 86 is a side elevational view partly broken away to show internal construction of one of the vial assemblies of the apparatus of the invention shown in FIG. 73.

Referring particularly to FIG. 77, fill assembly 534 includes a housing 534a which accepts a vial assembly 543 which uniquely contains a lyophilized drug 541 that is separated from a reconstituting fluid 545 by a barrier stopper 546. Lyophilized drug 541 can, by way of example, comprise anti-infectives, anticoagulants and chemotherapeutic agents. Vial assembly 543 is telescopically receivable within an adapter sleeve 548 that is, in turn, receivable within an annular shaped opening 550 formed within housing 534a of the second piggy-back fill assembly 536. Adapter sleeve 548 includes a pusher member 548a that engages a plunger 549 to push it forwardly within the container assembly to cause mixing of the fluid 545 with the lyophilized drug 541. This novel mixing step will be described more fully in the paragraphs which follow.

Fill assembly 536 includes a housing 536a which accepts a fluid container 554 that includes a fluid chamber 556. Container 554 has a first open end 554a that is sealably closed by a plunger assembly 560 and a closed second end 554b. Container 554 is receivable within an annular space 562 formed between a pusher member 564 and the interior wall 536b of housing 536a of the second fill means 532. As best seen by referring to FIGS. 81 and 82, plunger assembly S60 includes a body portion 560a and a threaded connector portion 560b which can be threadably interconnected with pusher member 564 in the manner illustrated and FIG. 77. Pusher member 564 includes a head portion 564a that is internally threaded to receive connector portion 560b of plunger assembly 560 (FIG. 83). Pusher assembly 564 also includes a hollow cannula 564b that extends into an interior chamber defined by a threaded portion 564a. With this construction, when plunger assembly 560 is threadably interconnected with pusher member 564 in the manner shown in FIG. 77, hollow cannula 564b will pierce a central wall 560c formed in connector portion 560b, thereby opening fluid communication between fluid chamber 556 and the internal passageway 565 of hollow cannula 564b. An inward pressure exerted on container 554 using finger engaging wings 555 (FIG. 76) will then urge the fluid contained within fluid chamber 556 to flow into hollow cannula 564b and then into a chamber 568 formed in assembly 536 that houses a conventional umbrella check valve 570 (FIG. 77). Fluid under pressure will then flow past umbrella valve 570 into a passageway 572 formed in connector barrel portion 540, then into a longitudinally extending passageway 574 and finally into the internal passageway of a piercing cannula 576 which is connected to barrel assembly 540 and forms a part of the connector means of the invention. Once again the fluid contained within chamber 556 can take various forms as, for example, a diluent D. When the second fill assembly 532 of this latest form of the invention is mated with the delivery component in the manner shown and FIG. 73, cannula 576 will pierce septum 428 of the delivery device thereby permitting fluid to flow into reservoir 306 via inlet 310 (see for example FIGS. 37 and 68).

Figure 74:
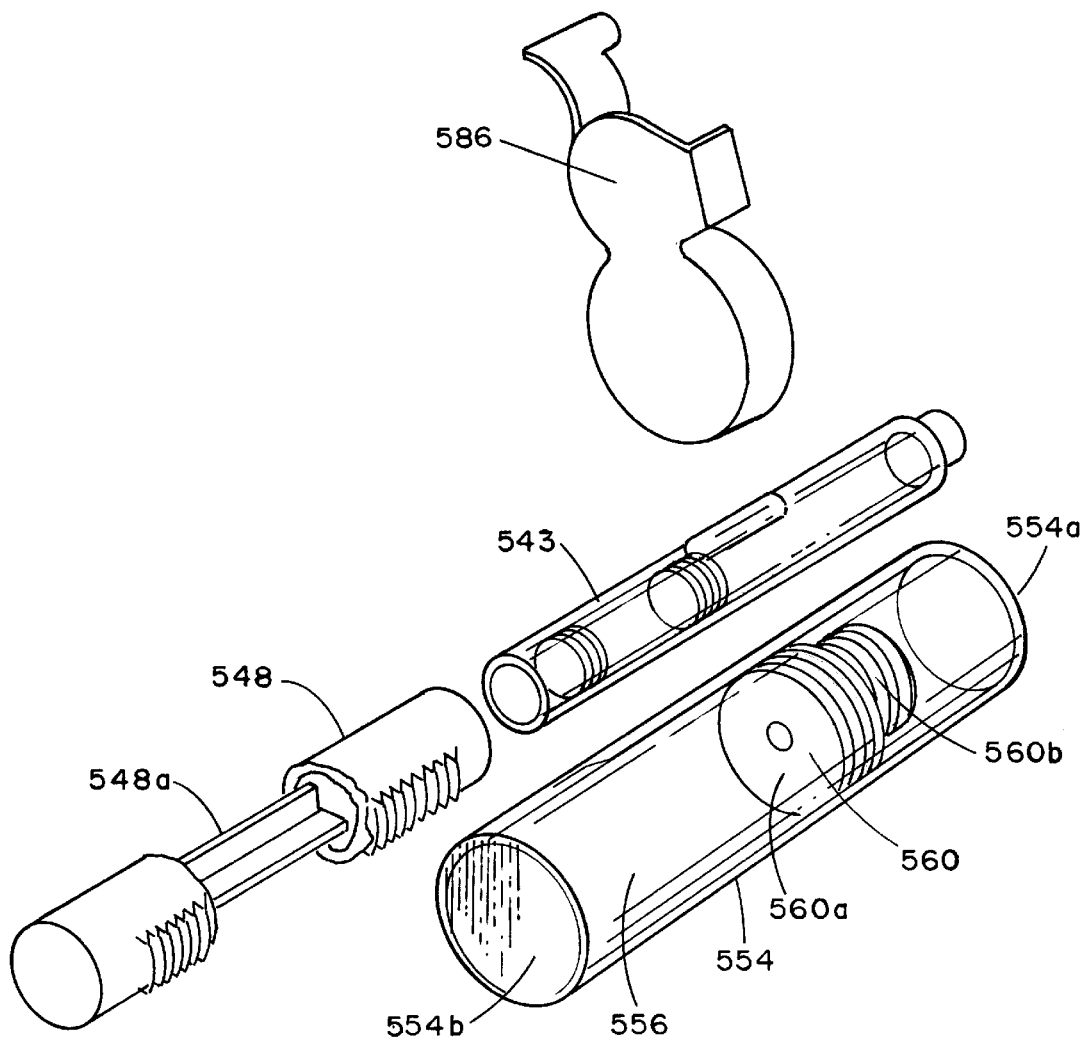
FIG. 74 is a generally perspective exploded view of the second fill assembly of this latest form of the apparatus of the invention.
Figure 74A:
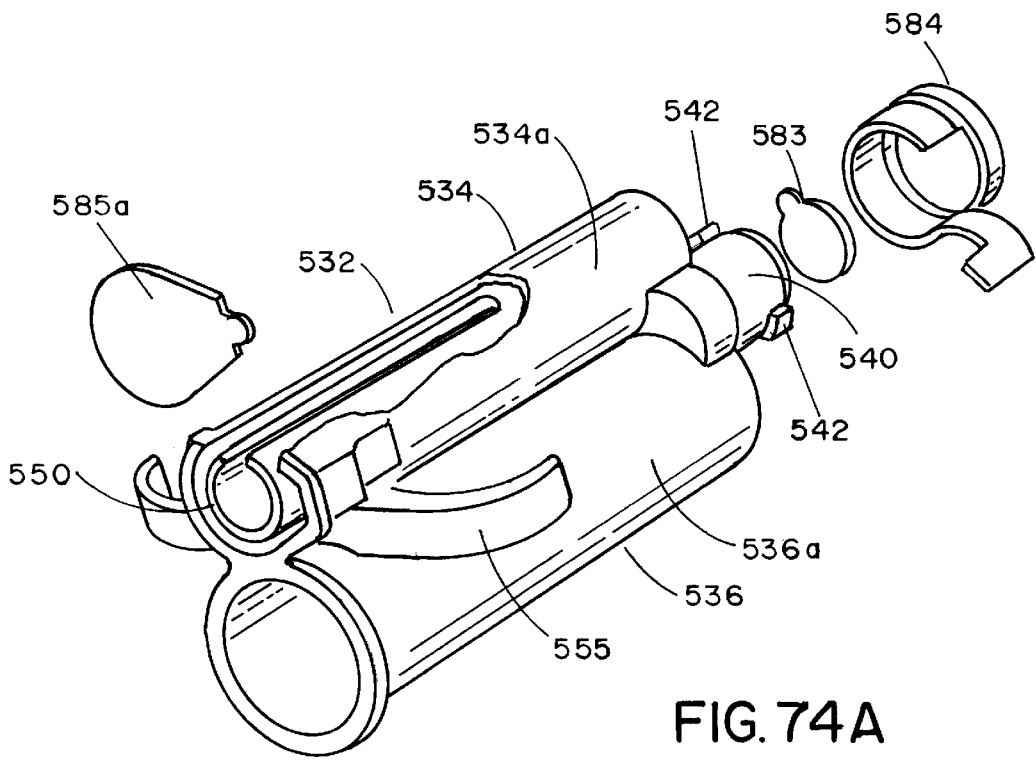
Figure 75:
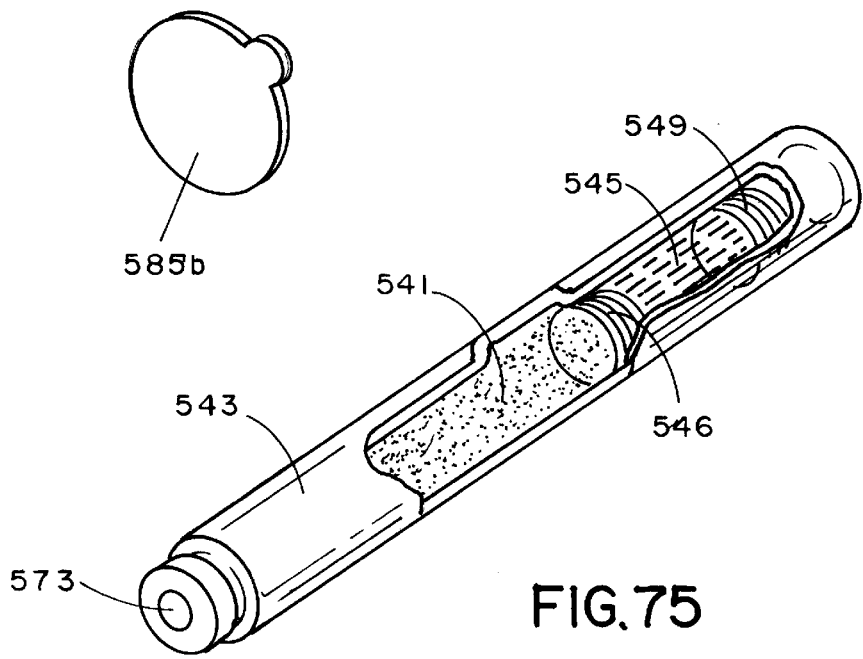
FIG. 75 is a generally perspective view partly broken away to show internal construction of a fill container used in conjunction with the second fill assembly shown in FIG. 74.
Figure 76:
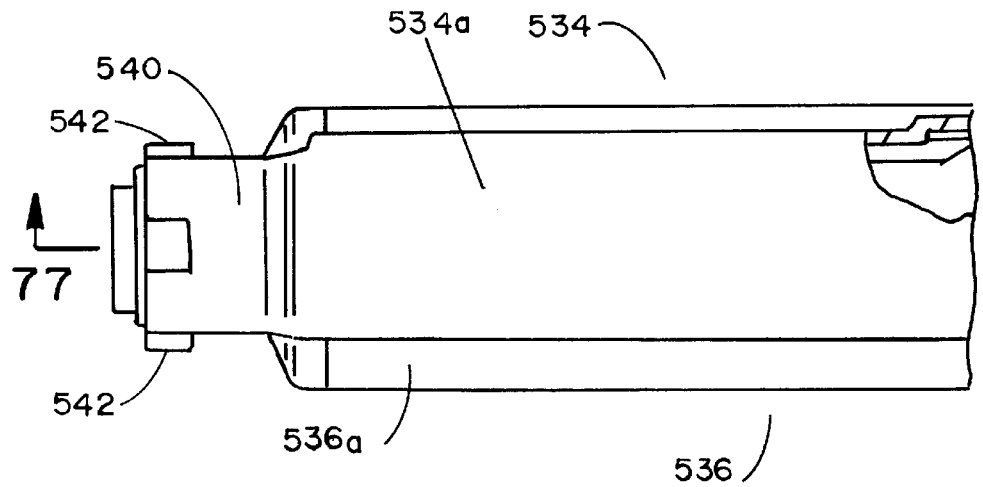
FIG. 76 is a top plan view partly broken away to show internal construction of the second fill assembly of this latest form of the apparatus of the invention.
Figure 88:
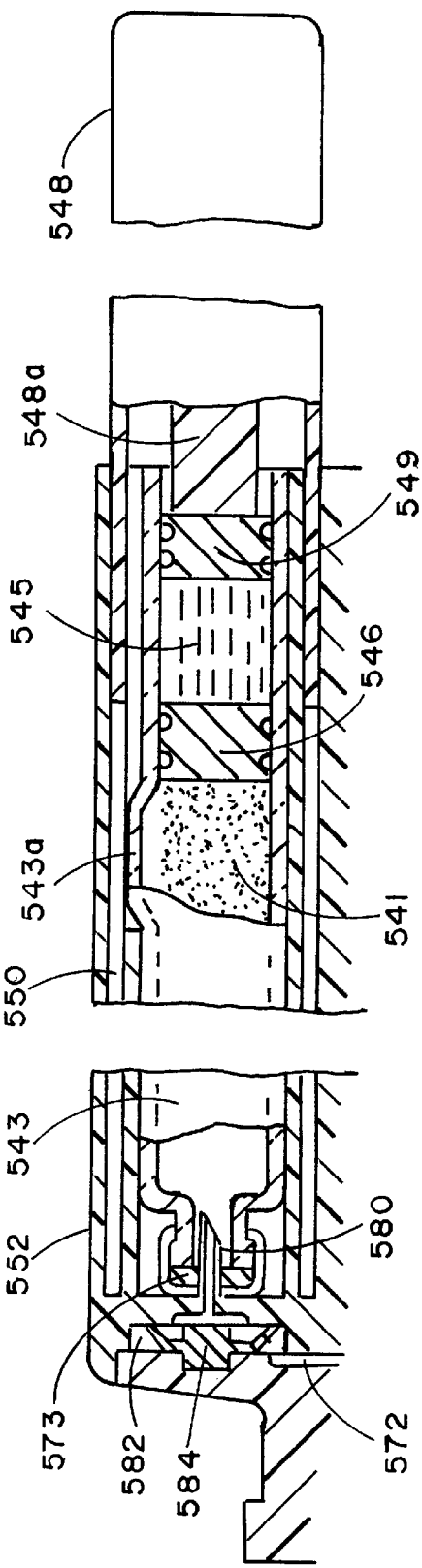
FIG. 88 is a side elevational, cross-sectional view showing the vial assembly of FIG. 86 in position within one of the dual housings of the second vial assembly of this alternate form of the invention.

Considering once again the novel fill assembly 534 and referring particularly to FIGS. 86 through 90, container 543 as presented to adapter sleeve 548 is sealed at one end by a plunger 549 and at the other end by a pierceable septum 573 (FIG. 88). Formed intermediate the ends of vial 543 is a raised outer wall portion 543a which permits fluid 545 to bypass barrier 546 as the barrier member is urged inwardly of the container by pressure exerted thereon by the fluid 545. Fluid 545 exerts pressure on barrier member 546 as a result of pusher member 548a exerting inward pressure on plunger 549, which pressure is, in turn, caused by the inward movement of plunger 549 due to the urging of pusher member 548a as sleeve 548 is pushed inwardly of annular space 550. More particularly, once assembly 543 is mated with assembly 552 in a manner shown in FIG. 88, an inward pressure exerted on sleeve 548 will cause the components of the assembly to move into the position shown in FIG. 89. In this position, it is apparent, that fluid 545 will flow past barrier member 546 via wall portion 543a and will reconstitute lyophilized drug 541. A continued inward pressure exerted on sleeve 548 will cause the components 546 and 549 to move into the position shown and FIG. 90 wherein all of the fluid 545 has been intermixed with drug 541 and the reconstituted drug thus formed has been transferred by a hollow cannula 580 into a chamber 582 that houses an umbrella check valve 584. Fluid under pressure will then flow past check valve 584 into passageway 572, then into passageway 574 and finally into hollow cannula 576 (FIG. 77). When the second fill assembly of this latest form of the invention is mated with the fluid delivery devise as shown and FIG. 73, cannula 576 will pierce septum 428 permitting the reconstituted drug to flow into reservoir 306 via inlet 310 (see FIG. 37). Prior to use, barrel portion 540 is substantially sealed by a peal cover 583 and a tear-a-way cap 584. Similarly, prior to loading containers 543 and 554, housing 534a and 536a of the second fill assembly are sealably closed by peal covers 585a and 585b and a tear-a-way cap 586 (FIG. 74).

To interconnect second fill assembly 532 with the fluid delivery apparatus, barrel-like portion, or closure cap 540 of the fill assembly is mated with fill port 328 formed in base 304. As the barrel-like connector portion enters the lower portion of the fill port, the circumferentially spaced, bayonet type connectors or locking tabs 542 of closure cap 540 are received between the circumferentially spaced tab receiving slots 328a formed in the fill port. Relative rotation of the fill assembly and the fluid delivery component will effect a sterile interconnection of the second fill assembly with the fill port 328. As the second fill assembly 532 is aseptically mated with the delivery component, cannula 576 of the fill assembly will pierce a pierceable septum 428 which is mounted within fill port 328. This done, an inward pressure exerted on sleeve 554 will cause cannula 564b to pierce wall 560c of plunger 560 and will cause fluid to flow into cannula 564b, past umbrella check valve 570, through cannula 576 and into fluid reservoir 306 via inlet 310.

It is to be understood that the fluid contained within container 554 may comprise a diluent or a wide variety of selected medicinal fluids. The fluid may be used to partially fill reservoir 306 prior filling the reservoir with the mixture comprising fluid 545 and drug 541 contained with the vial assembly 534. This latter mentioned fluid mixture can be introduced into a reservoir 306 by mating container 543 with housing 534a in the manner shown in FIG. 77 and then by exerting an inward pressure on sleeve 548 (FIG. 77). This inward pressure will cause pusher rod or member 548a to urge plunger 549 inwardly of container 543 in a manner previously described. A continued inward movement of sleeve 548 will cause fluid 545 to mix with drug 541 and will cause the mixture thus formed to flow into hollow cannula 580, passed umbrella check valve 584, into passageway 572, into passageway 574 and thence into hollow cannula 576. The fluid flowing through hollow cannula 576 will then flow into reservoir 306 via inlet 310 where the mixture will, in turn, be intermixed with the fluid such as the diluent "D" previously introduced into the reservoir from container 554.

Having now described the invention in detail in accordance with the requirements of the patent statutes, those skilled in this art will have no difficulty in making changes and modifications in the individual parts or their relative assembly in order to meet specific requirements or conditions. Such changes and modifications may be made without departing from the scope and spirit of the invention, as set forth in the following claims.

We claim:

1. A fluid delivery device for infusing medicinal fluids into a patient at a controlled rate comprising:
   (a) housing having a fill port and a receiving chamber;
   (b) stored energy means disposed within said housing for forming a reservoir having an inlet and an outlet, said stored energy means comprising at least one distendable membrane, said membrane being distendable in a manner to establish internal stresses, said stresses tending to move said membrane toward a less distended configuration; and
   (c) filling means connected to said housing for filling said reservoir, said filling means including:
      (i) a first filling assembly comprising:
         a. a container subassembly including a container having a fluid chamber and displacement means movable relative to said fluid for dispensing fluid from said chamber;
         b. an adapter subassembly comprising a hollow housing for telescopically receiving at least part of said container subassembly and means for moving said displacement means relative to said fluid chamber of said container; and
         c. advancing means connected to said housing for controllably advancing said adapter subassembly into said receiving chamber of said housing, said advancing means comprising an advancing dial rotatably connected to said housing for movement between first aid second positions; and
      (ii) a second filling assembly comprising a fluid transport assembly mateable with said fill port.

2. The fluid delivery device as defined in claim 1 in which said fluid transport assembly includes a piercing cannula and in which said fill port includes a pierceable septum pierceable by a said piercing cannula.

3. The fluid delivery device as defined in claim 1 in which said fill port includes connector means for removably interconnecting said fluid transport assembly with said fill port and in which said fluid transport assembly includes at least one connector tab for interconnection with said connector means of said fill port.

4. The fluid delivery device as defined in claim 3 in which said connector means comprises at least one slot formed in said fill port for receiving said connector tab of said fluid transport assembly.

5. A fluid delivery device for infusing medicinal fluids into a patient at a control rate comprising:
   (a) housing having a fill port and including a base and a cover connected to said base, said base having a receiving chamber,
   (b) stored energy means connected to said base for forming in conjunction with said base a reservoir having an inlet and an outlet, said stored energy means comprising at least one distendable membrane, said membrane being distendable in a manner to establish internal stresses, said stresses tending to move said membrane toward a less distended configuration, and
   (c) filling means connected to said housing for filling said reservoir, said filling means including:
      (i) a first filling assembly comprising:
         a. a container subassembly including a container having a fluid chamber and displacement means movable relative to said fluid for dispensing fluid from said chamber;
         b. an adapter subassembly comprising a hollow housing having a first open end for telescopically receiving at least a portion of said container of said container subassembly and a second end including means for engagement with said displacement means of said container subassembly to move said displacement means relative to said fluid chamber of said container, said hollow housing having a plurality of longitudinally spaced apart advancing teeth; and
         c. advancing means connected to said housing for controllably advancing said adapter subassembly into said receiving chamber of said housing, said advancing means comprising an advancing dial rotatably connected to said base for rotation between first and second positions, said advancing dial including teeth engaging means for engagement with said teeth of said hollow housing to incrementally advance said hollow housing into said receiving chamber upon rotation of said advancing dial; and
      (ii) a second filling assembly comprising a fluid transport assembly connected to said fill port.

6. The fluid delivery device as defined in claim 5 in which said fluid transport assembly includes a piercing cannula and in which said fill port includes a pierceable septum pierceable by a said piercing cannula.

7. The fluid delivery device as defined in claim 6 in which one of said fill port and said fluid transport assembly includes circumferentially spaced connector tabs.

8. The fluid delivery device as defined in claim 7 in which one of said fill port and said fluid transport assembly includes circumferentially spaced slots for receiving said connector tabs.

9. A fluid delivery device for infusing medicinal fluids into a patient at a control rate comprising:
   (a) housing having a fill port and including a base and a cover connected to said base, said base having a receiving chamber;
   (b) stored energy means connected to said base for forming in conjunction with said base a reservoir having an inlet and an outlet, said stored energy means comprising at least one distendable membrane, said membrane being distendable in a manner to establish internal stresses, said stresses tending to move said membrane toward a less distended configuration; and
   (c) filling means connected to said housing for filling said reservoir, said filling means including:
      (i) a first filling assembly comprising:
         a. a container subassembly including a container having a fluid chamber and displacement means for dispensing fluid from said chamber;
         b. an adapter subassembly comprising a hollow housing having a first open end for telescopically receiving at least a portion of said container of said container subassembly said hollow housing having a plurality of longitudinally spaced apart advancing teeth; and
         c. advancing means connected to said housing for controllably advancing said adapter subassembly into said receiving chamber of said housing, said advancing means comprising an advancing dial rotatably connected to said base for rotation between first and second positions, said advancing dial including teeth engaging means for engagement with said teeth of said hollow housing to incrementally advance said hollow housing into said receiving chamber upon rotation of said advancing dial, said advancing dial of said advancing means including circumferentially spaced incremental indicating indicia and said hollow housing of said adapter subassembly including longitudinally spaced dose volume indicating indicia; and
      (ii) a second fill port assembly comprising a fluid transport a assembly mateable with said fill port.

10. The fluid delivery device as defined in claim 9 in which said fill port is of a first color and the mating portions of said transport assembly is of a color corresponding to said first color.

* * * * *